US012780925B2

(12) United States Patent
Chang et al.

(10) Patent No.: US 12,780,925 B2
(45) Date of Patent: Nov. 3, 2026

(54) PROTEINS BINDING NKG2D, CD16 AND A TUMOR-ASSOCIATED ANTIGEN

(71) Applicant: Dragonfly Therapeutics, LLC, Waltham, MA (US)

(72) Inventors: Gregory P. Chang, Medford, MA (US); Ann F. Cheung, Lincoln, MA (US); William Haney, Wayland, MA (US); Bradley M. Lunde, Lebanon, NH (US); Bianka Prinz, Lebanon, NH (US)

(73) Assignee: Dragonfly Therapeutics, LLC, Waltham, MA (US)

( * ) Notice: Subject to any disclaimer, the term of this patent is extended or adjusted under 35 U.S.C. 154(b) by 56 days.

(21) Appl. No.: 16/615,261

(22) PCT Filed: May 23, 2018

(86) PCT No.: PCT/US2018/034223

§ 371 (c)(1),
(2) Date: Nov. 20, 2019

(87) PCT Pub. No.: WO2018/217947

PCT Pub. Date: Nov. 29, 2018

(65) Prior Publication Data

US 2020/0157227 A1 May 21, 2020

Related U.S. Application Data

(60) Provisional application No. 62/552,146, filed on Aug. 30, 2017, provisional application No. 62/546,292, filed on Aug. 16, 2017, provisional application No. 62/546,296, filed on Aug. 16, 2017, provisional application No. 62/539,416, filed on Jul. 31, 2017, provisional application No. 62/539,419, filed on Jul. 31, 2017, provisional application No. 62/539,396, filed on Jul. 31, 2017, provisional application No. 62/510,173, filed on May 23, 2017.

(51) Int. Cl.

| | |
|---|---|
| ***C07K 16/28*** | (2006.01) |
| ***A61K 40/15*** | (2025.01) |
| ***A61K 40/31*** | (2025.01) |
| ***A61K 40/42*** | (2025.01) |
| ***A61P 35/00*** | (2006.01) |
| ***C12N 5/0783*** | (2010.01) |

(52) U.S. Cl.

CPC .......... *C07K 16/2851* (2013.01); *A61K 40/15* (2025.01); *A61K 40/31* (2025.01); *A61K 40/4202* (2025.01); *A61K 40/4221* (2025.01); *A61K 40/4224* (2025.01); *A61P 35/00* (2018.01); *C07K 16/283* (2013.01); *C07K 16/2878* (2013.01); *C07K 16/2887* (2013.01); *C07K 16/2893* (2013.01); *C07K 16/2896* (2013.01); *C12N 5/0646* (2013.01)

(58) Field of Classification Search

CPC .............. C07K 16/2851; C07K 16/283; C07K 16/2878; C07K 16/2887; C07K 16/2893; C07K 16/2896; A61P 35/00; A61K 35/17

See application file for complete search history.

(56) References Cited

U.S. PATENT DOCUMENTS

| | | | |
|---|---|---|---|
| 5,776,427 A | 7/1998 | Thorpe et al. | |
| 5,807,706 A | 9/1998 | Carter et al. | |
| 5,863,538 A | 1/1999 | Thorpe et al. | |
| 5,959,084 A | 9/1999 | Ring et al. | |
| 6,036,955 A | 3/2000 | Thorpe et al. | |
| 6,129,914 A | 10/2000 | Weiner et al. | |
| 6,210,670 B1 | 4/2001 | Berg | |
| 6,294,167 B1 | 9/2001 | Lindhofer et al. | |
| 6,572,856 B1 | 6/2003 | Taylor et al. | |
| 6,737,056 B1 | 5/2004 | Presta | |
| 7,112,324 B1 | 9/2006 | Dorken et al. | |
| 7,235,641 B2 | 6/2007 | Kufer et al. | |
| 7,575,923 B2 | 8/2009 | Dorken et al. | |
| 7,635,472 B2 | 12/2009 | Kufer et al. | |
| 7,642,228 B2 | 1/2010 | Carter et al. | |
| 7,695,936 B2 | 4/2010 | Carter et al. | |
| 7,820,166 B2 | 10/2010 | Lanzavecchia | |
| 7,879,985 B2 * | 2/2011 | Urso | A61P 19/02<br>530/388.22 |
| 7,951,917 B1 | 5/2011 | Arathoon et al. | |
| 8,007,796 B2 | 8/2011 | Baeuerle et al. | |
| 8,076,459 B2 | 12/2011 | Hofmeister et al. | |
| 8,101,722 B2 | 1/2012 | Kufer et al. | |

(Continued)

FOREIGN PATENT DOCUMENTS

| | | |
|---|---|---|
| CA | 2990511 A1 | 12/2016 |
| CN | 101945893 A | 1/2011 |

(Continued)

OTHER PUBLICATIONS

Steigerwald et al. "Human IgG1 antibodies antagonizing activating receptor NKG2D on natural killer cells", MAbs. Mar.-Apr. 2009;1(2):115-27. (Year: 2009).*

Stein et al. "Natural Killer (NK)- and T-Cell Engaging Antibody-Derived Therapeutics", Antibodies 2012, 1, 88-123 (Year: 2012).*

Lamminmaki et al. "Crystal structure of a recombinant anti-estradiol Fab fragment in complex with 17beta-estradiol", JBC 2001, 276:36687-36694 (Year: 2001).*

Rudikoff et al. "Single amino acid altering antigen-binding specificity", Proc Natl Acad Sci USA 1982 vol. 79 p. 1979 (Year: 1979).*

MacCallum et al. "Antibody-antigen Interactions: Contact Analysis and Binding Site Topography", J. Mol. Biol. (1996) 262, 732-745 (Year: 1996).*

(Continued)

*Primary Examiner* — Peter Johansen

(74) *Attorney, Agent, or Firm* — Goodwin Procter LLP

(57) ABSTRACT

Multi-specific binding proteins that binds NKG2D receptor, CD 16, and a tumor-associated antigen selected from CD37, CD20, CD19, CD22, CD30, CD52, and CD133 are described, as well as pharmaceutical compositions and therapeutic methods useful for the treatment of cancer.

13 Claims, 21 Drawing Sheets

Specification includes a Sequence Listing.

(56) References Cited

U.S. PATENT DOCUMENTS 8,236,308 B2 8/2012 Kischel et al.
8,409,577 B2 4/2013 Thompson et al.
8,518,403 B2 8/2013 Hoffmann et al.
8,592,562 B2 11/2013 Kannan et al.
8,658,765 B2 2/2014 Martin, Jr. et al.
8,679,785 B2 3/2014 Carter et al.
8,759,494 B2 6/2014 Bachmann
8,784,821 B1 7/2014 Kufer et al.
8,796,420 B2 8/2014 Martin, Jr. et al.
8,840,888 B2 9/2014 Nagorsen et al.
8,931,406 B2 1/2015 Detloff et al.
9,079,969 B2 7/2015 Martin, Jr. et al.
9,102,736 B2 8/2015 Hofmeister et al.
9,127,064 B2 9/2015 Urso et al.
9,150,656 B2 10/2015 Johnson et al.
9,150,663 B2 10/2015 Labrijn et al.
9,200,078 B2 12/2015 Bachmann
9,248,181 B2 2/2016 De Kruif et al.
9,248,182 B2 2/2016 De Kruif et al.
9,273,136 B2 3/2016 Rader et al.
9,334,331 B2 5/2016 Igawa et al.
9,447,185 B2 9/2016 Romagne et al.
9,493,578 B2 11/2016 Lazar et al.
9,562,109 B2 2/2017 Von Kreudenstein et al.
9,587,036 B2 3/2017 Kufer et al.
9,637,557 B2 5/2017 Scheer et al.
9,683,053 B2 6/2017 Blein et al.
9,690,969 B2 6/2017 Okamoto
9,718,893 B2 8/2017 Jung et al.
9,951,145 B2 4/2018 Kim et al.
9,963,513 B2 5/2018 Vu et al.
10,040,853 B2 8/2018 Spies et al.
10,047,167 B2 8/2018 Demarest et al.
10,059,765 B2 8/2018 Velardi et al.
10,377,827 B2 8/2019 Swanson et al.
10,421,807 B2 9/2019 Gonzalez et al.
10,526,409 B2 1/2020 Urso et al.
10,767,760 B2 9/2020 Ando
11,084,880 B2 8/2021 Brogdon et al.
11,124,582 B2 9/2021 Ambrogelly et al.
11,787,864 B2 10/2023 Cheung et al.
11,834,506 B2 * 12/2023 Chang .................. C07K 16/283
11,884,732 B2 1/2024 Chang et al.
11,884,733 B2 1/2024 Chang et al.
11,939,384 B1 3/2024 Chang et al.
2002/0103345 A1 8/2002 Zhu
2002/0193569 A1 12/2002 Hanna
2003/0095965 A1 5/2003 Van Beneden et al.
2004/0038339 A1 * 2/2004 Kufer ...................... A61P 35/02
435/325
2004/0052783 A1 3/2004 Weiner et al.
2004/0115198 A1 6/2004 Spies et al.
2005/0037002 A1 2/2005 Velardi et al.
2005/0054019 A1 3/2005 Michaud et al.
2005/0058639 A1 3/2005 Gudas et al.
2005/0158307 A1 7/2005 Spies et al.
2005/0244416 A1 11/2005 Jung
2006/0018899 A1 1/2006 Kao et al.
2006/0235201 A1 10/2006 Kischel
2006/0246004 A1 11/2006 Adams et al.
2007/0004909 A1 1/2007 Johnson et al.
2007/0071759 A1 3/2007 Shin et al.
2007/0179086 A1 8/2007 Gliniak et al.
2007/0190063 A1 8/2007 Bahjat et al.
2008/0025975 A1 1/2008 Weiner et al.
2008/0299137 A1 12/2008 Svendsen et al.
2008/0305105 A1 12/2008 Kufer et al.
2009/0142352 A1 6/2009 Jackson et al.
2009/0175867 A1 7/2009 Thompson et al.
2009/0226442 A1 9/2009 Huet et al.
2009/0226466 A1 9/2009 Fong et al.
2009/0252729 A1 10/2009 Farrington et al.
2009/0304693 A1 12/2009 Ghayur et al.
2009/0304696 A1 12/2009 Lawson et al.
2010/0009866 A1 1/2010 Prinz et al.
2010/0055034 A1 3/2010 Martin et al.
2010/0056764 A1 3/2010 Urso et al.
2010/0124764 A1 5/2010 Hufton et al.
2010/0174053 A1 7/2010 Johnson et al.
2010/0178298 A1 7/2010 Lindhofer
2010/0260765 A1 10/2010 Barry et al.
2010/0272718 A1 10/2010 Urso et al.
2010/0286374 A1 11/2010 Kannan et al.
2010/0291112 A1 11/2010 Kellner et al.
2010/0310463 A1 12/2010 Cicortas Gunnarsson et al.
2011/0008335 A1 1/2011 Velardi et al.
2011/0020273 A1 1/2011 Chang et al.
2011/0044980 A1 2/2011 Ghayur et al.
2011/0054151 A1 3/2011 Lazar et al.
2011/0150870 A1 6/2011 Rader et al.
2011/0311535 A1 12/2011 Dranoff et al.
2012/0014957 A1 1/2012 Ghayur et al.
2012/0058082 A1 3/2012 Kaplan et al.
2012/0058906 A1 3/2012 Smider et al.
2012/0093823 A1 4/2012 Van Den Brink et al.
2012/0149876 A1 6/2012 Kreudenstein
2012/0171173 A1 7/2012 Ideno et al.
2012/0195900 A1 8/2012 Ghayur et al.
2012/0263722 A1 10/2012 Ghayur et al.
2012/0269723 A1 10/2012 Brinkmann et al.
2012/0294796 A1 11/2012 Johnson et al.
2012/0294857 A1 11/2012 Sentman et al.
2012/0321626 A1 12/2012 Zhou
2012/0328619 A1 12/2012 Fey et al.
2013/0115208 A1 5/2013 Ho et al.
2013/0177555 A1 * 7/2013 Wilkinson ............. C07K 14/00
424/133.1
2013/0209514 A1 8/2013 Gilboa et al.
2013/0216528 A1 8/2013 Cheung et al.
2013/0216544 A1 8/2013 Bachmann
2013/0230525 A1 9/2013 Li et al.
2013/0336977 A1 12/2013 Thompson et al.
2014/0044739 A1 2/2014 Teng et al.
2014/0072579 A1 3/2014 De Kruif et al.
2014/0072581 A1 3/2014 Dixit et al.
2014/0105889 A1 4/2014 Igawa et al.
2014/0112926 A1 4/2014 Liu et al.
2014/0120096 A1 5/2014 Bakker et al.
2014/0127203 A1 5/2014 Thompson et al.
2014/0140999 A1 5/2014 De Kruif et al.
2014/0141022 A1 5/2014 Thompson et al.
2014/0154250 A1 6/2014 Thompson et al.
2014/0154252 A1 6/2014 Thompson et al.
2014/0199294 A1 7/2014 Mimoto et al.
2014/0234342 A1 8/2014 Narni-Mancinelli et al.
2014/0242077 A1 8/2014 Choi et al.
2014/0271617 A1 9/2014 Igawa et al.
2014/0288275 A1 9/2014 Moore et al.
2014/0294827 A1 10/2014 Gastwirt et al.
2014/0302064 A1 10/2014 Moore
2014/0363426 A1 12/2014 Moore et al.
2014/0364340 A1 12/2014 Vasquez et al.
2014/0377269 A1 12/2014 Mabry et al.
2015/0050269 A1 2/2015 Igawa et al.
2015/0056206 A1 2/2015 Zhou
2015/0079088 A1 3/2015 Lowman et al.
2015/0119555 A1 4/2015 Jung et al.
2015/0166636 A1 6/2015 Igawa et al.
2015/0166654 A1 6/2015 Igawa et al.
2015/0175697 A1 6/2015 Bonvini et al.
2015/0175700 A1 6/2015 Lum et al.
2015/0203591 A1 7/2015 Yancopoulos et al.
2015/0210765 A1 7/2015 Roschke et al.
2015/0259431 A1 9/2015 Stemmer et al.
2015/0259434 A1 9/2015 Johnson et al.
2015/0274838 A1 10/2015 Johnson et al.
2015/0299319 A1 10/2015 Velardi et al.
2015/0307617 A1 10/2015 Du et al.
2015/0307628 A1 10/2015 Kim et al.
2015/0329637 A1 11/2015 Urech et al.
2015/0353636 A1 12/2015 Parren et al.
2016/0017038 A1 * 1/2016 Koenig .................. A61P 37/04
530/387.3
2016/0024214 A1 1/2016 Urso et al.

(56) References Cited

U.S. PATENT DOCUMENTS

| | | | |
|---|---|---|---|
| 2016/0032009 | A1 | 2/2016 | Cheung et al. |
| 2016/0039942 | A1 | 2/2016 | Cobbold et al. |
| 2016/0046727 | A1 | 2/2016 | Labrijn et al. |
| 2016/0046730 | A1 | 2/2016 | Ghayur et al. |
| 2016/0077105 | A1 | 3/2016 | Bobrowicz et al. |
| 2016/0090426 | A1 | 3/2016 | Zhou et al. |
| 2016/0096892 | A1 | 4/2016 | Brogdon et al. |
| 2016/0122432 | A1 | 5/2016 | Baty et al. |
| 2016/0159882 | A1 | 6/2016 | Landgraf et al. |
| 2016/0159924 | A1 | 6/2016 | Padkjaer et al. |
| 2016/0176968 | A1 | 6/2016 | Chang et al. |
| 2016/0222105 | A1 | 8/2016 | Moore et al. |
| 2016/0289341 | A1 | 10/2016 | Wu |
| 2016/0326249 | A1 | 11/2016 | Ng et al. |
| 2016/0347849 | A1 | 12/2016 | Cai et al. |
| 2016/0369002 | A1 | 12/2016 | Gauthier et al. |
| 2017/0022291 | A1 | 1/2017 | Baruah et al. |
| 2017/0029529 | A1 | 2/2017 | Croasdale et al. |
| 2017/0066827 | A1 | 3/2017 | Pule et al. |
| 2017/0114141 | A1 | 4/2017 | Amann et al. |
| 2017/0233472 | A1 | 8/2017 | Barat et al. |
| 2017/0291955 | A1 | 10/2017 | Li et al. |
| 2017/0362321 | A1 | 12/2017 | Campbell et al. |
| 2017/0368169 | A1* | 12/2017 | Loew .................. A61K 38/177 |
| 2017/0369595 | A1 | 12/2017 | Brinkmann et al. |
| 2018/0044415 | A1 | 2/2018 | Escarpe et al. |
| 2018/0057608 | A1 | 3/2018 | Jung et al. |
| 2018/0105594 | A1 | 4/2018 | Urso et al. |
| 2018/0105599 | A1 | 4/2018 | Cobbold et al. |
| 2018/0118851 | A1 | 5/2018 | Comeau et al. |
| 2018/0237519 | A1 | 8/2018 | Caligiuri et al. |
| 2018/0237541 | A1 | 8/2018 | Kim et al. |
| 2018/0273633 | A1 | 9/2018 | Jiang et al. |
| 2018/0312592 | A1 | 11/2018 | Junutula et al. |
| 2018/0346600 | A1 | 12/2018 | Kim et al. |
| 2019/0048079 | A1 | 2/2019 | Spies et al. |
| 2019/0225702 | A1 | 7/2019 | Baeuerle et al. |
| 2019/0359716 | A1 | 11/2019 | Chang et al. |
| 2019/0375838 | A1 | 12/2019 | Chang et al. |
| 2020/0002436 | A1 | 1/2020 | Chang et al. |
| 2020/0024353 | A1 | 1/2020 | Chang et al. |
| 2020/0048347 | A1 | 2/2020 | Miao et al. |
| 2020/0055939 | A1 | 2/2020 | Lombana et al. |
| 2020/0095327 | A1 | 3/2020 | Chang et al. |
| 2020/0157174 | A1 | 5/2020 | Chang et al. |
| 2020/0157226 | A1 | 5/2020 | Chang et al. |
| 2020/0157227 | A1 | 5/2020 | Chang et al. |
| 2020/0165344 | A1 | 5/2020 | Chang et al. |
| 2020/0216544 | A1 | 7/2020 | Chang et al. |
| 2020/0231678 | A1 | 7/2020 | Chang et al. |
| 2020/0231679 | A1 | 7/2020 | Chang et al. |
| 2020/0231700 | A1 | 7/2020 | Cheung et al. |
| 2020/0277383 | A1 | 9/2020 | Chang et al. |
| 2020/0277384 | A1 | 9/2020 | Chang et al. |
| 2020/0376034 | A1 | 12/2020 | Chang et al. |
| 2021/0009718 | A1 | 1/2021 | Ambrogelly et al. |
| 2021/0032349 | A1 | 2/2021 | Dengl et al. |
| 2021/0054082 | A1 | 2/2021 | Chang et al. |
| 2021/0070887 | A1 | 3/2021 | Ambrogelly et al. |
| 2021/0079102 | A1 | 3/2021 | Chang et al. |
| 2021/0101976 | A1 | 4/2021 | Chang et al. |
| 2021/0130471 | A1 | 5/2021 | Chang et al. |
| 2021/0130474 | A1 | 5/2021 | Chang et al. |
| 2021/0130496 | A1 | 5/2021 | Chang et al. |
| 2021/0198369 | A1 | 7/2021 | Chang et al. |
| 2021/0206859 | A1 | 7/2021 | Chang et al. |
| 2021/0214436 | A1 | 7/2021 | Chang et al. |
| 2021/0221894 | A1 | 7/2021 | Bigelow et al. |
| 2021/0238290 | A1 | 8/2021 | Chang et al. |
| 2021/0261668 | A1 | 8/2021 | Chang et al. |
| 2021/0292420 | A1 | 9/2021 | Chang et al. |
| 2021/0363261 | A1 | 11/2021 | Chang et al. |
| 2022/0025037 | A1 | 1/2022 | Baruah et al. |
| 2022/0089760 | A1 | 3/2022 | Begelow et al. |
| 2022/0119533 | A1 | 4/2022 | Cheung et al. |
| 2022/0119534 | A1 | 4/2022 | Baruah et al. |
| 2022/0153848 | A1 | 5/2022 | Chang et al. |
| 2022/0195065 | A1 | 6/2022 | Chang et al. |
| 2022/0380459 | A1 | 12/2022 | Chang et al. |
| 2023/0034186 | A1 | 2/2023 | Cuillerot et al. |
| 2023/0203202 | A1 | 6/2023 | Bigelow et al. |
| 2023/0227562 | A1 | 7/2023 | Chang et al. |
| 2023/0250176 | A1 | 8/2023 | Cheung et al. |
| 2023/0257467 | A1 | 8/2023 | Cheung et al. |
| 2023/0272041 | A1 | 8/2023 | Bigelow et al. |
| 2023/0303702 | A1 | 9/2023 | Chang et al. |
| 2023/0357409 | A1 | 11/2023 | Chang et al. |
| 2023/0391877 | A1 | 12/2023 | Chang et al. |
| 2023/0416402 | A1 | 12/2023 | Cuillerot et al. |

FOREIGN PATENT DOCUMENTS

| | | | |
|---|---|---|---|
| CN | 102378768 | A | 3/2012 |
| CN | 105814084 | | 7/2016 |
| CN | 105906722 | A | 8/2016 |
| DE | 102013019352 | A1 | 9/2015 |
| EP | 627940 | A1 | 12/1994 |
| EP | 845998 | A1 | 6/1998 |
| EP | 871673 | A1 | 10/1998 |
| EP | 1124568 | A1 | 8/2001 |
| EP | 1769000 | B1 | 4/2007 |
| EP | 2185595 | A1 | 5/2010 |
| EP | 2222706 | B2 | 9/2010 |
| EP | 2927321 | A1 | 10/2015 |
| EP | 2930188 | A1 | 10/2015 |
| EP | 2942629 | A1 | 11/2015 |
| EP | 2982380 | A1 | 2/2016 |
| EP | 2990416 | A1 | 3/2016 |
| KR | 10-2013-0103325 | | 9/2013 |
| KR | 10-2014-0067944 | | 6/2014 |
| RU | 2588668 | C2 | 7/2016 |
| RU | 2593720 | C2 | 8/2016 |
| RU | 2608504 | C2 | 1/2017 |
| WO | WO-1988008854 | A1 | 11/1988 |
| WO | WO-1989006544 | A1 | 7/1989 |
| WO | WO 1996/027011 | | 9/1996 |
| WO | WO-2001071005 | A2 | 9/2001 |
| WO | WO-2004056873 | A1 | 7/2004 |
| WO | WO 2005/003172 | | 1/2005 |
| WO | WO 2005/009465 | | 2/2005 |
| WO | WO 2005/105849 | | 11/2005 |
| WO | WO-2006037960 | A2 | 4/2006 |
| WO | WO-2007002905 | A1 | 1/2007 |
| WO | WO 2007/044756 | | 4/2007 |
| WO | WO-2007042573 | A2 | 4/2007 |
| WO | WO-2007055926 | A1 | 5/2007 |
| WO | WO-2007097812 | A2 | 8/2007 |
| WO | WO 2008/127735 | A1 | 10/2008 |
| WO | WO-2009/007124 | A1 | 1/2009 |
| WO | WO-2009077483 | A1 | 6/2009 |
| WO | WO 2009/089004 | | 7/2009 |
| WO | WO-2010017103 | A2 | 2/2010 |
| WO | WO-2010080124 | A2 | 7/2010 |
| WO | WO-2010151792 | A1 | 12/2010 |
| WO | WO-2011014659 | A2 | 2/2011 |
| WO | WO 2011/076922 | | 6/2011 |
| WO | WO-2011075636 | A2 | 6/2011 |
| WO | WO 2011/109400 | | 9/2011 |
| WO | WO 2011/131746 | | 10/2011 |
| WO | WO 2011/143545 | | 11/2011 |
| WO | WO-2012006490 | A2 | 1/2012 |
| WO | WO 2012/025530 | | 3/2012 |
| WO | WO 2012/032080 | | 3/2012 |
| WO | WO-2012034039 | A2 | 3/2012 |
| WO | WO 2012/045752 | A1 | 4/2012 |
| WO | WO 2012/058768 | | 5/2012 |
| WO | WO 2012/115241 | | 8/2012 |
| WO | WO-2012125850 | A1 | 9/2012 |
| WO | WO 2012/131555 | | 10/2012 |
| WO | WO-2012158818 | A2 | 11/2012 |
| WO | WO-2012162482 | A1 | 11/2012 |
| WO | WO 2012/163805 | | 12/2012 |
| WO | WO-2013013700 | A1 | 1/2013 |
| WO | WO-2013036799 | A2 | 3/2013 |

(56) References Cited

FOREIGN PATENT DOCUMENTS

WO WO-2013038191 A2 3/2013
WO WO-2013063702 5/2013
WO WO-2013092001 A1 6/2013
WO WO-2013113615 A1 8/2013
WO WO-2013192594 A2 12/2013
WO WO-2014001324 A1 1/2014
WO WO-2014012085 A2 1/2014
WO WO 2014/079000 5/2014
WO WO 2014/084607 6/2014
WO WO 2014/110601 7/2014
WO WO-2014124326 A1 8/2014
WO WO-2014131712 A1 9/2014
WO WO-2014144763 A2 9/2014
WO WO-2014145806 A2 9/2014
WO WO-2014159940 A1 10/2014
WO WO-2014165818 A2 10/2014
WO WO-2014198748 A1 12/2014
WO WO-2015009856 A2 1/2015
WO WO 2015/036606 3/2015
WO WO-2015036582 A2 3/2015
WO WO-2015063187 A1 5/2015
WO WO-2015070061 A1 5/2015
WO WO-2015089344 A1 6/2015
WO WO-2015095412 A1 6/2015
WO WO-2015095539 A1 6/2015
WO WO 2015/095972 7/2015
WO WO 2015/150447 10/2015
WO WO-2015153765 A1 10/2015
WO WO-2015153912 A1 10/2015
WO WO-2015158636 A1 10/2015
WO WO-2015169781 A1 11/2015
WO WO-2015181282 A1 12/2015
WO WO-2015184203 A1 12/2015
WO WO-2015184207 A1 * 12/2015 ......... A61K 39/3955
WO WO-2015197582 A1 12/2015
WO WO-2015197593 A1 12/2015
WO WO-2015197598 A2 12/2015
WO WO-2016001810 A1 1/2016
WO WO-2016011571 A1 1/2016
WO WO-2016023909 A1 2/2016
WO WO-2016025880 A1 2/2016
WO WO-2016028672 A1 2/2016
WO WO 2016/032334 3/2016
WO WO 2016/070959 5/2016
WO WO 2016/090278 6/2016
WO WO-2016097408 A1 6/2016
WO WO-2016100533 A2 6/2016
WO WO-2016109774 A1 7/2016
WO WO-2016115274 A1 7/2016
WO WO-2016122701 A1 8/2016
WO WO-2016134371 A2 8/2016
WO WO 2016/135041 9/2016
WO WO-2016135066 A1 9/2016
WO WO-2016142768 A1 9/2016
WO WO-2016146702 A1 9/2016
WO WO-2016/166139 A1 10/2016
WO WO-2016161390 A1 10/2016
WO WO-2016164369 A2 10/2016
WO WO-2016164637 A1 10/2016
WO WO-2016166629 A1 10/2016
WO WO-2016184592 A1 11/2016
WO WO-2016187220 A2 11/2016
WO WO-2016191305 A1 12/2016
WO WO-2016196237 A1 12/2016
WO WO-2016201300 A1 12/2016
WO WO-2016201389 A2 12/2016
WO WO-2016207273 A2 * 12/2016 ............. A61P 31/04
WO WO-2016207278 A1 12/2016
WO WO-2017/011342 A1 1/2017
WO WO-2017005732 A1 1/2017
WO WO-2017008169 A1 1/2017
WO WO-2017021349 A1 2/2017
WO WO-2017048824 A1 3/2017
WO WO 2017/079694 5/2017
WO WO-2017075432 A2 5/2017
WO WO-2017079694 A2 5/2017
WO WO-2017081190 A1 5/2017
WO WO-2017083545 A1 5/2017
WO WO-2017114694 A1 7/2017
WO WO-2017124002 A1 7/2017
WO WO-2017125897 A1 7/2017
WO WO-2017143406 A1 8/2017
WO WO 2017/165464 9/2017
WO WO-2017165683 A1 9/2017
WO WO 2017/180813 10/2017
WO WO-2017177337 A1 10/2017
WO WO-2017211873 A1 12/2017
WO WO-2017218707 A2 12/2017
WO WO 2018/045090 3/2018
WO WO-2018098365 A2 5/2018
WO WO-2018119171 A1 6/2018
WO WO-2018148445 A1 8/2018
WO WO-2018148447 A1 8/2018
WO WO-2018148566 A1 8/2018
WO WO-2018148610 A1 8/2018
WO WO-2018152516 A1 8/2018
WO WO-2018152518 A1 8/2018
WO WO-2018152530 A1 8/2018
WO WO-2018152547 A1 8/2018
WO WO-2018157147 A1 8/2018
WO WO-2018201051 A1 11/2018
WO WO-2018217799 A1 11/2018
WO WO-2018217945 A1 11/2018
WO WO-2018217947 A1 11/2018
WO WO-2019028027 A1 2/2019
WO WO-2019035939 A1 2/2019
WO WO-2019040727 A1 2/2019
WO WO-2019051308 A1 3/2019
WO WO-2019055677 A1 3/2019
WO PCT/US2019/045561 8/2019
WO PCT/US2019/045632 8/2019
WO PCT/US2019/045677 8/2019
WO PCT/US2019/045723 8/2019
WO WO-2019157332 A1 8/2019
WO WO-2019157366 A1 8/2019
WO WO-2019164929 A1 8/2019
WO WO-2019164930 A1 8/2019
WO WO-2019195408 A1 10/2019
WO WO-2019195409 A1 10/2019
WO WO-2019217332 A1 11/2019
WO WO-2019222449 A1 11/2019
WO WO 2019/231920 12/2019
WO WO 2020/033587 2/2020
WO WO-2020/033630 A1 2/2020
WO WO 2020/033664 2/2020
WO WO 2020/033702 2/2020
WO WO 2020/086758 4/2020
WO PCT/U82020/048500 8/2020
WO PCT/US2020/048500 8/2020
WO WO-2020172189 A1 8/2020
WO PCT/US2020/055497 10/2020
WO WO 2021/041878 3/2021
WO WO-2021/076554 A1 4/2021
WO WO 2021/076564 4/2021
WO PCT/US2021/044737 8/2021
WO WO 2021/216916 10/2021
WO WO-2021/226163 A2 11/2021
WO WO 2021/226193 11/2021
WO WO-2022/031935 A1 2/2022
WO WO 2022/031965 2/2022
WO WO 2022/187539 9/2022
WO WO-2023/056243 A1 4/2023
WO WO 2023/056252 4/2023
WO WO-2023/107954 A1 6/2023
WO WO2023/107956 6/2023
WO WO 2023/154796 8/2023
WO WO 2023/168384 9/2023

OTHER PUBLICATIONS

Pascalis et al. "Grafting of "Abbreviated" Complementarity-Determining Regions Containing Specificity-Determining Residues Essential for Ligand Contact to Engineer a Less Immunogenic

(56) References Cited

OTHER PUBLICATIONS

Humanized Monoclonal Antibody", The Journal of Immunology (2002) 169, 3076-3084 (Year: 2002).*
Padlan et al. "Structure of an antibody-antigen complex: crystal structure of the HyHEL-10 Fab-lysozyme complex", PNAS 1989, 86: 5938-5942 (Year: 1989).*
Casset et al. "A peptide mimetic of an anti-CD4 monoclonal antibody by rational design", BBRC 2003, 307:198-205 (Year: 2003).*
Vajdos et al. "Comprehensive functional maps of the antigen-binding site of an anti-ErbB2 antibody obtained with shotgun scanning mutagenesis", J. Mol. Biol. (2002) 320, 415-428 (Year: 2002).*
Chen et al. "Selection and analysis of an optimized anti-VEGF antibody: crystal structure of an affinity-matured Fab in complex with antigen", J. Mol. Bio. (1999) 293, 865-881 (Year: 1999).*
Wu et al. "Humanization of a murine monoclonal antibody by simultaneous optimization of framework and CDR residues", J. Mol. Biol. (1999) 294, 151-162 (Year: 1999).*
Hoffman et al. "Blinatumomab, a bi-specific anti-CD19/CD3 BiTE® antibody for the treatment of acute lymphoblastic leukemia: perspectives and current pediatric applications", Front Oncol. Mar. 31, 2014;4:63. (Year: 2014).*
Ha et al. "Immunoglobulin Fc Heterodimer Platform Technology: From Design to Applications in Therapeutic Antibodies and Proteins", Front Immunol. 2016; 7: 394. (Year: 2016).*
Vyas M. and von Strandmann E. "Harnessing NK cells to target chronic lymphocytic leukemia: design and efficacy of novel trispecific immunoligands", Eur. J. Immunol. 2016. 46 (Suppl. 1): 1-1274 (Year: 2016).*
Ahmad et al. (2012) "scFv antibody: principles and clinical application," *Clinical and Developmental Immunology* 2012:1-16.
Averdam et al. (2009) "A Novel System of Polymorphic and Diverse NK Cell Receptors in Primates," *PLoS Genetics* 5(10):e1000688.
Busfield et al. (2014) "Targeting of acute myeloid leukemia in vitro and in vivo with an anti-CD123 mAb engineered for optimal ADCC," *Leukemia* 28(11):2213-2221.
Cai et al. (2014) "Autonomous Stimulation of Cancer Cell Plasticity by the Human NKG2D Lymphocyte Receptor Coexpressed with Its Ligands on Cancer Cells," *PLOS ONE* 9(10):e108942.
Cho et al. (2010) "Delivery of NKG2D Ligand Using an Anti-HER2 Antibody-NKG2D Ligand Fusion Protein Results in an Enhanced Innate and Adaptive Antitumor Response," *Cancer Research* 70(24):10121-10130.
Chu et al. (2014) "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," *Blood* 124(21):2316.
Ding et al. (2018) "Fusion Proteins of NKG2D/NKG2DL in Cancer Immunotherapy," *International Journal of Molecular Sciences* 19(1):177.
Germain et al. (2005) "MHC Class I-Related Chain a Conjugated to Antitumor antibodies Can Sensitize Tumor Cells to Specific Lysis by Natural Killer Cell," *Clinical Cancer Research* 11(20):7516-7522.
Glas et al. (1997) "Analysis of rearranged immunoglobulin heavy chain variable region genes obtained from a bone marrow transplant (BMT) recipient," *Clinical & Experimental Immunology* 107(2):372-380.
Gleason et al. (2012) "Bispecific and Trispecific Killer Cell Engagers Directly Activate Human NK Cells through CD16 Signaling and Induce Cytotoxicity and Cytokine Production," *Molecular Cancer Therapeutics* 11(12):2674-2684.
Gleason et al. (2014) "CD16xCD33 bispecific killer cell engager (BiKE) activates NK cells against primary MDS and MDSC CD33+ targets," *Blood* 123(19):3016-3026.
Hezareh et al. (2001) "Effector Function Activities of a Panel of Mutants of a Broadly Neutralizing Antibody against Human Immunodeficiency Virus Type 1," *Journal of Virology* 75(24):12161-12168.
Jachimowicz et al. (2011) "Induction of In Vitro and In Vivo NK Cell Cytotoxicity Using High-Avidity Immunoligands Targeting Prostate-Specific Membrane Antigen in Prostate Carcinoma," *Mol Cancer Thera*, 10(6): 1036-1045.
Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," Leukemia 26:830-834.
Kellner et al. (2016) "Enhancing natural killer cell-mediated lysis of lymphoma cells by combining therapeutic antibodies with CD20-specific immunoligands engaging NKG2D or NKp30," *OncoImmunology* 5(1):e1058459-1-e1058459-12.
Kellner et al. (2013) "Promoting natural killer cell functions by recombinant immunoligands mimicking an induced self phenotype," *Oncoimmunology* 2(6):e24481.
Kwong et al. (2008) "Generation, affinity maturation, and characterization of a human anti-human NKG2D monoclonal antibody with dual antagonistic and agonistic activity," *Journal of Molecular Biology* 384(5):1143-1156.
Lin et al. (2013) "CD4+ NKG2D+ T cells induce NKG2D down-regulation in natural killer cells in CD86-RAE-1 E transgenic mice," *Immunology* 141(3):401-415.
Liu et al. (2017) "Fc engineering for Developing Therapeutic Bispecific Antibodies and Novel Scaffolds," Frontiers in Immunology 8(38):1-15.
Morvan et al. (2016)."NK cells and cancer: you can teach innate cells new tricks" *Nat Rev Cancer* 16(1):7-19.
Nagasaki et al. (2014) "Interleukin-6 released by colon cancer-associated fibroblasts is critical for tumour angiogenesis: anti-interleukin-6 receptor antibody suppressed angiogenesis and inhibited tumour-stroma interaction," *British Journal of Cancer* 110(2):469-478.
Petricevic et al. (2013) "Trastuzumab mediates antibody-dependent cell-mediated cytotoxicity and phagocytosis to the same extent in both adjuvant and metastatic HER2/neu breast cancer patients," *Journal of Translational Medicine* 11(307).
Raab et al. (2014) "Fc-Optimized NKG2D-Fc Constructs Induce NK Cell Antibody-Dependent Cellular Cytotoxicity Against Breast Cancer Cells Independently of HER2/neu Expression Status," *Journal of Immunology* 193(8):4261-72.
Romee et al. (2013) "NK cell CD16 surface expression and function is regulated by a disintegrin and metalloprotease-17 (ADAM17)," *Blood* 121(18):3599-608.
Schuster et al. (2015) "Immunotherapy with the trifunctional anti-CD20 x anti-CD3 antibody FBTA05 (Lymphomun) in paediatric high-risk patients with recurrent CD20-positive B cell malignancies," *British Journal of Haematology* 169(1):90-102.
Smits et al. (2016) "Designing multivalent proteins based on natural killer cell receptors and their ligands as immunotherapy for cancer," *Expert Opinion on Biological Therapy* 16(9):1105-1112.
Spear et al. (2013) "NKG2D ligands as therapeutic targets," *Cancer Immunology* 13(2):8.
Steigerwald et al. (2009) "Human IgG1 antibodies antagonizing activating receptor NKG2D on natural killer cells," *mAbs* 1(2):115-127.
Steinbacher et al. (2015) "An Fc-optimized NKG2D-immunoglobulin G fusion protein for induction of natural killer cell reactivity against leukemia," *International Journal of Cancer* 136(5):1073-1084.
Strong (2002) "Asymmetric ligand recognition by the activating natural killer cell receptor NKG2D, a symmetric homodimer," *Molecular Immunology* 38(14):1029-1037.
Tay et al. (2016) "TriKEs and BiKEs join CARs on the cancer immunotherapy highway," *Human Vaccines & Immunotherapeutics* 12(11):2790-2796.
Vaks et al. (2018) "Design Principles for Bispecific IgGs, Opportunities and Pitfalls of Artificial Disulfide Bonds," *Antibodies* 7(27):1-28.

(56) References Cited

OTHER PUBLICATIONS

Von Strandmann et al. (2006) "A novel bispecific protein (ULBP2-BB4) targeting the NKG2D receptor on natural killer (NK) cells and CD138 activates NK cells and has potent antitumor activity against human multiple myeloma in vitro and in vivo," *Blood* 107(5):1955-1962.
Wang et al. (2016) "A bispecific protein rG7S-MICA recruits natural killer cells and enhances NKG2D-mediated immunosurveillance against hepatocellular carcinoma," *Cancer Letters* 372(2):166-178.
Weiss-Steider et al. (2011) "Expression of MICA, MICB and NKG2D in human leukemic myelomonocytic and cervical cancer cells," *Journal of Experimental & Clinical Cancer Research* 30(1):37.
Written Opinion for International Application No. PCT/US2018/034223 dated Aug. 30, 2018.
Yao et al. (2019) "A VEGFR2-MICA bispecific antibody activates tumor-infiltrating lymphocytes and exhibits potent anti-tumor efficacy in mice," *Cancer Immunology Immunotherapy* 68(9):1429-1441.
Yeap et al. (2016) "CD16 is indispensable for antibody dependent cellular cytotoxicity by human monocytes," *Scientific Reports* 6:34310.
Young et al. (1995) "Thermal stabilization of a single-chain Fv antibody fragment by introduction of a disulphide bond," *FEBS Letters* 377(2):135-139.
U.S. Appl. No. 16/971,104, filed Aug. 19, 2020 Aug. 28, 2020.
Chen X. et al. (2013) "Fusion protein linkers: property, design and functionality" Advanced drug delivery reviews, 65(10):1357-1369.
Colman P. M. (1994) "Effects of amino acid sequence changes on antibody-antigen interactions" Research in Immunology 145(1):33-36.
Dickopf et al. (2020) "Format and geometries matter: Structure-based design defines the functionality of bispecific antibodies," *Computational and Structural Biotechnology Journal* 18:1221-1227.
Junttila et al. (2014) "Antitumor Efficacy of a Bispecific Antibody That Targets HER2 and Activates T Cells," *Cancer Research* 74(19):5561-5571.
Maeda Y. et al. (1997) "Engineering of Functional Chimeric Protein G-Vargula Luciferase" Analytical biochemistry, 249(2):147-152.
Pakula et al. (1989) "Genetic Analysis of Protein Stability and Function," *Annu. Rev. Genet.* 23:289-310.
Roda-Navarro et al. (2020) "Understanding the Spatial Topology of Artificial Immunological Synapses Assembled in T Cell-Redirecting Strategies: A Major Issue in Cancer Immunotherapy," *Frontiers in Cell and Developmental Biology* 7:1-5.
Safdari Y. et al. (2013) "Antibody humanization methods—a review and update" Biotechnology and Genetic Engineering Reviews, 29(2):175-186.
Shen J. et al. (2006) "Single variable domain-IgG fusion: a novel recombinant approach to Fc domain-containing bispecific antibodies" Journal of Biological Chemistry, 281(16): 10706-10714.
Stamova et al. (2011) "Simultaneous engagement of the activatory receptors NKG2D and CD3 for retargeting of effector cells to CD33-positive malignant cells," *Leukemia* 25:1053-1056.
Teplyakov A. et al. (2014) "Antibody modeling assessment II. Structures and models" Proteins: Structure, Function, and Bioinformatics, 82(8):1563-1582.
Torres M. et al. (2008) "The immunoglobulin constant region contributes to affinity and specificity" Trends in immunology, 29(2):91-97.
Xu et al. (2014) "Production of bispecific antibodies in "knobs-into-holes" using a cell-free expression system," mAbs 7(1)231-242.
U.S. Appl. No. 16/486,722, filed Aug. 16, 2019.
Felices et al. (2016) "Generation of BiKEs and TriKEs to Improve NK cell-Mediated Targeting of Tumor Cells," Natural Killer Cells: Methods and Protocols, Methods in Molecular Biology 1441:333-346.
Gantke et al. (2016) "Trispecific Antibodies for Selective CD16A-Directed NK-Cell Engagement in Multiple Myeloma," Blood 128(22):4513.
Gantke et al. (2017) "Trispecific antibodies for CD16A-directed NK cell engagement and dual-targeting of tumor cells," Protein Engineering, Design & Selection 38(9):673-684.
Gauthier et al. (2019) "Multifunctional Natural Killer Cell Engagers Targeting NKp46 Trigger Protective Tumor Immunity," Cell 177(7):1701-1713.
Gooden et al. (2012) "Infiltrating CTLs are bothered by HLA-E on tumors," OncoImmunology, 1(1):92-93.
Kluge et al. (2017) "EGFR/CD16A TandAbs are efficacious NK-cell engagers with favorable biological properties which potently kill EGFR(+) tumors with and without Ras mutation," Cancer Research 77(13 Suppl.):Abstract 3641.
Madlener et al. (2010) "A Bispecific Protein Targeting the NKG2D Receptor on Natural Killer Cells: In Vitro and In Vivo activity of ULBP2-CEA," *Blood* 116(21):2095.
McWilliams, et al. (2016) "Targeting the Tumor Evasion Interaction of NKG2A and Its Ligand HLA-E Increases Natural-Killer Cell Activity in Chronic Lymphocytic Leukemia," Blood 1289-1291.
Myers et al. (2021) "Exploring the NK cell platform for cancer immunotherapy," Nature Reviews Clinical Oncology 18(2):85-100.
Nie et al. (2020) "Biology drives the discovery of bispecific antibodies as innovative therapeutics," Antibody Therapeutics 3(1):18-62.
Rothe et al. (2013) "The Bispecific Immunoligand ULBP2-aCEA Redirects Natural Killer Cells to Tumor Cells and Reveals Potent Anti-Tumor Activity Against Colon Carcinoma," *Int. J. Cancer* 134(12):2829-2840.
Vyas et al. (2016) "Mono- and dual-targeting triplebodies activate natural killer cells and have anti-tumor activity in vitro and in vivo against chronic lymphocytic leukemia," Oncoimmunology 5(9):page e1211220.
Bendayan et al. (1995) "Possibilities of False Immunocytochemical Results Generated by The Use of Monoclonal Antibodies: The Example of the Anti-proinsulin Antibody," *J. Histochem. Cytochem.* 43:881-886.
Bostrom, et al. (2009) "Improving Antibody Binding Affinity and Specificity for Therapeutic Development," *Methods and Protocols* 525:353-376.
Brinkmann et al. (2017) "The making of bispecific antibodies," *MABS* 9(2)182-212.
Bryceson et al. (2006) "Synergy among receptors on resting NK cells for the activation of natural cytotoxicity and cytokine secretion," *Blood* 107(1):159-166.
Chen et al. (1995) "Enhancement and destruction of antibody function by somatic mutation: unequal occurrence is controlled by V gene combinatorial associations," *The EMBO Journal* 14(12):2784-2794.
Choi et al. (2013) "A Heterodimeric Fc-Based Bispecific Antibody Simultaneously Targeting VEGFR-2 and Met Exhibits Potent Anti-tumor Activity," *Mol Cancer Ther*, 12(12):2748-2759.
Davis et al. (1999) "Therapy of B-Cell Lymphoma with Anti-CD20 Antibodies Can Result in the Loss of CD20 Antigen Expression," *Clinical Cancer Research* 5:611-615.
Edwards et al. (2003) "The Remarkable Flexibility of the Human Antibody Repertoire; Isolation of Over One Thousand Different Antibodies to a Single Protein, BLyS," *J. Mol. Biol.* 334:103-118.
Gonzales, et al. (2005) "Minimizing the Immunogenicity of Antibodies for Clinical Application," *Tumour Biol.* 26(1):31-43.
Henry et al. (2017) "Stability-Diversity Tradeoffs Impose Fundamental Constraints on Selection of Synthetic Human $V_H/V_L$ Single-Domain Antibodies from In Vitro Display Libraries," *Frontiers in Immunology*, 8:1-15.
Hoseini et al. (2017) "Acute myeloid leukemia targets for bispecific antibodies," *Blood Cancer Journal* 7(2):e522-e522.
Kennedy et al. (2002) "Incidence and nature of CD20-negative relapses following rituximab therapy in aggressive B-cell non-Hodgkin's lymphoma: a retrospective review," *British Journal of Haematology* 119:412-416.

(56) References Cited

OTHER PUBLICATIONS

Kijanka et al. (2013) "Rapid optical imaging of human breast tumour xenografts using anti-HER2 VHHs site-directly conjugated to IRDye 800CW for image-guided surgery," *Eur J Nucl Med Mol Imaging* 40:1718-1729.
Kim et al. (2014) "Mutational approaches to improve the biophysical properties of human single-domain antibodies," *Biochimica et Biophysica Acta*, 1844:1983-2001.
Koerner et al. (2015) "Induction of NK and T Cell Immune Responses Against Leukemia Cells By Bispecific NKG2D-CD16 and -CD3 Fusion Proteins," *Blood* 126(23):2558, Abstract 606.
Kranz et al. (1981) "Restricted reassociation of heavy and light chains from hapten-specific monoclonal antibodies," *Pro. Natl. Acad. Sci. USA* 78(9):5807-5811.
Krieg et al. (2005) "Functional Analysis of B and T Lymphocyte Attenuator Engagement on CD4+ and CD8+ T Cells," *The Journal of Immunology* 175(10):6420-6427.
Lin et al. (2011) "Improved affinity of a chicken single-chain antibody to avian infectious bronchitis virus by site-directed mutagenesis of complementarity-determining region H3," *African Journal of Biotechnology* 10(79):18294-18302.
Lloyd et al. (2009) "Modelling the human immune response: performance of a 1011 human antibody repertoire against a broad panel of therapeutically relevant antigens," *Protein Engineering, Design and Selection* 22(3):159-168.
Lund et al. (1996) "Multiple interactions of IgG with its core oligosaccharide can modulate recognition by complement and human Fc gamma receptor I and influence the synthesis of its oligosaccharide chains," *J. Immunol* 157:4963-4969.
Maeda et al. (2015) "New antibody modification technology and its application to antibody drugs," Farumashia 51(5):424-428.
Mariuzza et al. (1987) "The Structural Basis of Antigen-Antibody Recognition," *Ann. Rev. Biophys. Chem.* 16:139:59.
McCarthy et al. (2001) "Altering the fine specificity of an anti-Legionella single chain antibody by a single amino acid insertion," *Journal of Immunological Methods* 251:137-149.
Morris "Epitope Mapping of Protein Antigens by Competition ELISA," The Protein Protocols Handbook, Totowa, NJ, Humana Press, (Jan. 1, 1996):595-600.
Paul et al. (1993) "Fundamental Immunology," (textbook) 292-295.
Portolano et al. (1993) "Lack of promiscuity in autoantigen-specific H and L chain combinations as revealed by human H and L chain "roulette, *J. Immunol.* 15(30):880-887.
Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," *Cancer Research* 4 pages.
Schroeder et al. (2010) "Structure and Function of Immunoglobulins," *J Allergy Clin Immunol* 125:S41-S52.
Shum et al. (2002) "Conservation and Variation in Human and Common Chimpanzee CD94 and NKG2 Genes," *The Journal of Immunology* 168:240-252.
Vallera et al. (2016) "IL 15 Trispecific Killer Engagers (TriKE) Make Natural Killer Cells Specific to CD33+ Targets While Also Inducing Persistence, In Vivo Expansion, and Enhanced Function," *Clin Cancer Res*, 22(14):3440-50.
Wang et al. (2018) "IgG Fc engineering to modulate antibody effector functions," *Protein Cell* 9(1):63-73.
Yan et al. (2014) "Construction of a synthetic phage-displayed Nanobody library with CDR3 regions randomized by trinucleotide cassettes for diagnostic applications," *Journal of Translational Medicine* 12:343 (12 pages).
Zhang et al. (2021) "Bispecific antibody-mediated redirection of NKG2D-CAR natural killer cells facilitates dual targeting and enhances antitumor activity," *Journal for ImmunoTherapy of Cancer*; 9:e002980. doi:10.1136/jitc-2021-002980.
U.S. Appl. No. 16/483,330, filed Aug. 2, 2019.
U.S. Appl. No. 16/483,572, filed Aug. 5, 2019.
U.S. Appl. No. 16/484,936, filed Aug. 9, 2019.
U.S. Appl. No. 16/483,788, filed Aug. 6, 2019.
U.S. Appl. No. 16/486,921, filed Aug. 19, 2019.
U.S. Appl. No. 16/486,569, filed Aug. 16, 2019.
U.S. Appl. No. 16/486,570, filed Aug. 16, 2019.
U.S. Appl. No. 16/488,395, filed Aug. 23, 2019.
U.S. Appl. No. 17/095,238, filed Nov. 11, 2020.
U.S. Appl. No. 16/615,203, filed Nov. 20, 2019.
U.S. Appl. No. 16/615,231, filed Nov. 20, 2019.
U.S. Appl. No. 16/635,079, filed Jan. 29, 2020.
U.S. Appl. No. 16/638,559, filed Feb. 12, 2020.
U.S. Appl. No. 17/188,978, filed Mar. 1, 2021.
U.S. Appl. No. 16/639,150, filed Feb. 14, 2020.
U.S. Appl. No. 16/644,585, filed Mar. 5, 2020.
U.S. Appl. No. 17/190,155, filed Mar. 2, 2021.
U.S. Appl. No. 16/645,613, filed Mar. 9, 2020.
U.S. Appl. No. 16/967,216, filed Aug. 4, 2020.
U.S. Appl. No. 17/058,335, filed Nov. 24, 2020.
U.S. Appl. No. 16/971,098, filed Aug. 19, 2020.
U.S. Appl. No. 16/967,218, filed Aug. 4, 2020.
U.S. Appl. No. 17/045,015, filed Oct. 2, 2020.
U.S. Appl. No. 17/045,016, filed Oct. 2, 2020.
U.S. Appl. No. 17/053,558, filed Nov. 6, 2020.
U.S. Appl. No. 17/055,792, filed Nov. 16, 2020.
U.S. Appl. No. 17/265,876, filed Feb. 4, 2021.
U.S. Appl. No. 17/266,349, filed Feb. 5, 2021.
U.S. Appl. No. 17/543,628, filed Dec. 6, 2021.
U.S. Appl. No. 17/265,879, filed Feb. 4, 2021.
U.S. Appl. No. 17/266,966, filed Feb. 8, 2021.
U.S. Appl. No. 16/971,104, filed Aug. 19, 2020.
U.S. Appl. No. 17/736,031, filed May 3, 2022.
U.S. Appl. No. 17/682,367, filed Feb. 28, 2022.
U.S. Appl. No. 17/308,691, filed May 5, 2021.
U.S. Appl. No. 17/686,238, filed Mar. 3, 2022.
Berenbaum (1977) "Synergy, additivism and antagonism in immunosuppression," *Clin. Exp. Immunol.* 28:1-18.
Berenbaum (1989) "What is Synergy?" *Pharmacological Reviews* 41:93-141.
Bost et al. (1988) "Antibodies Against a Peptide Sequence Within the HIV Envelope Protein Crossreacts with Human Interleukin-2," *Immunological Investigations* 17(6&7):577-586.
Branca et al. (2018) "Nature Biotechnology's academic spinouts of 2017," *Nature Biotechnology* 36(4):297-306.
Bruhns et al. (2009) "Specificity and affinity of human FCγ receptors and their polymorphic variants for human IgG subclasses," *Blood* 113(16):3716-3724.
Goel et al. (2004) "Plasticity within the Antigen-Combining Site May Manifest as Molecular Mimicry in the Humoral Immune Response," *The Journal of Immunology* 173(12):7358-7367.
Janeway et al. (1997) Chapter 3, Structure of the Antibody Molecule and Immunoglobulin Genes, *Immunology Third Edition, Garland Publishing Inc.*, 3:1-3:11.
Kanyavuz et al. (2019) "Breaking the law: unconventional strategies for antibody diversification," *Nature Reviews Immunology* 19(6):355-368.
Kjellev et al. (2007) "Inhibition of NKG2D receptor function by antibody therapy attenuates transfer-induced colitis in SCID mice," *Eur. J. Immunol.* 37:1397-1406.
Piche-Nicholas et al. (2018) "Changes in complementarity-determining regions significantly alter IgG binding to the neonatal Fc receptor (FcRn) and pharmacokinetics," *MABS* 10(1)81-94.
Roell et al. (2017) "An Introduction to Terminology and Methoodology of Chemical Synergy—Perspectives from Across Disciplines," *Frontiers in Pharmacology: Cancer Molecular Targets and Therapeutics* 8:1-11.
Tallarida (2000) "Drug Synergism and Dose Effect Analysis," *Ed. Chapman & Hall* pp. 1-71.
Wensveen et al. (2018) "NKG2D: A Master Regulator of Immune Cell Responsiveness," *Frontiers in Immunology* 9(Article 411):8 pages.
Affimed, Affimed Enters Into Collaboration With Merck to Evaluate AFM13 in Combination With . . . Retreived < URL:https ://www. affimed.com/affi med-enters-into-collaboration-with-merck-to-

(56) References Cited

OTHER PUBLICATIONS evaluate-afm 13-i n-combination-with-keytruda-pembrolizumab-for-patients-with-hodgkin-lymphoma/>[retrieved on Feb. 1, 2023] Jan. 25, 2016.
Akbar et al., 2021, "A compact vocabulary of paratope-epitope interactions enables predictability of antibody-antigen binding," *Cell Reports*, 34:108856 21 pages.
Altshuler et al., 2010, "Generation of Recombinant Antibodies and Means for Increasing Their Affinity," *Biochemistry* (Moscow), 75(13):1584-1605.
Atwell et al., 1997, "Stable heterodimers from remodeling the domain interface of a homodimer using a phage display library", J. Mol. Biol., 270(1):26-35.
Baek et al., 2014, "Construction of a large synthetic human Fab antibody library on yeast cell surface by optimized yeast mating", Journal of Microbiology and Biotechnology, 24(3):408-420.
Boltz, 2011, "Bi-specific Aptamers mediating Tumour Cell Lysis," Dissertation, M.Sc. Molekulare Biotechnologie, Technische Universität Darmstadt, pp. 1-133.
Bowen et al., 2016, "Revisiting the Immunoglobulin Intramolecular Signaling Hypothesis," *Trends Immunol*., 37(11):721-723.
Brown, et al., 1996, "Tolerance of single, but not multiple, amino acid replacements in antibody VH CDR 2: a means of minimizing B cell wastage from somatic hypermutation?," Journal of Immunology, 156: 3285-3291.
Chan et al., 2010, "Therapeutic antibodies for autoimmunity and inflammation," Nature Reviews 10:301-316.
Chen et al., 2017, "Targeting FLT3 by chimeric antigen receptor T ccells for the treatment of acute myeloid leuikemia", Leukemia, 31(8): 1830-1834.
Choi et al., 2015, "Engineering of immunoglobin Fc heterodimers using yeast surface-displayed combinatorial Fc library screening", PloS One, vol. 10, article No. 30145349:1-20.
Choi et al., 2015, "Crystal structures of immunoglobulin Fc heterodimers reveal the molecular basis for heterodimer formation," Molecular Immunology 65(2):377-83.
Cunningham et al., 1969, "Subgroups of Amino Acid Sequences in the Variable Regions of Immunoglobulin Heavy Chains," Proc Natl Acad Sci USA 64(3):997-1003.
Dahlberg et al., 2015, "Natural Killer Cell-Based Therapies Targeting Cancer: Possible Strategies to Gain and sustain Anti-Tumor Activity" Frontiers In Immunology 6(Article 605): 19 pages.
Davis et al., 2010, "SEEDbodies: Fusion Proteins Based on Strand-Exchange Engineered Domain (Seed) CH3 Heterodimers in an Fe Analogue Platform for Asymmetric Binders or Immunofusions and Bispecific Antibodies," Protein Eng Des Sel 23(4):195-202.
Doppalapudi et al., 2010, "Chemical generation of bispecific antibodies," PNAS, 107(52):22611-22616.
El-Amine et al., 2002, "In vivo induction of tolerance by an Ig peptide is not affected by the deletion of FcR or a mutated IgG Fc fragment," *International Immunology* , 14(7):761-766.
Elliott et al., 2014, "Antiparallel conformation of knob and hole aglycosylated half-antibody homodimers is mediated by a CH2-CH3 hydrophobic interaction", J. Mol. Biol., 426(9):1947-57.
Epling-Burnette et al., 2004, "Dysregulated NK receptor expression in patients with lymphoproliferative disease of granular lymphocytes", Blood, 13(9):3431-3439.
Extended European Search Report dated Mar. 18, 2021 for EP App. No. 18840650.8 (14247-472-227).
Farumashia, 2015, Journal of the Pharmaceutical Society of Japan, 51(5), pp. 424-428.
Feng et al., 2011, "Design, Expression and Characterization of a Soluble Single-Chain Functional Human Neonatal Fe Receptor," Protein Expr Purif 79(1):66-71.
Germain et al., 2008, "Redirecting NK cells mediated tumor cell lysis by a new recombinant bifunctional protein," *Protein Engineering, Design & Selection* , 21(11):665-672.
Gunasekaran et al., 2010, "Enhancing Antibody Fe Heterodimer Formation through Electrostatic Steering Effects: Applications to Bispecific Molecules and Monovalent IgG," J Biol Chem 285(25):19637-46.
Hasegawa et al., 2017, "Single amino acid substitution in LC-CDR1 induces Russell body phenotype that attenuates cellular protein synthesis through elF2a phosphorylation and thereby downregulates IgG secretion despite operational secretory pathway traffic," *MABS* , 9(5):854-873.
Henry et al., 2004, "A Prostate-Specific Membrane Antigen-Targeted Monoclonal Antibody-Chemotherapeutic Conjugate Designed for the Treatment of Prostate Cancer," Cancer Research, 64:7995-8001.
Hlavacek et al., 1999, "Steric Effects on Multivalent Ligand-Receptor Binding: Exclusion of Ligand Sites by Bound Cell Surface Receptors," Biophysical Journal, 76(6): 3031-3043.
Holliger et al., 2005, "Engineered antibody fragments and the rise of single domains," Nat Biotechnol 23(9): 1126-36.
Jonnalagadda et al., 2015, "Chimeric Antigen Receptors With Mutated IgG4 Fc Spacer Avoid Fc Receptor Binding and Improve T Cell Persistence and Antitumor Efficacy," *Molecular Therapy*, 23(4):757-768.
Kaur et al., 2015, "Applications of In Vitro- In Vivo Correlations in Generic Drug Development: Case Studies," *The AAPS Journal* , 17(4): 1035-1039; doi: 10.1208/s12248-015-9765-1.
Klein et al., 2012, "Progress in overcoming the chain association issue in bispecific; heterodimeric IgG antibodies," MaBs 4(6):653-663.
Kunik et al., 2012, "Structural consensus among antibodies defines the antigen binding site," PLoS Comput Biol., 8(2):e1002388. Epub Feb. 23, 2012.
Lewis et al., 2014, "Generation of bispecific IgG antibodies by structure-based design of an orthogonal Fab interface", Nat. Biotechnol., 32(2):198-198.
Lippow et al., 2007, "Computational design of antibody-affinity improvement beyond in vivo maturation," *Nature Biotechnology* , 25(10):1171-1176.
Lo et al., 2021 "Conformational epitope matching and prediction based on protein surface spiral features," *BMC Genomics* , 22(Suppl 2): 116 16 pages.
Mandelboim et al., 1999, "Human CD16 as a lysis receptor mediating direct natural killer cell cytotoxicity," *PNAS USA* , 96(10):5640-5644; doi: 10.1073/pnas.96.10.5640.
Marks et al., 2020, "How repertoire data are changing antibody science," *J. Biol. Chem*., 295(29):9823-9837.
Mejstrikova et al., 2017, "CD19-negative relapse of pediatric B-cell precursor acute lymphoblastic leukemia following blinatumomab treatment," Blood Cancer Journal, Dec. 20(7): s41408-017-023.
Merchant et al., 1998, "An efficient route to human bispecific IgG," Nature Biotechnology 16, 677-681 doi : 10.1038/nbt0798-677.
Miller et al., 2003, "Design, Construction, and in Vitro Analyses of Multivalent Antibodies," J Immunol 170(9):4854-61.
Mimoto et al., 2014, "Crystal structure of a novel asymmetrically engineered Fc variant with improved affinity for FcγRs", Mol. Immunol., 58(1):132-138.
Moore et al., 2011, "A novel bispecific antibody format enables simultaneous bivalent and monovalent co-engagement of distinct target antigens," mAbs 3:6, 546-557; Nov./Dec. 2011, Landes Bioscience, DOI: 10.4161/mabs.3.6.18123.
Muda et al., 2011, "Therapeutic assessment of SEED: a new engineered antibody platform designed to generate mono- and bispecific antibodies", Protein Eng. Des. Sel., 24(5):447-454.
Muller et al., 2015, "Trastuzumab emtansine (T-DM1) renders HER2+ breast cancer highly susceptible to CTLA-4/PD-1 blockade," Sci. Transl. Med., 7(315):1-14.
Muntasell et al., 2017, "Targeting NK-cell checkpoints for cancer immunotherapy," Current Opinion in Immunology 45:73-81.
Notice of Opposition for Colombia Patent Application No. NC2020/0010345 dated Dec. 16, 2020.
Parsons et al., 2016, "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089-1096.

(56) References Cited

OTHER PUBLICATIONS

Rabia et al., 2018, "Understanding and overcoming trade-offs between antibody affinity, specificity, stability and solubility" Biochem Eng J., 137:365-374.
Raulet, 2003, "Roles of the NKG2D immunoreceptor and its ligands," *Nature: Reviews Immunology*, 3:781-790; doi: 10.1038/nri1199.
Ridgway et al., 1996, "Knobs-into-Holes' engineering of antibody Ch3 domains for heavy chain heterodimerization," Protein Engineering 9(7):617-21.
Rosano et al., 2014, "Recombinant protein expression in *Escherichia coli*: advances and challenges" Frontiers in Microbiology, 5(172):17 pages.
Roskopf, et al., 2016, "Dual-targeting triplebody 33-3-19 mediates selective lyssi of biphenotypic CD19+ CD33+ leukemia cells," Oncotarget, 7(6): 22579-22589.
Sazinsky et al., 2008, "Aglycosylated immunoglobulin $G_1$ variants productively engage activating Fc receptors," *Proceedings of the National Academy of Sciences* , 105(51)20167-20172.
Schmitz et al., 2001, "Pharmacogenomics: implications for laboratory medicine," Clinica Chimica Acta 308:43-53.
Singer et al., 1998, "Genes and Genomes," Moscow, "Mir" 1:63-64.
Sondermann et al., 2000, "The 3.2-Å crystal structure of the human IgG1 Fc fragment-FcγRIII complex," Nature, 406(6793):267-273.
Strop et al., 2012, "Generating Bispecific Human IgG1 and IgG2 Antibodies from Any Antibody Pair," J Mol Biol 420:204-19.
Sulea et al., 2018, "Application of Assisted Design of Antibody and Protein Therapeutics (ADAPT) improves efficacy of a *Clostridium difficile* toxin A single-domain antibody," 8:2260, 11 pages.
Thakur et al., 2018, "Bispecific antibody based therapeutics: Strengths and challenges," Blood Review, 32:339-347.
Vajda et al., 2021, "Progress toward improved understanding of antibody maturation," *Current Opinion in Structural Biology* , 67:226-231.
Von Kreudenstein et al., 2013, "Improving Biophysical Properties of a Bispecific Antibody Scaffold to Aid Developability: Quality by Molecular Design," mAbs 5(5):646-54.
Von Kreudenstein et al., 2014, "Protein Engineering and the Use of Molecular Modeling and Simulation: The Case of Heterodimeric Fe Engineering," Methods 65(1):77-94.
Ward et al., 1989, "Binding activities of a epertoire of single immunoglobulin variable domains secreted from *Escherichia coli,*" *Nature* , 341:544-546.
Wark et al., 2006, "Latest technologies for the enhancement of antibody affinity", *Advanced Drug Delivery Reviews*, 58(5-6):657-670.
Wikipedia: "Trifunctional antibody Feb. 1, 2018",, Jan. 2, 2018 (Jan. 2, 2018), pp. 1-4, XP093016568, Retrieved from the Internet: URL:https://en.wikipedia.org/w/index.php?title=Trifunctional antibody8 oldid=818265015.
Wranik et al., 2012, "LUZ-Y, a novel platform for the mammalian cell production of full-length IgG-bispecific antibodies", J. Biol. Chem., 287:43331-43339.
Written Opinion for International Application No. PCT/US2018/017470 dated Apr. 24, 2018.
Written Opinion for International Application No. PCT/US2019/017330 dated Jun. 11, 2019.
Written Opinion for International Application No. PCT/US2019/018751 dated Jul. 1, 2019.
Xie et al., 2005, "A new format of bispecific antibody: highly efficient heterodimerization, expression and tumor cell lysis," J Immunol Methods 296(1):95-101.
Xu et al., 2019, "A VEGFR2-MICA bispecific antibody activates tumor-infiltrating lymphocytes and exhibits potent anti-tumor efficacy in mice," Cancer Immunology Immunotherapty, 68(9): 1429-1441.
Bogen et al., 2021, "Design of a Trispecific Checkpoint Inhibitor and Natural Killer Cell Engager Based on a 2 + 1 Common Light Chain Antibody Architecture," Frontiers in Immunology 12:16 pages.
Briney et al., 2019, "Commonality despite exceptional diversity in the baseline human antibody repertoire," Nature 566:393 (19 pages).
Dasgupta et al., 2005, "Inhibition of NK Cell Activity through TGF-b1 by Down-Regulation of NKG2D in a Murine Model of Head and Neck Cancer," J Immunol 175(8):5541-5550.
Demaria et al., 2021, "Natural killer cell engagers in cancer immunotherapy: Next generation of immuno-oncology treatments, " Eur. J. Immunol. 51:1934-1942.
Giuliani et al., 2017, "Activation of NK cells and disruption of PD-L1/PD-1 axis: two different ways for lenalidomide to block myeloma progression," Oncotarget 8(14):24031-24044.
Hilpert et al., 2012, "Comprehensive analysis of NKG2D ligand expression and release in leukemia: implications for NKG2D-mediated NK cell responses," J. Immunol., 189(3): 1360-1371.
Katano et al., 2015, "Predominant Development of Mature and Functional Human NK Cells in a Novel Human IL-2-Producing Transgenic NOG Mouse" J. Immunol. 194(7):3513-3525.
Khan et al., 2014, "Adjustable Locks and Flexible Keys: Plasticity of Epitope-Paratope Interactions in Germline Antibodies," J. Immunol 192:5398-5405.
Langer, 1990, "New Methods of Drug Delivery," Science, 249(4976):1527-1533.
Mendoza Rincón, 2014, "The NKG2D receptor in the border of immune surveillance and carcinogenesis," Publicación Científica en Ciencias Biomédicas 2(21):37-43. (English Abstract).
Miller et al., 2018, "Annual Review of Cancer Biology Natural Killer Cells in Cancer Immunotherapy," Annu. Rev. Cancer Biol. 8(3):77-103.
Miller et al.,. 2019, "Natural Killer Cells in Cancer Immunotherapy," Ann. Rev. Cancer Biol. 3:77-103.
Poosaria et al., 2017, "Computational de novo Design of Antibodies binding to a Peptide with High Affinity," 114(6):1331-1342.
Spiess et al., 2015, "Alternative molecular formats and therapeutic applications for bispecific antibodies," Molecular Immunology 67:95-106.
Vidarsson et al., 2014, "IgG subclasses and allotypes: from structure to effector functions," Front. Immunol. 5:520.
Watanabe et al., 2014, NKG2D functions as an activating receptor on natural killer cells in the common marmoset (*Callithrix jacchus*), Int. Immunol., 26(11): 597-606.
Watzl et al., 2010, "Signal Transduction During Activation and Inhibition of Natural Killer Cells", Curr Protoc Immunol., 90(1):11.9B1-11.9B.17.
Whalen et al., 2023, "Engaging natural killer cells for cancer therapy via NKG2D, CD16A and other receptors," 15(1) 15 pages.
Xie et al., 2015, "VEGFR2 targeted antibody fused with MICA stimultes NKG2D mediated immunosurveillance and exhibits potent anti-tumor activity against breast cancer," Oncotarget 7(13):16455-16471.
Yang et al., 2016, "Bispecific Antibodies as a Development Platform for New Concepts and Treatment Strategies" Int. J. Mol. Sci. 18(48) 21 pages.
Yang et al., 2017, "Enhancing NK cell-mediated cytotoxicity to cisplatin-resistant lung cancer cells via MEK/Erk signaling inhibition," Nature Scientific Reports, 7:7958 (13 pages).
Zhou et al., 1995, "Characterization of human homologue of 4-1BB and its ligand," Immunology Letters 45:67-73.
Absolute Antibody, 2023, Anti-NKG2D [ADI-27749 (A49)] Standard Size Ab03079-3.0, 1 page.
Bartlett et al., 2007, "Lenalidomide and pomalidomide strongly enhance tumor cell killing in vitro during antibody-dependent cellular cytotoxicity (ADCC) mediated by trastuzumab, cetuximab and rituximab," American Society of Clinical Oncology, 25(18S).
Bryceson et al., 2006, "Activation, coactivation, and costimulation of resting human natural killer cells," Immunological Reviews, 214:73-91.
Davis et al., 2017, "Natural killer cells unleashed: Checkpoint receptor blockade and BiKE/TriKE utilization in NK-mediated anti-tumor immunotherapy," Seminars in Immunology, 31:64-75.
Eruslanov et al., 2013, "Expansion of CCR8+ Inflammatory Myeloid Cells in Cancer Patients with Urothelial and Renal Carcinomas," Clinical Cancer Research 19(7):1670-1680.

(56) References Cited

OTHER PUBLICATIONS

Kim et al., 1995 "Evidence That the Hinge Region Plays a Role in Maintaining Serum Levels of the Murine IgG1 Molecule," Molecular Immunology 32(7):467-475.
Liu et al., 2020, "Fc-Engineering for Modulated Effector Functions-Improving Antibodies for Cancer Treatment," Antibodies, 9(64):34 pages.
Nersesian et al., 2020, "N K cell infiltration is associated with improved overall survival in solid cancers: A systematic review and meta-analysis," Translational Oncology 14 (20 pages).
Novus Biologicals, 2015, "CD-16: Find me on macrophages, neutrophils and NK cells," https://www.novusbio.com/antibody-news/antibodies/cd16-find-me-on-macrophages-neutrophils-and-nk-cells.
Plitas et al., 2016, "Regulatory T Cells Exhibit Distinct Features in Human Breast Cancer," Immunity 45(5):1122-1134.
Raynaud et al., 2021, "Anti-NKG2D single domain-based antibodies for the modulation of anti-tumor immune response," Oncoimmunology 10(1):e1854529-1-e1854529-14.
Stallard, 2016, "New Approach Could Boost Immunotherapy for Breast Cancer," Memorial Sloan Kettering Cancer Center 1-5.
Weatherill et al., 2012, "Towards a universal disulphide stabilised single chain Fv format: importance of interchain disulphide bond location and vL-vH orientation," Protein Engineering, Design, and Selection, 25(7):321-329.
Wu et al., 2011, "Lenalidomide enhances antibody-dependent cellular cytotoxicity of solid tumor cells in vitro: influence of host immune and tumor markers," Cancer Immunology, Immunotherapy, Springer, 60(1): 61-73.
Billadeau et al. (2003) NKG2D-DAP10 triggers human NK cell-mediated killing via a Syk-independent regulatory pathway, Nature Immunology 4(6):557-64.
Feng et al., (2020) "NKG2D-Fc fusion protein promotes antitumor immunity through the depletion of immunosuppressive cells," Cancer Immunol. Immunother. 69(10):2147-2155.
Hale (2024) "Living in LALA land? Forty years of attenuating Fc effector functions," Immunol. Rev. 328(1):422-37.
Herold et al. (2017) "Determinants of the assembly and function of antibody variable domains," Scientific Reports, 7:12276.
Ho et al. (2002) "Costimulation of multiple NK cell activation receptors by NKG2D," Journal of Immunology 169(7):3667-3675.
Kellner et al. (2011) "Heterodimeric bispecific antibody-derivatives against CD19 and CD16 induce effective antibody-dependent cellular cytotoxicity against B-lymphoid tumor cells ," Cancer Lett. 303(2):128-39.
Kontermann et al. (2015) "Bispecific antibodies," Drug Discovery Today 20(7):838-847 (12 pages).
Long et al. (2013) "Controlling NK Cell Responses: Integration of Signals for Activation and Inhibition," Annu Rev Immunol. 2013 ; 31: 10.1146/annurev-immunol-020711-075005.
Maelig et al. (2016) "NK cells and cancer: you can teach innate cells new tricks", Nature Reviews Cancer, 16(1):7-19.
Middelburg et al. (2021) "Overcoming Challenges for CD3-Bispecific Antibody Therapy in Solid Tumors," Cancers 13(2):287 (25 pages).
Muyldermans (2013) "Nanobodies: Natural Single-Domain Antibodies," Annual Review of Biochemistry 82(1):775-797.
Trivedi et al. (2017) "Clinical pharmacology and translational aspects of bispecific antibodies," Clin. Transl. Sci. 10:147-162.
Van de Winkel et al. (1993) "Human IgG Fc receptor heterogeneity: molecular aspects and clinical implications," Immunology Today 14(5):215-221.

* cited by examiner

PROTEINS BINDING NKG2D, CD16 AND A TUMOR-ASSOCIATED ANTIGEN

CROSS-REFERENCE TO RELATED APPLICATIONS

This application is a U.S. national stage application, filed under 35 U.S.C. § 371, of International Application No. PCT/US2018/034223, filed on May 23, 2018, which claims the benefit of and priority to U.S. Provisional Patent Application No. 62/510,173, filed on May 23, 2017; U.S. Provisional Patent Application No. 62/539,396, filed on Jul. 31, 2017; U.S. Provisional Patent Application No. 62/539,416, filed on Jul. 31, 2017; U.S. Provisional Patent Application No. 62/539,419, filed on Jul. 31, 2017; U.S. Provisional Patent Application No. 62/546,292, filed on Aug. 16, 2017; U.S. Provisional Patent Application No. 62/546,296, filed on Aug. 16, 2017; and U.S. Provisional Patent Application No. 62/552,146, filed on Aug. 30, 2017, the entire contents of each of which are hereby incorporated by reference in their entireties for all purposes.

SEQUENCE LISTING

The instant application contains a Sequence Listing which has been submitted electronically in ASCII format and is hereby incorporated by reference in its entirety. Said ASCII copy, created on May 21, 2018, is named DFY-022WO.txt and is 212 kb in size.

FIELD OF THE INVENTION

The invention relates to multi-specific binding proteins that bind to NKG2D, CD16, and a tumor-associated antigen selected from CD37, CD20, CD19, CD22, CD30, CD52, and CD133.

BACKGROUND

Cancer continues to be a significant health problem despite the substantial research efforts and scientific advances reported in the literature for treating this disease. Blood and bone marrow cancers are frequently diagnosed cancer types, including multiple myelomas, leukemia, and lymphomas. Current treatment options for these cancers are not effective for all patients and/or can have substantial adverse side effects. Other types of cancer also remain challenging to treat using existing therapeutic options.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. Antibodies that bind to certain tumor-associated antigens and to certain immune cells have been described in the literature. See, e.g., WO 2016/134371 and WO 2015/095412.

Natural killer (NK) cells are a component of the innate immune system and make up approximately 15% of circulating lymphocytes. NK cells infiltrate virtually all tissues and were originally characterized by their ability to kill tumor cells effectively without the need for prior sensitization. Activated NK cells kill target cells by means similar to cytotoxic T cells—i.e., via cytolytic granules that contain perforin and granzymes as well as via death receptor pathways. Activated NK cells also secrete inflammatory cytokines such as IFN-γ and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter foreign cells or cancer cells, they are activated via their activating receptors (e.g., NKG2D, NCRs, DNAM1). NK cells are also activated by the constant region of some immunoglobulins through CD16 receptors on their surface. The overall sensitivity of NK cells to activation depends on the sum of stimulatory and inhibitory signals.

CD37, a member of the tetraspanin superfamily of cell surface antigens, is expressed on virtually all mature B lymphocytes, but not on pro-B or plasma cells. It is a lineage-specific B-cell antigen, and is absent or minimally expressed on normal T cells, thymocytes, monocytes, granulocytes, platelets, natural killer (NK) cells, and erythrocytes. In addition, CD37 is expressed on malignancies derived from peripheral mature B cells, such as B-cell chronic lymphocytic leukemia (CLL), hairy-cell leukemia (HCL), non-Hodgkin lymphoma, and acute myeloid leukemia.

CD20 is an activated-glycosylated phosphoprotein expressed on the B cell surface during B cell differentiation from the pro-B cell phase until maturity. It plays a role in the development and differentiation of B-cells into plasma cells. CD20 is also found on chronic lymphocytic leukemia, non-Hodgkin's lymphoma, follicular lymphoma, and B-cell malignancies.

CD19 is a transmembrane glycoprotein expressed on the surface of B lymphocytes from earliest recognizable B-lineage cells during development to B-cell blasts. It primarily acts as a B cell co-receptor in conjunction with CD21 and CD81. CD19 is expressed in many cancers, such as chronic lymphocytic leukemia, non-Hodgkin's lymphoma, follicular lymphoma, acute lymphoblastic leukemia, multiple myeloma, B-cell malignancies, and acute myeloid leukemia.

CD22, a B-cell-restricted phosphoglycoprotein is expressed on the surface of mature B cells and to a lesser extent on some immature B cells. It functions as an inhibitory receptor for B cell receptor (BCR) signaling. In addition, CD22 is expressed in cancer cells, such as chronic lymphocytic leukemia, non-Hodgkin's lymphoma, follicular lymphoma, acute lymphoblastic leukemia, B cell malignancies, and hairy cell leukemia.

CD30 is a member of the tumor necrosis factor receptor (TNFR) superfamily, specifically TNFR8. CD30 is expressed on activated lymphocytes and a few other normal cells. Its signaling activates the NF-κB transcription factor, resulting in pleiotropic regulation of gene function. CD30 is the characteristic marker of classical Hodgkin's lymphoma, anaplastic large-cell lymphoma, and embryonal cell carcinoma, and it is expressed on a subset of aggressive T- and B-cell neoplasms. Its restricted expression on normal cells makes it an attractive candidate for targeted therapy.

CAMPATH-1, also known as cluster of differentiation 52 (CD52), is a peptide of 12 amino acids, anchored to glycosylphosphatidylinositol (GPI). CD52 is expressed on the cell membrane of mature B and T lymphocytes, monocytes, and dendritic cells but not on the stem cells from which these lymphocytes were derived. Further, CD52 is found within the male genital tract and is present on the surface of mature sperm cells. CD52 is associated with certain types of cancers, including chronic lymphocytic leukemia (CLL), cutaneous T-cell lymphoma, peripheral T-cell lymphoma and T-cell prolymphocytic leukemia, B cell malignancies, non- Hodgkin's lymphoma, Hodgkin's lymphoma, anaplastic large cell lymphoma, adult T-cell leukemia-lymphoma, mature T/natural killer (NK) cell neoplasms, and thymoma.

CD133 is a pentaspan transmembrane glycoprotein primarily identified in human hematopoietic stem and progenitor cells. Currently, the physiologic role of this surface receptor remains unclear. However, CD133 was identified as a marker for cancer stem cells in various carcinomas including breast, colon, prostate, liver, pancreatic, lung, ovarian, renal, uterine and testicular germ cell cancer, acute myeloid leukemia, acute lymphoblastic leukemia, glioma, glioblastoma and head and neck squamous cell carcinoma. CD133 can interact with p85 to activate PI3K/AKT/mTOR-signaling pathways in cancer stem cells, and this activation consequently provokes cancer stem cells to promote tumorigenic capacity.

SUMMARY

The invention provides multi-specific binding proteins that bind to the NKG2D receptor and CD16 receptor on natural killer cells, and a tumor-associated antigen selected from CD37, CD20, CD19, CD22, CD30, CD52, and CD133. Such proteins can engage more than one kind of NK-activating receptor, and may block the binding of natural ligands to NKG2D. In certain embodiments, the proteins can agonize NK cells in humans. In some embodiments, the proteins can agonize NK cells in humans and in other species such as rodents and cynomolgus monkeys. Various aspects and embodiments of the invention are described in further detail below.

Accordingly, one aspect of the invention provides a protein that incorporates a first antigen-binding site that binds NKG2D; a second antigen-binding site that binds a tumor-associated antigen selected from CD37, CD20, CD19, CD22, CD30, CD52, and CD133; and an antibody Fc domain, a portion thereof sufficient to bind CD16, or a third antigen-binding site that binds CD16.

The antigen-binding sites may each incorporate an antibody heavy chain variable domain and an antibody light chain variable domain (e.g., arranged as in an antibody, or fused together to from an scFv), or one or more of the antigen-binding sites may be a single domain antibody, such as a $V_HH$ antibody like a camelid antibody or a $V_{NAR}$ antibody like those found in cartilaginous fish.

In one aspect, the present invention provides multi-specific binding proteins that bind to the NKG2D receptor and CD16 receptor on natural killer cells, and a tumor-associated antigen selected from CD37, CD20, CD19, CD22, CD30, CD52, and CD133. The NKG2D-binding site includes a heavy chain variable domain at least 90% identical to an amino acid sequence selected from: SEQ ID NO:1, SEQ ID NO:41, SEQ ID NO:49, SEQ ID NO:57, SEQ ID NO:59, SEQ ID NO:61, SEQ ID NO:69, SEQ ID NO:77, SEQ ID NO:85, and SEQ ID NO:93.

The first antigen-binding site, which binds to NKG2D, in some embodiments, can incorporate a heavy chain variable domain related to SEQ ID NO:1, such as by having an amino acid sequence at least 90% (e.g., 90%, 91%, 92%, 93%, 94%, 95%, 96%, 97%, 98%, 99%, or 100%) identical to SEQ ID NO:1, and/or incorporating amino acid sequences identical to the CDR1 (SEQ ID NO:105), CDR2 (SEQ ID NO:106), and CDR3 (SEQ ID NO:107) sequences of SEQ ID NO:1. The heavy chain variable domain related to SEQ ID NO:1 can be coupled with a variety of light chain variable domains to form an NKG2D binding site. For example, the first antigen-binding site that incorporates a heavy chain variable domain related to SEQ ID NO:1 can further incorporate a light chain variable domain selected from any one of the sequences related to SEQ ID NOs:2, 4, 6, 8, 10, 12, 14, 16, 18, 20, 22, 24, 26, 28, 30, 32, 34, 36, and 40. For example, the first antigen-binding site incorporates a heavy chain variable domain with amino acid sequences at least 90% (e.g., 90%, 91%, 92%, 93%, 94%, 95%, 96%, 97%, 98%, 99%, or 100%) identical to SEQ ID NO:1 and a light chain variable domain with amino acid sequences at least 90% (e.g., 90%, 91%, 92%, 93%, 94%, 95%, 96%, 97%, 98%, 99%, or 100%) identical to any one of the sequences selected from SEQ ID NOs:2, 4, 6, 8, 10, 12, 14, 16, 18, 20, 22, 24, 26, 28, 30, 32, 34, 36, and 40.

Alternatively, the first antigen-binding site can incorporate a heavy chain variable domain related to SEQ ID NO:41 and a light chain variable domain related to SEQ ID NO:42. For example, the heavy chain variable domain of the first antigen binding site can be at least 90% (e.g., 90%, 91%, 92%, 93%, 94%, 95%, 96%, 97%, 98%, 99%, or 100%) identical to SEQ ID NO:41, and/or incorporate amino acid sequences identical to the CDR1 (SEQ ID NO:43), CDR2 (SEQ ID NO:44), and CDR3 (SEQ ID NO:45) sequences of SEQ ID NO:41. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:42, and/or incorporate amino acid sequences identical to the CDR1 (SEQ ID NO:46), CDR2 (SEQ ID NO:47), and CDR3 (SEQ ID NO:48) sequences of SEQ ID NO:42.

In other embodiments, the first antigen-binding site can incorporate a heavy chain variable domain related to SEQ ID NO:49 and a light chain variable domain related to SEQ ID NO:50. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:49, and/or incorporate amino acid sequences identical to the CDR1 (SEQ ID NO:51), CDR2 (SEQ ID NO:52), and CDR3 (SEQ ID NO:53) sequences of SEQ ID NO:49. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:50, and/or incorporate amino acid sequences identical to the CDR1 (SEQ ID NO:54), CDR2 (SEQ ID NO:55), and CDR3 (SEQ ID NO:56) sequences of SEQ ID NO:50.

Alternatively, the first antigen-binding site can incorporate a heavy chain variable domain related to SEQ ID NO:57 and a light chain variable domain related to SEQ ID NO:58, such as by having amino acid sequences at least 90% (e.g., 90%, 91%, 92%, 93%, 94%, 95%, 96%, 97%, 98%, 99%, or 100%) identical to SEQ ID NO:57 and at least 90% (e.g., 90%, 91%, 92%, 93%, 94%, 95%, 96%, 97%, 98%, 99%, or 100%) identical to SEQ ID NO:58, respectively.

In another embodiment, the first antigen-binding site can incorporate a heavy chain variable domain related to SEQ ID NO:59 and a light chain variable domain related to SEQ ID NO:60, For example, the heavy chain variable domain of the first antigen binding site can be at least 90% (e.g., 90%, 91%, 92%, 93%, 94%, 95%, 96%, 97%, 98%, 99%, or 100%) identical to SEQ ID NO:59, and/or incorporate amino acid sequences identical to the CDR1 (SEQ ID NO:324), CDR2 (SEQ ID NO:325), and CDR3 (SEQ ID NO:326) sequences of SEQ ID NO:59. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:60, and/or incorporate amino acid sequences identical to the CDR1 (SEQ ID NO:327), CDR2 (SEQ ID NO:328), and CDR3 (SEQ ID NO:329) sequences of SEQ ID NO:60.

The first antigen-binding site, which binds to NKG2D, in some embodiments, can incorporate a heavy chain variable domain related to SEQ ID NO:61 and a light chain variable domain related to SEQ ID NO:62. For example, the heavy chain variable domain of the first antigen binding site can be at least 90% (e.g., 90%, 91%, 92%, 93%, 94%, 95%, 96%, 97%, 98%, 99%, or 100%) identical to SEQ ID NO:61, and/or incorporate amino acid sequences identical to the CDR1 (SEQ ID NO:63), CDR2 (SEQ ID NO:64), and CDR3 (SEQ ID NO:65) sequences of SEQ ID NO:61. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:62, and/or incorporate amino acid sequences identical to the CDR1 (SEQ ID NO:66), CDR2 (SEQ ID NO:67), and CDR3 (SEQ ID NO:68) sequences of SEQ ID NO:62. In some embodiments, the first antigen-binding site can incorporate a heavy chain variable domain related to SEQ ID NO:69 and a light chain variable domain related to SEQ ID NO:70. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:69, and/or incorporate amino acid sequences identical to the CDR1 (SEQ ID NO:71), CDR2 (SEQ ID NO:72), and CDR3 (SEQ ID NO:73) sequences of SEQ ID NO:69. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:70, and/or incorporate amino acid sequences identical to the CDR1 (SEQ ID NO:74), CDR2 (SEQ ID NO:75), and CDR3 (SEQ ID NO:76) sequences of SEQ ID NO:70.

In some embodiments, the first antigen-binding site can incorporate a heavy chain variable domain related to SEQ ID NO:77 and a light chain variable domain related to SEQ ID NO:78. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:77, and/or incorporate amino acid sequences identical to the CDR1 (SEQ ID NO:79), CDR2 (SEQ ID NO:80), and CDR3 (SEQ ID NO:81) sequences of SEQ ID NO:77. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:78, and/or incorporate amino acid sequences identical to the CDR1 (SEQ ID NO:82), CDR2 (SEQ ID NO:83), and CDR3 (SEQ ID NO:84) sequences of SEQ ID NO:78.

In some embodiments, the first antigen-binding site can incorporate a heavy chain variable domain related to SEQ ID NO:85 and a light chain variable domain related to SEQ ID NO:86. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:85, and/or incorporate amino acid sequences identical to the CDR1 (SEQ ID NO:87), CDR2 (SEQ ID NO:88), and CDR3 (SEQ ID NO:89) sequences of SEQ ID NO:85. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:90), CDR2 (SEQ ID NO:91), and CDR3 (SEQ ID NO:92) sequences of SEQ ID NO:86.

In some embodiments, the first antigen-binding site can incorporate a heavy chain variable domain related to SEQ ID NO:93 and a light chain variable domain related to SEQ ID NO:94. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:93, and/or incorporate amino acid sequences identical to the CDR1 (SEQ ID NO:95), CDR2 (SEQ ID NO:96), and CDR3 (SEQ ID NO:97) sequences of SEQ ID NO:93. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:94, and/or incorporate amino acid sequences identical to the CDR1 (SEQ ID NO:98), CDR2 (SEQ ID NO:99), and CDR3 (SEQ ID NO:100) sequences of SEQ ID NO:94.

In some embodiments, the first antigen-binding site can incorporate a heavy chain variable domain related to SEQ ID NO:101 and a light chain variable domain related to SEQ ID NO:102, such as by having amino acid sequences at least 90% (e.g., 90%, 91%, 92%, 93%, 94%, 95%, 96%, 97%, 98%, 99%, or 100%) identical to SEQ ID NO:101 and at least 90% (e.g., 90%, 91%, 92%, 93%, 94%, 95%, 96%, 97%, 98%, 99%, or 100%) identical to SEQ ID NO:102, respectively. In some embodiments, the first antigen-binding site can incorporate a heavy chain variable domain related to SEQ ID NO:103 and a light chain variable domain related to SEQ ID NO:104, such as by having amino acid sequences at least 90% (e.g., 90%, 91%, 92%, 93%, 94%, 95%, 96%, 97%, 98%, 99%, or 100%) identical to SEQ ID NO:103 and at least 90% (e.g., 90%, 91%, 92%, 93%, 94%, 95%, 96%, 97%, 98%, 99%, or 100%) identical to SEQ ID NO:104, respectively.

In some embodiments, the second antigen-binding site binding to CD37 can incorporate a heavy chain variable domain related to SEQ ID NO:109 and a light chain variable domain related to SEQ ID NO:113. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:109, and/or incorporate amino acid sequences identical to the CDR1 (SEQ ID NO:110), CDR2 (SEQ ID NO:111), and CDR3 (SEQ ID NO:112) sequences of SEQ ID NO:109 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:113, and/or incorporate amino acid sequences identical to the CDR1 (SEQ ID NO:114), CDR2 (SEQ ID NO:115), and CDR3 (SEQ ID NO:116) sequences of SEQ ID NO:113.

Alternatively, the second antigen-binding site binding to CD37 can incorporate a heavy chain variable domain related to SEQ ID NO:117 and a light chain variable domain related to SEQ ID NO:121. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:117, and/or incorporate amino acid sequences identical to the CDR1 (SEQ ID NO:118), CDR2 (SEQ ID NO:119), and CDR3 (SEQ ID NO:120) sequences of SEQ ID NO:117. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:121, and/or incorporate amino acid sequences identical to the CDR1 (SEQ ID NO:122), CDR2 (SEQ ID NO:123), and CDR3 (SEQ ID NO:124) sequences of SEQ ID NO:121.

The second antigen-binding site binding to CD37 can optionally incorporate a heavy chain variable domain related to SEQ ID NO:125 and a light chain variable domain related to SEQ ID NO:129. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:125, and/or incorporate amino acid sequences identical to the CDR1 (SEQ ID NO:126), CDR2 (SEQ ID NO:127), and CDR3 (SEQ ID NO:128) sequences of SEQ ID NO:125. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:129, and/or incorporate amino acid sequences identical to the CDR1 (SEQ ID NO:130), CDR2 (SEQ ID NO:131), and CDR3 (SEQ ID NO:132) sequences of SEQ ID NO:129.

In some embodiments, the second antigen-binding site binding to CD20 can incorporate a heavy chain variable domain related to SEQ ID NO:134 and a light chain variable domain related to SEQ ID NO:138. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:134, and/or incorporate amino acid sequences identical to the CDR1 (SEQ ID NO:135), CDR2 (SEQ ID NO:136), and CDR3 (SEQ ID NO:137) sequences of SEQ ID NO:134 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:138, and/or incorporate amino acid sequences identical to the CDR1 (SEQ ID NO:139), CDR2 (SEQ ID NO:140), and CDR3 (SEQ ID NO:141) sequences of SEQ ID NO:138.

Alternatively, the second antigen-binding site binding to CD20 can optionally incorporate a heavy chain variable domain related to SEQ ID NO:142 and a light chain variable domain related to SEQ ID NO:146. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:142, and/or incorporate amino acid sequences identical to the CDR1 (SEQ ID NO:143), CDR2 (SEQ ID NO:144), and CDR3 (SEQ ID NO:145) sequences of SEQ ID NO:142 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:146, and/or incorporate amino acid sequences identical to the CDR1 (SEQ ID NO:147), CDR2 (SEQ ID NO:148), and CDR3 (SEQ ID NO:149) sequences of SEQ ID NO:146.

The second antigen-binding site binding to CD20 can optionally incorporate a heavy chain variable domain related to SEQ ID NO:150 and a light chain variable domain related to SEQ ID NO:154. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:150, and/or incorporate amino acid sequences identical to the CDR1 (SEQ ID NO:151), CDR2 (SEQ ID NO:152), and CDR3 (SEQ ID NO:153) sequences of SEQ ID NO:150. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:154, and/or incorporate amino acid sequences identical to the CDR1 (SEQ ID NO:155), CDR2 (SEQ ID NO:156), and CDR3 (SEQ ID NO:157) sequences of SEQ ID NO:154.

Alternatively, the second antigen-binding site binding to CD20 can optionally incorporate a heavy chain variable domain related to SEQ ID NO:158 and a light chain variable domain related to SEQ ID NO:162. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:158, and/or incorporate amino acid sequences identical to the CDR1 (SEQ ID NO:159), CDR2 (SEQ ID NO:160), and CDR3 (SEQ ID NO:161) sequences of SEQ ID NO:158 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:163, and/or incorporate amino acid sequences identical to the CDR1 (SEQ ID NO:163), CDR2 (SEQ ID NO:164), and CDR3 (SEQ ID NO:165) sequences of SEQ ID NO:162.

Alternatively, the second antigen-binding site binding to CD20 can optionally incorporate a heavy chain variable domain related to SEQ ID NO:166 and a light chain variable domain related to SEQ ID NO:170. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:166, and/or incorporate amino acid sequences identical to the CDR1 (SEQ ID NO:167), CDR2 (SEQ ID NO:168), and CDR3 (SEQ ID NO:169) sequences of SEQ ID NO:166 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:170, and/or incorporate amino acid sequences identical to the CDR1 (SEQ ID NO:171), CDR2 (SEQ ID NO:172), and CDR3 (SEQ ID NO:173) sequences of SEQ ID NO:170.

In some embodiments, the second antigen-binding site binding to C.D19 can optionally incorporate a heavy chain variable domain related to SEQ ID NO:175 and a light chain variable domain related to SEQ ID NO:179. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:175, and/or incorporate amino acid sequences identical to the CDR1 (SEQ ID NO:176), CDR2 (SEQ ID NO:177), and CDR3 (SEQ ID NO:178) sequences of SEQ ID NO:175. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:179, and/or incorporate amino acid sequences identical to the CDR1 (SEQ ID NO:180), CDR2 (SEQ ID NO:181), and CDR3 (SEQ ID NO:182) sequences of SEQ ID NO:179.

Alternatively, the second antigen-binding site binding to CD19 can optionally incorporate a heavy chain variable domain related to SEQ ID NO:183 and a light chain variable domain related to SEQ ID NO:187. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:183, and/or incorporate amino acid sequences identical to the CDR1 (SEQ ID NO:184), CDR2 (SEQ ID NO:185), and CDR3 (SEQ ID NO:186) sequences of SEQ ID NO:183 Similarly, the light chain variable domain of the second antigen-binding site can be at least 90% (e.g., 90%, 91%, 92%, 93%, 94%, 95%, 96%, 97%, 98%, 99%, or 100%)

identical to SEQ ID NO:187, and/or incorporate amino acid sequences identical to the CDR1 (SEQ ID NO:188), CDR2 (SEQ ID NO:189), and CDR3 (SEQ ID NO:190) sequences of SEQ ID NO:187.

Alternatively, the second antigen-binding site binding to CD19 can optionally incorporate a heavy chain variable domain related to SEQ ID NO:191 and a light chain variable domain related to SEQ ID NO:195. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:191, and/or incorporate amino acid sequences identical to the CDR1 (SEQ ID NO:192), CDR2 (SEQ ID NO:193), and CDR3 (SEQ ID NO:194) sequences of SEQ ID NO:191 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:195, and/or incorporate amino acid sequences identical to the CDR1 (SEQ ID NO:196), CDR2 (SEQ ID NO:197), and CDR3 (SEQ ID NO:198) sequences of SEQ ID NO:195. Alternatively, the second antigen-binding site binding to CD19 can optionally incorporate a heavy chain variable domain related to SEQ ID NO:199 and a light chain variable domain related to SEQ ID NO:203. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:199, and/or incorporate amino acid sequences identical to the CDR1 (SEQ ID NO:200), CDR2 (SEQ ID NO:201), and CDR3 (SEQ ID NO:202) sequences of SEQ ID NO:199. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:203, and/or incorporate amino acid sequences identical to the CDR1 (SEQ ID NO:204), CDR2 (SEQ ID NO:205), and CDR3 (SEQ ID NO:206) sequences of SEQ ID NO:203.

In some embodiments, the second antigen-binding site binding to CD22 can optionally incorporate a heavy chain variable domain related to SEQ ID NO:208 and a light chain variable domain related to SEQ ID NO:212. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:208, and/or incorporate amino acid sequences identical to the CDR1 (SEQ ID NO:209), CDR2 (SEQ ID NO:210), and CDR3 (SEQ ID NO:211) sequences of SEQ ID NO:208. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:212, and/or incorporate amino acid sequences identical to the CDR1 (SEQ ID NO:213), CDR2 (SEQ ID NO:214), and CDR3 (SEQ ID NO:215) sequences of SEQ ID NO:212.

Alternatively, the second antigen-binding site binding to CD22 can optionally incorporate a heavy chain variable domain related to SEQ ID NO:216 and a light chain variable domain related to SEQ ID NO:220. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:216, and/or incorporate amino acid sequences identical to the CDR1 (SEQ ID NO:217), CDR2 (SEQ ID NO:218), and CDR3 (SEQ ID NO:219) sequences of SEQ ID NO:216 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:220, and/or incorporate amino acid sequences identical to the CDR1 (SEQ ID NO:221), CDR2 (SEQ ID NO:222), and CDR3 (SEQ ID NO:223) sequences of SEQ ID NO:220. Alternatively, the second antigen-binding site binding to CD22 can optionally incorporate a heavy chain variable domain related to SEQ ID NO:224 and a light chain variable domain related to SEQ ID NO:228. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:224, and/or incorporate amino acid sequences identical to the CDR1 (SEQ ID NO:225), CDR2 (SEQ ID NO:226), and CDR3 (SEQ ID NO:227) sequences of SEQ ID NO:224. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:228, and/or incorporate amino acid sequences identical to the CDR1 (SEQ ID NO:229), CDR2 (SEQ ID NO:230), and CDR3 (SEQ ID NO:231) sequences of SEQ ID NO:228.

In some embodiments, the second antigen-binding site binding to CD30 can optionally incorporate a heavy chain variable domain related to SEQ ID NO:233 and a light chain variable domain related to SEQ ID NO:237. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:233, and/or incorporate amino acid sequences identical to the CDR1 (SEQ ID NO:234), CDR2 (SEQ ID NO:235), and CDR3 (SEQ ID NO:236) sequences of SEQ ID NO:233. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:237, and/or incorporate amino acid sequences identical to the CDR1 (SEQ ID NO:238), CDR2 (SEQ ID NO:239), and CDR3 (SEQ ID NO:240) sequences of SEQ ID NO:237.

Alternatively, the second antigen-binding site binding to CD30 can optionally incorporate a heavy chain variable domain related to SEQ ID NO:241 and a light chain variable domain related to SEQ ID NO:245. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:241, and/or incorporate amino acid sequences identical to the CDR1 (SEQ ID NO:242), CDR2 (SEQ ID NO:243), and CDR3 (SEQ ID NO:244) sequences of SEQ ID NO:241 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:245, and/or incorporate amino acid sequences identical to the CDR1 (SEQ ID NO:246), CDR2 (SEQ ID NO:247), and CDR3 (SEQ ID NO:248) sequences of SEQ ID NO:245.

Alternatively, the second antigen-binding site binding to CD30 can optionally incorporate a heavy chain variable domain related to SEQ ID NO:249 and a light chain variable domain related to SEQ ID NO:253. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:249, and/or incorporate amino acid sequences identical to the CDR1 (SEQ ID NO:250), CDR2 (SEQ ID NO:251), and CDR3 (SEQ ID NO:252) sequences of SEQ ID NO:249 Similarly, the light chain variable domain of the second antigen-binding site can be at least 90% (e.g., 90%, 91%, 92%, 93%, 94%, 95%, 96%, 97%, 98%, 99%, or 100%)

identical to SEQ ID NO:253, and/or incorporate amino acid sequences identical to the CDR1 (SEQ ID NO:254), CDR2 (SEQ ID NO:255), and CDR3 (SEQ ID NO:256) sequences of SEQ ID NO:253.

Alternatively, the second antigen-binding site binding to CD30 can optionally incorporate a heavy chain variable domain related to SEQ ID NO:257 and a light chain variable domain related to SEQ ID NO:261. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:257, and/or incorporate amino acid sequences identical to the CDR1 (SEQ ID NO:258), CDR2 (SEQ ID NO:259), and CDR3 (SEQ ID NO:260) sequences of SEQ ID NO:257 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:261, and/or incorporate amino acid sequences identical to the CDR1 (SEQ ID NO:262), CDR2 (SEQ ID NO:263), and CDR3 (SEQ ID NO:264) sequences of SEQ ID NO:261.

Alternatively, the second antigen-binding site binding to CD30 can optionally incorporate a heavy chain variable domain related to SEQ ID NO:265 and a light chain variable domain related to SEQ ID NO:269. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:265, and/or incorporate amino acid sequences identical to the CDR1 (SEQ ID NO:266), CDR2 (SEQ ID NO:267), and CDR3 (SEQ ID NO:268) sequences of SEQ ID NO:265 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:269, and/or incorporate amino acid sequences identical to the CDR1 (SEQ ID NO:270), CDR2 (SEQ ID NO:271), and CDR3 (SEQ ID NO:272) sequences of SEQ ID NO:269.

In some embodiments, the second antigen-binding site binding to CD52 can optionally incorporate a heavy chain variable domain related to SEQ ID NO:274 and a light chain variable domain related to SEQ ID NO:278. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:274, and/or incorporate amino acid sequences identical to the CDR1 (SEQ ID NO:275), CDR2 (SEQ ID NO:276), and CDR3 (SEQ ID NO:278) sequences of SEQ ID NO:274. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:278, and/or incorporate amino acid sequences identical to the CDR1 (SEQ ID NO:279), CDR2 (SEQ ID NO:280), and CDR3 (SEQ ID NO:281) sequences of SEQ ID NO:278.

Alternatively, the second antigen-binding site binding to CD52 can optionally incorporate a heavy chain variable domain related to SEQ ID NO:282 and a light chain variable domain related to SEQ ID NO:286. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:282, and/or incorporate amino acid sequences identical to the CDR1 (SEQ ID NO:283), CDR2 (SEQ ID NO:284), and CDR3 (SEQ ID NO:285) sequences of SEQ ID NO:282 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:286, and/or incorporate amino acid sequences identical to the CDR1 (SEQ ID NO:287), CDR2 (SEQ ID NO:288), and CDR3 (SEQ ID NO:289) sequences of SEQ ID NO:286.

In some embodiments, the second antigen-binding site binding to CD133 can optionally incorporate a heavy chain variable domain related to SEQ ID NO:291 and a light chain variable domain related to SEQ ID NO:295. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:291, and/or incorporate amino acid sequences identical to the CDR1 (SEQ ID NO:292), CDR2 (SEQ ID NO:293), and CDR3 (SEQ ID NO:294) sequences of SEQ ID NO:291. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:295, and/or incorporate amino acid sequences identical to the CDR1 (SEQ ID NO:296), CDR2 (SEQ ID NO:297), and CDR3 (SEQ ID NO:298) sequences of SEQ ID NO:295.

Alternatively, the second antigen-binding site binding to CD133 can optionally incorporate a heavy chain variable domain related to SEQ ID NO:299 and a light chain variable domain related to SEQ ID NO:303. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:299, and/or incorporate amino acid sequences identical to the CDR1 (SEQ ID NO:300), CDR2 (SEQ ID NO:301), and CDR3 (SEQ ID NO:302) sequences of SEQ ID NO:299 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:303, and/or incorporate amino acid sequences identical to the CDR1 (SEQ ID NO:304), CDR2 (SEQ ID NO:305), and CDR3 (SEQ ID NO:306) sequences of SEQ ID NO:303.

Alternatively, the second antigen-binding site binding to CD133 can optionally incorporate a heavy chain variable domain related to SEQ ID NO:307 and a light chain variable domain related to SEQ ID NO:311. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:307, and/or incorporate amino acid sequences identical to the CDR1 (SEQ ID NO:308), CDR2 (SEQ ID NO:309), and CDR3 (SEQ ID NO:310) sequences of SEQ ID NO:307 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:311, and/or incorporate amino acid sequences identical to the CDR1 (SEQ ID NO:312), CDR2 (SEQ ID NO:313), and CDR3 (SEQ ID NO:314) sequences of SEQ ID NO:311.

Alternatively, the second antigen-binding site binding to CD133 can optionally incorporate a heavy chain variable domain related to SEQ ID NO:315 and a light chain variable domain related to SEQ ID NO:319. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:315, and/or incorporate amino acid sequences identical to the CDR1 (SEQ ID NO:316), CDR2 (SEQ ID NO:317), and CDR3 (SEQ ID NO:318) sequences of SEQ ID NO:315 Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:319, and/or incorporate amino acid sequences identical to the CDR1 (SEQ ID NO:320), CDR2 (SEQ ID NO:321), and CDR3 (SEQ ID NO:322) sequences of SEQ ID NO:319.

In some embodiments, the second antigen binding site incorporates a light chain variable domain having an amino acid sequence identical to the amino acid sequence of the light chain variable domain present in the first antigen binding site.

In some embodiments, the protein incorporates a portion of an antibody Fc domain sufficient to bind CD16, wherein the antibody Fc domain comprises hinge and CH2 domains, and/or amino acid sequences at least 90% identical to amino acid sequence 234-332 of a human IgG antibody.

Formulations containing any one of the proteins described herein; cells containing one or more nucleic acids expressing the proteins, and methods of enhancing tumor cell death using the proteins are also provided.

Another aspect of the invention provides a method of treating cancer in a patient. The method comprises administering to a patient in need thereof a therapeutically effective amount of the multi-specific binding proteins described herein. Cancers to be treated using CD37-targeting multi-specific binding proteins include any cancer that expresses CD37, for example, B-cell chronic lymphocytic leukemia (CLL), hairy-cell leukemia (HCL), non-Hodgkin lymphoma, and acute myeloid leukemia. Cancers to be treated using CD20-targeting multi-specific binding proteins include any cancer that expresses CD20, for example, chronic lymphocytic leukemia, non-Hodgkin's lymphoma, follicular lymphoma, and B-cell malignancies. Cancers to be treated using CD19-targeting multi-specific binding proteins include any cancer that expresses CD19, for example, chronic lymphocytic leukemia, non-Hodgkin's lymphoma, follicular lymphoma, acute lymphoblastic leukemia, B cell malignancies, multiple myeloma, and acute myeloid leukemia. Cancers to be treated using CD22-targeting multi-specific binding proteins include any cancer that expresses chronic lymphocytic leukemia, non-Hodgkin's lymphoma, follicular lymphoma, acute lymphoblastic leukemia, B cell malignancies, and hairy cell leukemia. Cancers to be treated using CD30-targeting multi-specific binding proteins include any cancer that expresses CD30, for example, Hodgkin's lymphoma, anaplastic large cell lymphoma, cutaneous T-cell lymphoma, peripheral T cell lymphoma, adult T-cell leukemia-lymphoma, diffuse large B cell lymphoma, non-Hodgkin's lymphoma, and embryonal cell carcinoma. Cancers to be treated using CD52-targeting multi-specific binding proteins include any cancer that expresses CD52, for example, chronic lymphocytic leukemia (CLL), cutaneous T-cell lymphoma, peripheral T-cell lymphoma and T-cell prolymphocytic leukemia, B cell malignancies, non-Hodgkin's lymphoma, Hodgkin's lymphoma, anaplastic large cell lymphoma, adult T-cell leukemia-lymphoma, mature T/natural killer (NK) cell neoplasms, and thymoma. Cancers to be treated using CD133-targeting multi-specific binding proteins include any cancer that expresses CD133, for example, breast cancer, colon cancer, prostate cancer, liver cancer, pancreatic cancer, lung cancer, ovarian cancer, renal cancer, uterine cancer, testicular germ cell cancer, acute myeloid leukemia, acute lymphoblastic leukemia, glioma, glioblastoma, and head and neck squamous cell carcinoma.

BRIEF DESCRIPTION OF THE DRAWINGS

FIG. 19A demonstrates levels of CD107a; FIG. 19B demonstrates levels of IFN-γ; FIG. 19C demonstrates levels of CD107a and IFN-γ. Graphs indicate the mean (n=2)±SD. Data are representative of five independent experiments using five different healthy donors.

FIG. 30A is an exemplary representation of one form of a κλ-Body;

FIG. 30B is an exemplary representation of another κλ-Body.

DETAILED DESCRIPTION

Figure 1:
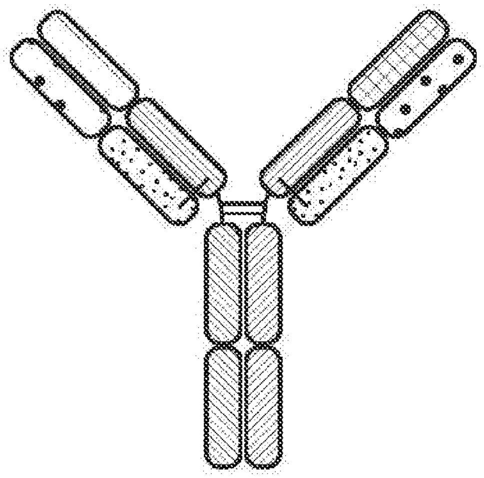
FIG. 1 is a representation of a heterodimeric, multi-specific antibody. Each arm can represent either the NKG2D-binding domain, or a binding domain for CD37, CD20, CD19, CD22, CD30, CD52, or CD133. In some embodiments, the NKG2D- and the antigen-binding domains can share a common light chain.

The invention provides multi-specific binding proteins that bind the NKG2D receptor and CD16 receptor on natural killer cells, and a tumor-associated antigen selected from CD37, CD20, CD19, CD22, CD30, CD52, and CD133. In some embodiments, the multi-specific proteins further include an additional antigen-binding site that binds a tumor-associated antigen. The invention also provides pharmaceutical compositions comprising such multi-specific binding proteins, and therapeutic methods using such multi-specific proteins and pharmaceutical compositions, for purposes such as treating cancer. Various aspects of the invention are set forth below in sections; however, aspects of the invention described in one particular section are not to be limited to any particular section.

To facilitate an understanding of the present invention, a number of terms and phrases are defined below.

The terms "a" and "an" as used herein mean "one or more" and include the plural unless the context is inappropriate.

As used herein, the term "antigen-binding site" refers to the part of the immunoglobulin molecule that participates in antigen binding. In human antibodies, the antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FR." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide.

The term "tumor associated antigen" as used herein means any antigen including but not limited to a protein, glycoprotein, ganglioside, carbohydrate, lipid that is associated with cancer. Such antigen can be expressed on malignant cells or in the tumor microenvironment such as on tumor-associated blood vessels, extracellular matrix, mesenchymal stroma, or immune infiltrates.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Proteins

The invention provides multi-specific binding proteins that bind to the NKG2D receptor and CD16 receptor on natural killer cells, and a tumor-associated antigen selected from CD37, CD20, CD19, CD22, CD30, CD52, and CD133. The multi-specific binding proteins are useful in the pharmaceutical compositions and therapeutic methods described herein. Binding of the multi-specific binding proteins to the NKG2D receptor and CD16 receptor on a natural killer cell enhances the activity of the natural killer cell toward destruction of tumor cells expressing CD37, CD20, CD19, CD22, CD30, CD52, or CD133 antigen. Binding of the multi-specific binding proteins to CD37, CD20, CD19, CD22, CD30, CD52, or CD133-expressing cells brings the cancer cells into proximity with the natural killer cell, which facilitates direct and indirect destruction of the cancer cells by the natural killer cell. Further description of some exemplary multi-specific binding proteins is provided below.

The first component of the multi-specific binding proteins binds to NKG2D receptor-expressing cells, which can include but are not limited to NK cells, γδ T cells and $CD8^{+}αβ$ T cells. Upon NKG2D binding, the multi-specific binding proteins may block natural ligands, such as ULBP6 and MICA, from binding to NKG2D and activating NKG2D receptors.

The second component of the multi-specific binding proteins binds to CD37, CD20, CD19, CD22, CD30, CD52, or CD133. CD37-expressing cells may be found in, for example, B-cell chronic lymphocytic leukemia (CLL), hairy-cell leukemia (HCL), non-Hodgkin lymphoma, and acute myeloid leukemia. CD20-expressing cells may be found in, for example, chronic lymphocytic leukemia, non-Hodgkin's lymphoma, follicular lymphoma, and B-cell malignancies. CD19-expressing cells may be found in, for example, chronic lymphocytic leukemia, non-Hodgkin's lymphoma, follicular lymphoma, acute lymphoblastic leukemia, B cell malignancies, multiple myeloma, and acute myeloid leukemia. CD22-expressing cells may be found in, for example, chronic lymphocytic leukemia, non-Hodgkin's lymphoma, follicular lymphoma, acute lymphoblastic leukemia, B cell malignancies, and hairy cell leukemia. CD30-expressing cells may be found in, for example, Hodgkin's lymphoma, anaplastic large cell lymphoma, cutaneous T-cell lymphoma, peripheral T cell lymphoma, adult T-cell leukemia-lymphoma, diffuse large B cell lymphoma, non-Hodgkin's lymphoma, and embryonal cell carcinoma. CD52-expressing cells may be found, for example in, but are not limited to chronic lymphocytic leukemia (CLL), cutaneous T-cell lymphoma, peripheral T-cell lymphoma and T-cell prolymphocytic leukemia, B cell malignancies, non-Hodgkin's lymphoma, Hodgkin's lymphoma, anaplastic large cell lymphoma, adult T-cell leukemia-lymphoma, mature T/natural killer (NK) cell neoplasms, and thymoma. CD133-expressing cells may be found, for example in, but are not limited to breast cancer, colon cancer, prostate cancer, liver cancer, pancreatic cancer, lung cancer, ovarian cancer, renal cancer, uterine cancer, testicular germ cell cancer, acute myeloid leukemia, acute lymphoblastic leukemia, glioma, glioblastoma, and head and neck squamous cell carcinoma.

The third component for the multi-specific binding proteins binds to cells expressing CD16, an Fc receptor on the surface of leukocytes including natural killer cells, macrophages, neutrophils, eosinophils, mast cells, and follicular dendritic cells.

The multi-specific binding proteins described herein can take various formats. For example, one format is a heterodimeric, multi-specific antibody including a first immunoglobulin heavy chain, a first immunoglobulin light chain, a second immunoglobulin heavy chain and a second immunoglobulin light chain (FIG. 1). The first immunoglobulin heavy chain includes a first Fc (hinge-CH2-CH3) domain, a first heavy chain variable domain and optionally a first CH1 heavy chain domain. The first immunoglobulin light chain includes a first light chain variable domain and a first light chain constant domain. The first immunoglobulin light chain, together with the first immunoglobulin heavy chain, forms an antigen-binding site that binds NKG2D. The second immunoglobulin heavy chain comprises a second Fc (hinge-CH2-CH3) domain, a second heavy chain variable domain and optionally a second CH1 heavy chain domain. The second immunoglobulin light chain includes a second light chain variable domain and a second light chain constant domain. The second immunoglobulin light chain, together with the second immunoglobulin heavy chain, forms an antigen-binding site that binds CD37, CD20, CD19, CD22, CD30, CD52, or CD133. The first Fc domain and second Fc domain together are able to bind to CD16 (FIG. 1). In some embodiments, the first immunoglobulin light chain is identical to the second immunoglobulin light chain.

Figure 2:
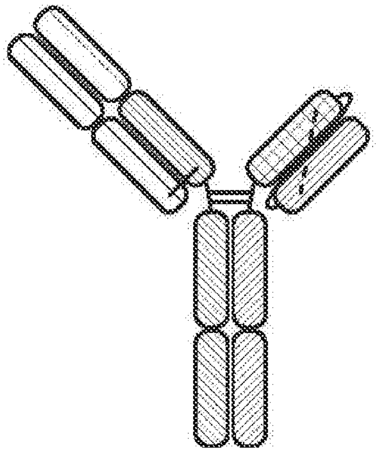
FIG. 2 is a representation of a heterodimeric, multi-specific antibody. Either the NKG2D-binding domain or the binding domain for an antigen selected from CD37, CD20, CD19, CD22, CD30, CD52, and CD133, can take the scFv format (right arm).

Another exemplary format involves a heterodimeric, multi-specific antibody including a first immunoglobulin heavy chain, a second immunoglobulin heavy chain and an immunoglobulin light chain (FIG. 2). The first immunoglobulin heavy chain includes a first Fc (hinge-CH2-CH3) domain fused via either a linker or an antibody hinge to a single-chain variable fragment (scFv) composed of a heavy chain variable domain and light chain variable domain which pair and bind NKG2D, or bind an antigen selected from CD37, CD20, CD19, CD22, CD30, CD52, and CD133. The second immunoglobulin heavy chain includes a second Fc (hinge-CH2-CH3) domain, a second heavy chain variable domain and optionally a CH1 heavy chain domain. The immunoglobulin light chain includes a light chain variable domain and a light chain constant domain. The second immunoglobulin heavy chain pairs with the immunoglobulin light chain and binds to NKG2D or binds a tumor-associated antigen selected from CD37, CD20, CD19, CD22, CD30, CD52, and CD133. The first Fc domain and the second Fc domain together are able to bind to CD16 (FIG. 2).

One or more additional binding motifs may be fused to the C-terminus of the constant region CH3 domain, optionally via a linker sequence. In certain embodiments, the antigen-binding site could be a single-chain or disulfide-stabilized variable region (scFv) or could form a tetravalent or trivalent molecule.

In some embodiments, the multi-specific binding protein is in the Triomab form, which is a trifunctional, bispecific antibody that maintains an IgG-like shape. This chimera consists of two half antibodies, each with one light and one heavy chain, that originate from two parental antibodies.

In some embodiments, the multi-specific binding protein is the KiH Common Light Chain (LC) form, which involves the knobs-into-holes (KIHs) technology. The KIH involves engineering $C_H3$ domains to create either a "knob" or a "hole" in each heavy chain to promote heterodimerization. The concept behind the "Knobs-into-Holes (KiH)" Fc technology was to introduce a "knob" in one CH3 domain (CH3A) by substitution of a small residue with a bulky one (e.g., $T366W_{CH3A}$ in EU numbering). To accommodate the "knob," a complementary "hole" surface was created on the other CH3 domain (CH3B) by replacing the closest neighboring residues to the knob with smaller ones (e.g., $T366S/L368A/Y407V_{CH3B}$). The "hole" mutation was optimized by structured-guided phage library screening (Atwell S, Ridgway J B, Wells J A, Carter P., Stable heterodimers from remodeling the domain interface of a homodimer using a phage display library, *J. Mol. Biol.* (1997) 270(1):26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. *J. Mol. Biol.* (2014) 426(9):1947-57; Mimoto F, Kadono S, Katada H, Igawa T, Kamikawa T, Hattori K. Crystal structure of a novel asymmetrically engineered Fc variant with improved affinity for FcγRs. *Mol. Immunol.* (2014) 58(1):132-8) demonstrated that heterodimerization is thermodynamically favored by hydrophobic interactions driven by steric complementarity at the inter- CH3 domain core interface, whereas the knob-knob and the hole-hole interfaces do not favor homodimerization owing to steric hindrance and disruption of the favorable interactions, respectively.

In some embodiments, the multi-specific binding protein is in the dual-variable domain immunoglobulin (DVD-Ig™) form, which combines the target binding domains of two monoclonal antibodies via flexible naturally occurring linkers, and yields a tetravalent IgG-like molecule.

In some embodiments, the multi-specific binding protein is in the Orthogonal Fab interface (Ortho-Fab) form. In the ortho-Fab IgG approach (Lewis S M, Wu X, Pustilnik A, Sereno A, Huang F, Rick H L, et al., Generation of bispecific IgG antibodies by structure-based design of an orthogonal Fab interface. *Nat. Biotechnol.* (2014) 32(2):191-8), structure-based regional design introduces complementary mutations at the LC and $HC_{VH-CH1}$ interface in only one Fab, without any changes being made to the other Fab.

In some embodiments, the multi-specific binding protein is in the 2-in-1 Ig format. In some embodiments, the multi-specific binding protein is in the ES form, which is a heterodimeric construct containing two different Fabs binding to targets 1 and target 2 fused to the Fc. Heterodimerization is ensured by electrostatic steering mutations in the Fc.

Figure 30A:
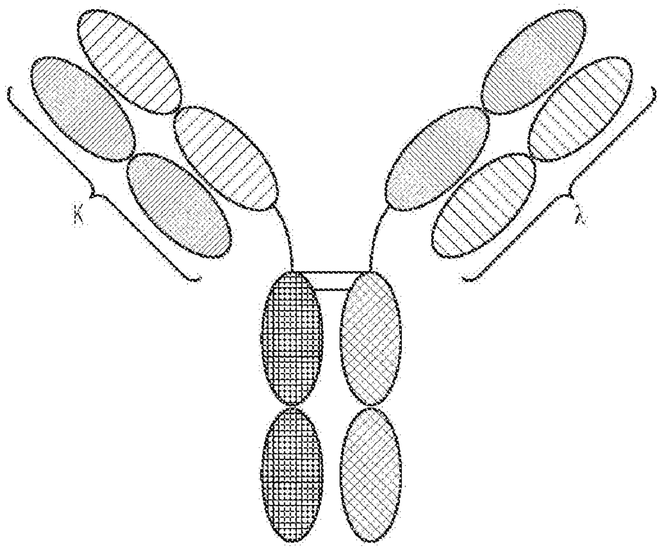
FIGS. 30A-30B are representations of TriNKETs in the κλ-Body forms, which are heterodimeric constructs with two different Fabs fused to Fc stabilized by heterodimerization mutations: Fab1 targeting antigen 1 contains kappa LC, while second Fab targeting antigen 2 contains lambda LC.
Figure 30B:
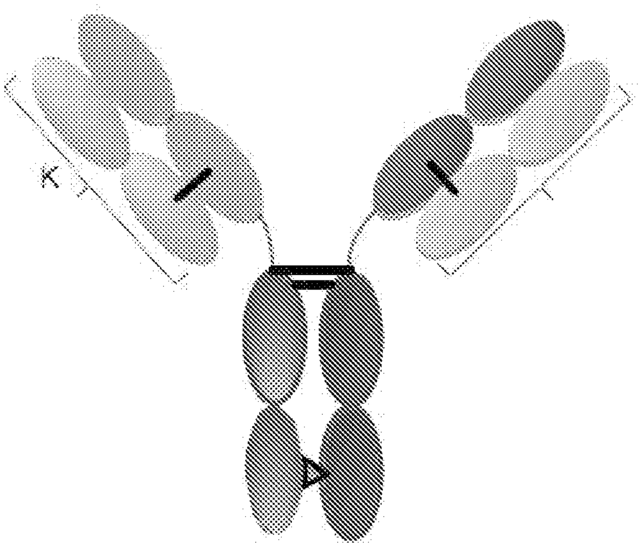
Figure 31:
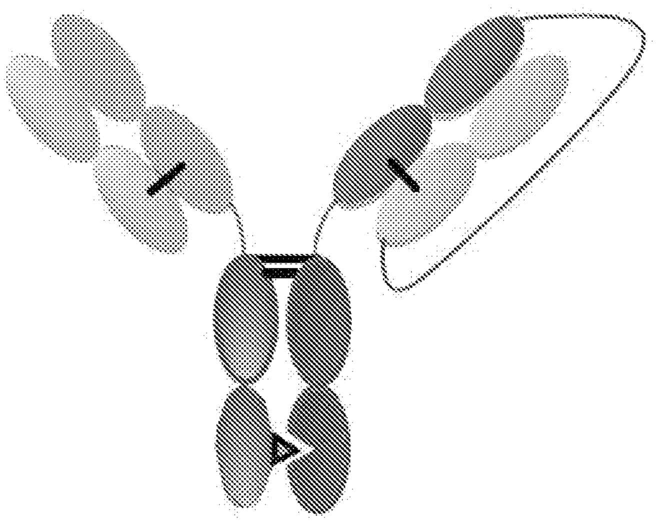
FIG. 31 is an Oasc-Fab heterodimeric construct that includes Fab binding to target 1 and scFab binding to target 2 fused to Fc. Heterodimerization is ensured by mutations in the Fc.
Figure 32:
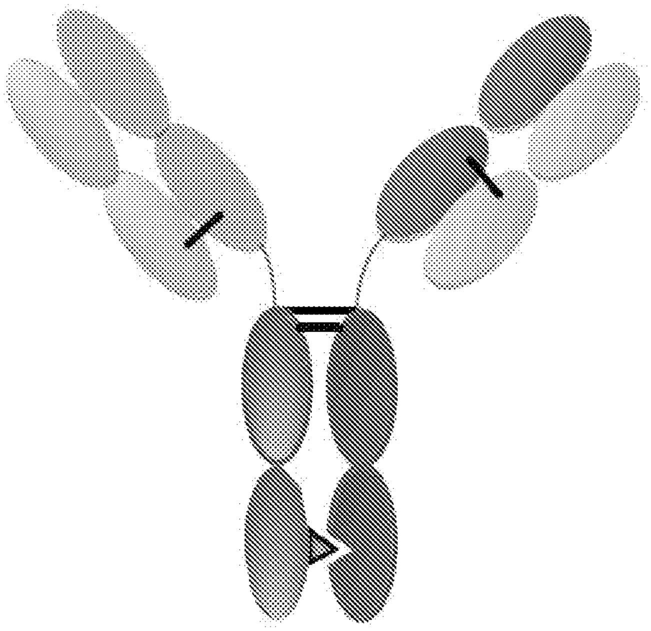
FIG. 32 is a DuetMab, which is a heterodimeric construct containing two different Fabs binding to antigens 1 and 2, and Fc stabilized by heterodimerization mutations. Fab 1 and 2 contain differential S-S bridges that ensure correct light chain (LC) and heavy chain (HC) pairing.
Figure 33:
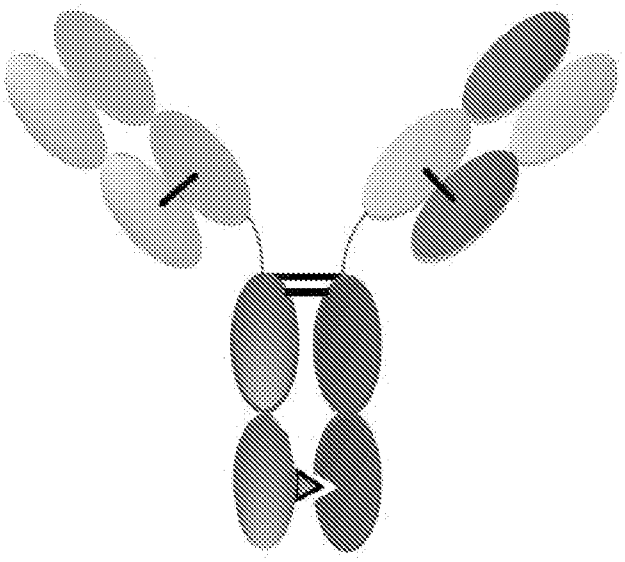
FIG. 33 is a CrossmAb, which is a heterodimeric construct with two different Fabs binding to targets 1 and 2 fused to Fc stabilized by heterodimerization. CL and CH1 domains and VH and VL domains are switched, e.g., CH1 is fused in-line with VL, while CL is fused in-line with VH.
Figure 34:
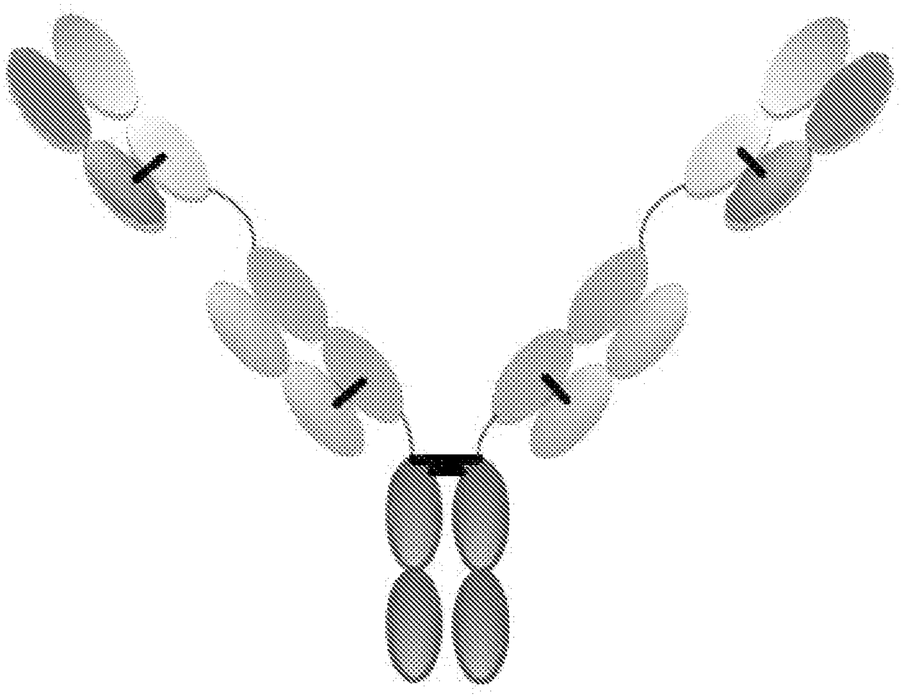
FIG. 34 is a Fit-Ig, which is a homodimeric construct where Fab binding to antigen 2 is fused to the N-terminus of HC of Fab that binds to antigen 1. The construct contains wild-type Fc.

In some embodiments, the multi-specific binding protein is in the κλ-Body form, which is a heterodimeric construct with two different Fabs fused to Fc stabilized by heterodimerization mutations: Fab1 targeting antigen 1 contains kappa LC, while second Fab targeting antigen 2 contains lambda LC. FIG. 30A is an exemplary representation of one form of a κλ-Body; FIG. 30B is an exemplary representation of another κλ-Body.

In some embodiments, the multi-specific binding protein is in Fab Arm Exchange form (antibodies that exchange Fab arms by swapping a heavy chain and attached light chain (half-molecule) with a heavy-light chain pair from another molecule, which results in bispecific antibodies).

In some embodiments, the multi-specific binding protein is in the SEED Body form. The strand-exchange engineered domain (SEED) platform was designed to generate asymmetric and bispecific antibody-like molecules, a capability that expands therapeutic applications of natural antibodies. This protein engineered platform is based on exchanging structurally related sequences of immunoglobulin within the conserved CH3 domains. The SEED design allows efficient generation of AG/GA heterodimers, while disfavoring homodimerization of AG and GA SEED CH3 domains. (Muda M. et al., *Protein Eng. Des. Sel.* (2011, 24(5):447-54)).

In some embodiments, the multi-specific binding protein is in the LuZ-Y form, in which a leucine zipper is used to induce heterodimerization of two different HCs. (Wranik, B J. et al., *J. Biol. Chem.* (2012), 287:43331-9).

In some embodiments, the multi-specific binding protein is in the Cov-X-Body form. In bispecific CovX-Bodies, two different peptides are joined together using a branched azetidinone linker and fused to the scaffold antibody under mild conditions in a site-specific manner. Whereas the pharmacophores are responsible for functional activities, the antibody scaffold imparts long half-life and Ig-like distribution. The pharmacophores can be chemically optimized or replaced with other pharmacophores to generate optimized or unique bispecific antibodies. (Doppalapudi V R et al., *PNAS* (2010), 107(52); 22611-22616).

In some embodiments, the multi-specific binding protein is in an Oasc-Fab heterodimeric form that includes Fab binding to target 1, and scFab binding to target 2 fused to Fc. Heterodimerization is ensured by mutations in the Fc.

In some embodiments, the multi-specific binding protein is in a DuetMab form, which is a heterodimeric construct containing two different Fabs binding to antigens 1 and 2, and Fc stabilized by heterodimerization mutations. Fab 1 and 2 contain differential S-S bridges that ensure correct LC and HC pairing.

In some embodiments, the multi-specific binding protein is in a CrossmAb form, which is a heterodimeric construct with two different Fabs binding to targets 1 and 2, fused to Fc stabilized by heterodimerization. CL and CH1 domains and VH and VL domains are switched, e.g., CH1 is fused in-line with VL, while CL is fused in-line with VH.

In some embodiments, the multi-specific binding protein is in a Fit-Ig form, which is a homodimeric construct where Fab binding to antigen 2 is fused to the N terminus of HC of Fab that binds to antigen 1. The construct contains wild-type Fc.

Table 1 lists peptide sequences of heavy chain variable domains and light chain variable domains that, in combination, can bind to NKG2D. The NKG2D binding domains can vary in their binding affinity to NKG2D, nevertheless, they all activate human NKG2D and NK cells.

TABLE 1

| Clones | Heavy chain variable region amino acid sequence | Light chain variable region amino acid sequence |
|---|---|---|
| ADI-27705 | QVQLQQWGAGLLKPSETLSLTCAV<br>YGGSFSGYYWSWIRQPPGKGLEWI<br>GEIDHSGSTNYNPSLKSRVTISVDTS<br>KNQFSLKLSSVTAADTAVYYCARA<br>RGPWSFDPWGQGTLVTVSS<br>(SEQ ID NO: 1)<br>CDR1 (SEQ ID NO: 105) -<br>GSFSGYYWS<br>CDR2 (SEQ ID NO: 106) -<br>EIDHSGSTNYNPSLKS<br>CDR3 (SEQ ID NO: 107) -<br>ARARGPWSFDP | DIQMTQSPSTLSASVGDRVTIT<br>CRASQSISSWLAWYQQKPGK<br>APKLLIYKASSLESGVPSRFSG<br>SGSGTEFTLTISSLQPDDFATY<br>YCQQYNSYPITFGGGTKVEIK<br>(SEQ ID NO: 2) |
| ADI-27724 | QVQLQQWGAGLLKPSETLSLTCAV<br>YGGSFSGYYWSWIRQPPGKGLEWI<br>GEIDHSGSTNYNPSLKSRVTISVDTS<br>KNQFSLKLSSVTAADTAVYYCARA<br>RGPWSFDPWGQGTLVTVSS<br>(SEQ ID NO: 3) | EIVLTQSPGTLSLSPGERATLS<br>CRASQSVSSSYLAWYQQKPG<br>QAPRLLIYGASSRATGIPDRFS<br>GSGSGTDFTLTISRLEPEDFAV<br>YYCQQYGSSPITFGGGTKVEI<br>K<br>(SEQ ID NO: 4) |

TABLE 1-continued

| Clones | Heavy chain variable region amino acid sequence | Light chain variable region amino acid sequence |
|---|---|---|
| ADI-27740 (A40) | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 5) | DIQMTQSPSTLSASVGDRVTIT CRASQSIGSWLAWYQQKPGK APKLLIYKASSLESGVPSRFSG SGSGTEFTLTISSLQPDDFATY YCQQYHSFYTFGGGTKVEIK (SEQ ID NO: 6) |
| ADI-27741 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 7) | DIQMTQSPSTLSASVGDRVTIT CRASQSIGSWLAWYQQKPGK APKLLIYKASSLESGVPSRFSG SGSGTEFTLTISSLQPDDFATY YCQQSNSYYTFGGGTKVEIK (SEQ ID NO: 8) |
| ADI-27743 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 9) | DIQMTQSPSTLSASVGDRVTIT CRASQSISSWLAWYQQKPGK APKLLIYKASSLESGVPSRFSG SGSGTEFTLTISSLQPDDFATY YCQQYNSYPTFGGGTKVEIK (SEQ ID NO: 10) |
| ADI-28153 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWGFDPWGQGTLVTVSS (SEQ ID NO: 11) | ELQMTQSPSSLSASVGDRVTIT CRTSQSISSYLNWYQQKPGQP PKLLIYWASTRESGVPDRFSGS GSGTDFTLTISSLQPEDSATYY CQQSYDIPYTFGQGTKLEIK (SEQ ID NO: 12) |
| ADI-28226 (C26) | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 13) | DIQMTQSPSTLSASVGDRVTIT CRASQSISSWLAWYQQKPGK APKLLIYKASSLESGVPSRFSG SGSGTEFTLTISSLQPDDFATY YCQQYGSFPITFGGGTKVEIK (SEQ ID NO: 14) |
| ADI-28154 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 15) | DIQMTQSPSTLSASVGDRVTIT CRASQSISSWLAWYQQKPGK APKLLIYKASSLESGVPSRFSG SGSGTDFTLTISSLQPDDFATY YCQQSKEVPWTFGQGTKVEIK (SEQ ID NO: 16) |
| ADI-29399 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 17) | DIQMTQSPSTLSASVGDRVTIT CRASQSISSWLAWYQQKPGK APKLLIYKASSLESGVPSRFSG SGSGTEFTLTISSLQPDDFATY YCQQYNSFPTFGGGTKVEIK (SEQ ID NO: 18) |
| ADI-29401 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 19) | DIQMTQSPSTLSASVGDRVTIT CRASQSIGSWLAWYQQKPGK APKLLIYKASSLESGVPSRFSG SGSGTEFTLTISSLQPDDFATY YCQQYDIYPTFGGGTKVEIK (SEQ ID NO: 20) |
| ADI-29403 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 21) | DIQMTQSPSTLSASVGDRVTIT CRASQSISSWLAWYQQKPGK APKLLIYKASSLESGVPSRFSG SGSGTEFTLTISSLQPDDFATY YCQQYDSYPTFGGGTKVEIK (SEQ ID NO: 22) |
| ADI-29405 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 23) | DIQMTQSPSTLSASVGDRVTIT CRASQSISSWLAWYQQKPGK APKLLIYKASSLESGVPSRFSG SGSGTEFTLTISSLQPDDFATY YCQQYGSFPTFGGGTKVEIK (SEQ ID NO: 24) |
| ADI-29407 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 25) | DIQMTQSPSTLSASVGDRVTIT CRASQSISSWLAWYQQKPGK APKLLIYKASSLESGVPSRFSG SGSGTEFTLTISSLQPDDFATY YCQQYQSFPTFGGGTKVEIK (SEQ ID NO: 26) |

TABLE 1-continued

| Clones | Heavy chain variable region amino acid sequence | Light chain variable region amino acid sequence |
|---|---|---|
| ADI-29419 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 27) | DIQMTQSPSTLSASVGDRVTITCRASQSISSWLAWYQQKPGKAPKLLIYKASSLESGVPSRFSGSGSGTEFTLTISSLQPDDFATYYCQQYSSFSTFGGGTKVEIK (SEQ ID NO: 28) |
| ADI-29421 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 29) | DIQMTQSPSTLSASVGDRVTITCRASQSISSWLAWYQQKPGKAPKLLIYKASSLESGVPSRFSGSGSGTEFTLTISSLQPDDFATYYCQQYESYSTFGGGTKVEIK (SEQ ID NO: 30) |
| ADI-29424 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 31) | DIQMTQSPSTLSASVGDRVTITCRASQSISSWLAWYQQKPGKAPKLLIYKASSLESGVPSRFSGSGSGTEFTLTISSLQPDDFATYYCQQYDSFITFGGGTKVEIK (SEQ ID NO: 32) |
| ADI-29425 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 33) | DIQMTQSPSTLSASVGDRVTITCRASQSISSWLAWYQQKPGKAPKLLIYKASSLESGVPSRFSGSGSGTEFTLTISSLQPDDFATYYCQQYQSYPTFGGGTKVEIK (SEQ ID NO: 34) |
| ADI-29426 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 35) | DIQMTQSPSTLSASVGDRVTITCRASQSIGSWLAWYQQKPGKAPKLLIYKASSLESGVPSRFSGSGSGTEFTLTISSLQPDDFATYYCQQYHSFPTFGGGTKVEIK (SEQ ID NO: 36) |
| ADI-29429 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 37) | DIQMTQSPSTLSASVGDRVTITCRASQSIGSWLAWYQQKPGKAPKLLIYKASSLESGVPSRFSGSGSGTEFTLTISSLQPDDFATYYCQQYELYSYTFGGGTKVEIK (SEQ ID NO: 38) |
| ADI-29447 (F47) | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 39) | DIQMTQSPSTLSASVGDRVTITCRASQSISSWLAWYQQKPGKAPKLLIYKASSLESGVPSRFSGSGSGTEFTLTISSLQPDDFATYYCQQYDTFITFGGGTKVEIK (SEQ ID NO: 40) |
| ADI-27727 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGDSSIRHAYYYYGMDVWGQGTTVTVSS (SEQ ID NO: 41)<br>CDR1 (SEQ ID NO: 43) - GTFSSYAIS<br>CDR2 (SEQ ID NO: 44) - GIIPIFGTANYAQKFQG<br>CDR3 (SEQ ID NO: 45) - ARGDSSIRHAYYYYGMDV | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPITFGGGTKVEIK (SEQ ID NO: 42)<br>CDR1 (SEQ ID NO: 46) - KSSQSVLYSSNNKNYLA<br>CDR2 (SEQ ID NO: 47) - WASTRES<br>CDR3 (SEQ ID NO: 48) - QQYYSTPIT |
| ADI-29443 (F43) | QLQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCARGSDRFHPYFDYWGQGTLVTVSS (SEQ ID NO: 49)<br>CDR1 (SEQ ID NO: 51) - GSISSSSYYWG<br>CDR2 (SEQ ID NO: 52) - SIYYSGSTYYNPSLKS<br>CDR3 (SEQ ID NO: 53) - ARGSDRFHPYFDY | EIVLTQSPATLSLSPGERATLSCRASQSVSRYLAWYQQKPGQAPRLLIYDASNRATGIPARFSGSGSGTDFTLTISSLEPEDFAVYYCQQFDTWPPTFGGGTKVEIK (SEQ ID NO: 50)<br>CDR1 (SEQ ID NO: 54) - RASQSVSRYLA<br>CDR2 (SEQ ID NO: 55) - DASNRAT<br>CDR3 (SEQ ID NO: 56) - QQFDTWPPT |

TABLE 1-continued

| Clones | Heavy chain variable region amino acid sequence | Light chain variable region amino acid sequence |
|---|---|---|
| ADI-29404 (F04) | QVQLQQWGAGLLKPSETLSLTCAV<br>YGGSFSGYYWSWIRQPPGKGLEWI<br>GEIDHSGSTNYNPSLKSRVTISVDTS<br>KNQFSLKLSSVTAADTAVYYCARA<br>RGPWSFDPWGQGTLVTVSS<br>(SEQ ID NO: 57) | DIQMTQSPSTLSASVGDRVTIT<br>CRASQSISSWLAWYQQKPGK<br>APKLLIYKASSLESGVPSRFSG<br>SGSGTEFTLTISSLQPDDFATY<br>YCEQYDSYPTFGGGTKVEIK<br>(SEQ ID NO: 58) |
| ADI-28200 | QVQLVQSGAEVKKPGSSVKVSCKA<br>SGGTFSSYAISWVRQAPGQGLEWM<br>GGIIPIFGTANYAQKFQGRVTITADE<br>STSTAYMELSSLRSEDTAVYYCAR<br>RGRKASGSFYYYYGMDVWGQGTT<br>VTVSS<br>(SEQ ID NO: 59)<br>CDR1 (SEQ ID NO: 324) -<br>GTFSSYAIS<br>CDR2 (SEQ ID NO: 325) -<br>GIIPIFGTANYAQKFQG<br>CDR3 (SEQ ID NO: 326) -<br>ARRGRKASGSFYYYYGMDV | DIVMTQSPDSLAVSLGERATIN<br>CESSQSLLNSGNQKNYLTWY<br>QQKPGQPPKPLIYWASTRESG<br>VPDRFSGSGSGTDFTLTISSLQ<br>AEDVAVYYCQNDYSYPYTFG<br>QGTKLEIK<br>(SEQ ID NO: 60)<br>CDR1 (SEQ ID NO: 327) -<br>ESSQSLLNSGNQKNYLT<br>CDR2 (SEQ ID NO: 328) -<br>WASTRES<br>CDR3 (SEQ ID NO: 329) -<br>QNDYSYPYT |
| ADI-29379 (E79) | QVQLVQSGAEVKKPGASVKVSCK<br>ASGYTFTSYYMHWVRQAPGQGLE<br>WMGIINPSGGSTSYAQKFQGRVTM<br>TRDTSTSTVYMELSSLRSEDTAVYY<br>CARGAPNYGDTTHDYYYMDVWG<br>KGTTVTVSS<br>(SEQ ID NO: 61)<br>CDR1 (SEQ ID NO: 63) -<br>YTFTSYYMH<br>CDR2 (SEQ ID NO: 64) -<br>IINPSGGSTSYAQKFQG<br>CDR3 (SEQ ID NO: 65) -<br>ARGAPNYGDTTHDYYYMDV | EIVMTQSPATLSVSPGERATLS<br>CRASQSVSSNLAWYQQKPGQ<br>APRLLIYGASTRATGIPARFSG<br>SGSGTEFTLTISSLQSEDFAVY<br>YCQQYDDWPFTFGGGTKVEI<br>K<br>(SEQ ID NO: 62)<br>CDR1 (SEQ ID NO: 66) -<br>RASQSVSSNLA<br>CDR2 (SEQ ID NO: 67) -<br>GASTRAT<br>CDR3 (SEQ ID NO: 68) -<br>QQYDDWPFT |
| ADI-29463 (F63) | QVQLVQSGAEVKKPGASVKVSCK<br>ASGYTFTGYYMHWVRQAPGQGLE<br>WMGWINPNSGGTNYAQKFQGRVT<br>MTRDTSISTAYMELSRLRSDDTAV<br>YYCARDTGEYYDTDDHGMDVWG<br>QGTTVTVSS<br>(SEQ ID NO: 69)<br>CDR1 (SEQ ID NO: 71) -<br>YTFTGYYMH<br>CDR2 (SEQ ID NO: 72) -<br>WINPNSGGTNYAQKFQG<br>CDR3 (SEQ ID NO: 73) -<br>ARDTGEYYDTDDHGMDV | EIVLTQSPGTLSLSPGERATLS<br>CRASQSVSSNLAWYQQKPGQ<br>APRLLIYGASTRATGIPARFSG<br>SGSGTEFTLTISSLQSEDFAVY<br>YCQQDDYWPPTFGGGTKVEI<br>K<br>(SEQ ID NO: 70)<br>CDR1 (SEQ ID NO: 74) -<br>RASQSVSSNLA<br>CDR2 (SEQ ID NO: 75) -<br>GASTRAT<br>CDR3 (SEQ ID NO: 76) -<br>QQDDYWPPT |
| ADI-27744 (A44) | EVQLLESGGGLVQPGGSLRLSCAAS<br>GFTFSSYAMSWVRQAPGKGLEWV<br>SAISGSGGSTYYADSVKGRFTISRD<br>NSKNTLYLQMNSLRAEDTAVYYC<br>AKDGGYYDSGAGDYWGQGTLVTV<br>SS<br>(SEQ ID NO: 77)<br>CDR1 (SEQ ID NO: 79) - FTFSSYAMS<br>CDR2 (SEQ ID NO: 80) -<br>AISGSGGSTYYADSVKG<br>CDR3 (SEQ ID NO: 81) -<br>AKDGGYYDSGAGDY | DIQMTQSPSSVSASVGDRVTIT<br>CRASQGIDSWLAWYQQKPGK<br>APKLLIYAASSLQSGVPSRFSG<br>SGSGTDFTLTISSLQPEDFATY<br>YCQQGVSYPRTFGGGTKVEIK<br>(SEQ ID NO: 78)<br>CDR1 (SEQ ID NO: 82) -<br>RASQGIDSWLA<br>CDR2 (SEQ ID NO: 83) -<br>AASSLQS<br>CDR3 (SEQ ID NO: 84) -<br>QQGVSYPRT |
| ADI-27749 (A49) | EVQLVESGGGLVKPGGSLRLSCAA<br>SGFTFSSYSMNWVRQAPGKGLEW<br>VSSISSSSSYIYYADSVKGRFTISRD<br>NAKNSLYLQMNSLRAEDTAVYYC<br>ARGAPMGAAAGWFDPWGQGTLVT<br>VSS<br>(SEQ ID NO: 85)<br>CDR1 (SEQ ID NO: 87) - FTFSSYSMN<br>CDR2 (SEQ ID NO: 88) -<br>SISSSSSYIYYADSVKG<br>CDR3 (SEQ ID NO: 89) -<br>ARGAPMGAAAGWFDP | DIQMTQSPSSVSASVGDRVTIT<br>CRASQGISSWLAWYQQKPGK<br>APKLLIYAASSLQSGVPSRFSG<br>SGSGTDFTLTISSLQPEDFATY<br>YCQQGVSFPRTFGGGTKVEIK<br>(SEQ ID NO: 86)<br>CDR1 (SEQ ID NO: 90) -<br>RASQGISSWLA<br>CDR2 (SEQ ID NO: 91) -<br>AASSLQS<br>CDR3 (SEQ ID NO: 92) -<br>QQGVSFPRT |

TABLE 1-continued

| Clones | Heavy chain variable region amino acid sequence | Light chain variable region amino acid sequence |
|---|---|---|
| ADI-29378 (E78) | QVQLVQSGAEVKKPGASVKVSCK ASGYTFTSYYMHWVRQAPGQGLE WMGIINPSGGSTSYAQKFQGRVTM TRDTSTSTVYMELSSLRSEDTAVYY CAREGAGFAYGMDYYYMDVWGK GTTVTVSS (SEQ ID NO: 93) CDR1 (SEQ ID NO: 95) - YTFTSYYMH CDR2 (SEQ ID NO: 96) - IINPSGGSTSYAQKFQG CDR3 (SEQ ID NO: 97) - AREGAGFAYGMDYYYMDV | EIVLTQSPATLSLSPGERATLS CRASQSVSSYLAWYQQKPGQ APRLLIYDASNRATGIPARFSG SGSGTDFTLTISSLEPEDFAVY YCQQSDNWPFTFGGGTKVEIK (SEQ ID NO: 94) CDR1 (SEQ ID NO: 98) - RASQSVSSYLA CDR2 (SEQ ID NO: 99) - DASNRAT CDR3 (SEQ ID NO: 100) - QQSDNWPFT |

Alternatively, a heavy chain variable domain represented by SEQ ID NO:101 can be paired with a light chain variable domain represented by SEQ ID NO:102 to form an antigen-binding site that can bind to NKG2D, as illustrated in U.S. Pat. No. 9,273,136.

SEQ ID NO: 101

QVQLVESGGGLVKPGGSLRLSCAASGFTFSSYGMHWVRQAPGKGLEWVAF

IRYDGSNKYYADSVKGRFTISRDNSKNTLYLQMNSLRAEDTAVYYCAKDR

GLGDGTYFDYWGQGTTVTVSS

SEQ ID NO: 102

QSALTQPASVSGSPGQSITISCSGSSSNIGNNAVNWYQQLPGKAPKLLIY

YDDLLPSGVSDRFSGSKSGTSAFLAISGLQSEDEADYYCAAWDDSLNGPV

FGGGTKLTVL

Alternatively, a heavy chain variable domain represented by SEQ ID NO:103 can be paired with a light chain variable domain represented by SEQ ID NO:104 to form an antigen-binding site that can bind to NKG2D, as illustrated in U.S. Pat. No. 7,879,985.

SEQ ID NO: 103

QVHLQESGPGLVKPSETLSLTCTVSDDSISSYYWSWIRQPPGKGLEWIGH

ISYSGSANYNPSLKSRVTISVDTSKNQFSLKLSSVTAADTAVYYCANWDD

AFNIWGQGTMVTVSS

SEQ ID NO: 104

EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPWTFG

QGTKVEIK

In one aspect, the present disclosure provides multi-specific binding proteins that bind to the NKG2D receptor and CD16 receptor on natural killer cells, and the antigen CD37. Table 2 lists some exemplary sequences of heavy chain variable domains and light chain variable domains that, in combination, can bind to CD37.

TABLE 2

| Clones | Heavy chain variable domain amino acid sequence | Light chain variable domain amino acid sequence |
|---|---|---|
| CD37 antibody (U.S. Pat. No. 8,333,966) | EVQLVQSGAEVKKPGESLKISCKG SGYSFTGYNMNWVRQMPGKGLE WMGNIDPYYGGTTYNRKFKGQVT ISADKSISTAYLQWSSLKASDTAM YYCARSVGPFDSWGQGTLVTVSSG (SEQ ID NO: 109) CDR1 (SEQ ID NO: 110) - GYSFTGY CDR2 (SEQ ID NO: 111) - DPYYGG CDR3 (SEQ ID NO: 112) - SVGPFDS | EIVLTQSPATLSLSPGER ATLSCRASENVYSYLAW YQQKPGQAPRLLIYFAK TLAEGIPARFSGSGSGTD FTLTISSLEPEDFAVYYC QHHSDNPWTFGQGTKV EIK (SEQ ID NO: 113) CDR1(SEQ ID NO: 114) - ENVYSYLA CDR2 (SEQ ID NO: 115) - FAKTLAE CDR3 (SEQ ID NO: 116) - QHHSDNPWT |
| CD37 antibody (U.S. Pat. No. 9,346,887) | QVQVQESGPGLVAPSQTLSITCTVS GFSLTTSGVSWVRQPPGKGLEWL GVIWGDGSTNYHPSLKSRLSIKKD HSKSQVFLKLNSLTAADTATYYCA KGGYSLAHWGQGTLVTVSSA (SEQ ID NO: 117) CDR1 (SEQ ID NO: 118) - FSLTTSGVS CDR2 (SEQ ID NO: 119) - VIWGDGSTNYHPSLKS | DIQMTQSPSSLSVSVGER VTITCRASENIRSNLAWY QQKPGKSPKLLVNVATN LADGVPSRFSGSGSGTD YSLKINSLQPEDFGTYYC QHYWGTTWTFGQGTKL EIKR (SEQ ID NO: 121) CDR1 (SEQ ID NO: 122) - ENIRSNLA |

TABLE 2-continued

| Clones | Heavy chain variable domain amino acid sequence | Light chain variable domain amino acid sequence |
|---|---|---|
| | CDR3 (SEQ ID NO: 120) - GGYSLAH | CDR2 (SEQ ID NO: 123) - NVATNLA<br>CDR3 (SEQ ID NO: 124) - QHYWGTTWT |
| CD37 antibody (U.S. patent appli-cation Ser. No. 14/447,209) | QVQLQQWGAGLLKPSETLSLTCA VYGGSFSPYYWSWIRQPPGKGLE WIGEINHSGSTNYNPSLKSRVTISV DTSKNQFSLKLSSVTAADTAVYYC ARRAGDFDYWGQGTLVTVSSA (SEQ ID NO: 125)<br>CDR1 (SEQ ID NO: 126) - GSFSPYYWS<br>CDR2 (SEQ ID NO: 127) - EINHSGSTNYNPSLKS<br>CDR3 (SEQ ID NO: 128) - RAGDFDY | DIQMTQSPSTLSASVGD RVTITCRASQSISSWLAW YQQKPGKAPKLLIYKAS SLESGVPSRFSGSGSGTE FTLTISSLQPDDFATYYC QQYNSYIFGQGTKLEIKR (SEQ ID NO: 129)<br>CDR1 (SEQ ID NO: 130) - RASQSISSWLA<br>CDR2 (SEQ ID NO: 131) - KASSLES<br>CDR3 (SEQ ID NO: 132) - QQYNSYI |

Alternatively, novel antigen-binding sites that can bind to CD37 can be identified by screening for binding to the amino acid sequence defined by SEQ ID NO:133.

SEQ ID NO: 133

```
MSAQESCLSLIKYFLFVFNLFFFVLGSLIFCFGIWILIDKTSFVSFVGL

AFVPLQIWSKVLAISGIFTMGIALLGCVGALKELRCLLGLYFGMLLLLF

ATQITLGILISTQRAQLERSLRDVVEKTIQKYGTNPEETAAEESWDYVQ
```

-continued

```
FQLRCCGWHYPQDWFQVLILRGNGSEAHRVPCSCYNLSATNDSTILDKV

ILPQLSRLGHLARSRHSADICAVPAESHIYREGCAQGLQKWLHNNLISI

VGICLGVGLLELGFMTLSIFLCRNLDHVYNRLARYR
```

In one aspect, the present disclosure provides multi-specific binding proteins that bind to the NKG2D receptor and CD16 receptor on natural killer cells, and the antigen CD20. Table 3 lists some exemplary peptide sequences of heavy chain variable domains and light chain variable domains that, in combination, can bind to CD20.

TABLE 3

| Clones | Heavy chain variable domain amino acid sequence | Light chain variable domain amino acid sequence |
|---|---|---|
| Rituximab | QVQLQQPGAELVKPGASVKMS CKASGYTFTSYNMHWVKQTPG RGLEWIGAIYPGNGDTSYNQKF KGKATLTADKSSSTAYMQLSSL TSEDSAVYYCARSTYYGGDWY FNVWGAGTTVTVSAA (SEQ ID NO: 134)<br>CDR1 (SEQ ID NO: 135) - GYTFTSY<br>CDR2 (SEQ ID NO: 136) - YPGNGD<br>CDR3 (SEQ ID NO: 137) - STYYGGDWYFNV | QIVLSQSPAILSASPGEKV TMTCRASSSVSYIHWFQQ KPGSSPKPWIYATSNLAS GVPVRFSGSGSGTSYSLTI SRVEAEDAATYYCQQWT SNPPTFGGGTKLEIKR (SEQ ID NO: 138)<br>CDR1(SEQ ID NO: 139) - SSVSYIH<br>CDR2 (SEQ ID NO: 140) - ATSNLAS<br>CDR3 (SEQ ID NO: 141) - QQWTSNPPT |
| Obinutuzumab | QVQLVQSGAEVKKPGSSVKVS CKASGYAFSYSWINWVRQAPG QGLEWMGRIFPGDGDTDYNGK FKGRVTITADKSTSTAYMELSSL RSEDTAVYYCARNVFDGYWLV YWGQGTLVTVSSA (SEQ ID NO: 142)<br>CDR1 (SEQ ID NO: 143) - GYAFSYS<br>CDR2 (SEQ ID NO: 144) - FPGDGD<br>CDR3 (SEQ ID NO: 145) - NVFDGYWLVY | DIVMTQTPLSLPVTPGEP ASISCRSSKSLLHSNGITY LYWYLQKPGQSPQLLIYQ MSNLVSGVPDRFSGSGSG TDFTLKISRVEAEDVGVY YCAQNLELPYTFGGGTK VEIKR (SEQ ID NO: 146)<br>CDR1 (SEQ ID NO: 147) - KSLLHSNGITYLY<br>CDR2 (SEQ ID NO: 148) - QMSNLVS<br>CDR3 (SEQ ID NO: 149) - QMSNLVS |
| Ofatumumab | EVQLVESGGGLVQPGRSLRLSC AASGFTFNDYAMHWVRQAPGK GLEWVSTISWNSGSIGYADSVK | EIVLTQSPATLSLSPGERA TLSCRASQSVSSYLAWY QQKPGQAPRLLIYDASNR |

TABLE 3-continued

| Clones | Heavy chain variable domain amino acid sequence | Light chain variable domain amino acid sequence |
|---|---|---|
| | GRFTISRDNAKKSLYLQMNSLR AEDTALYYCAKDIQYGNYYYG MDVWGQGTTVTVSSA (SEQ ID NO: 150) CDR1 (SEQ ID NO: 151) - GFTFNDY CDR2 (SEQ ID NO: 152) - SWNSGS CDR3 (SEQ ID NO: 153) - DIQYGNYYYGMDV | ATGIPARFSGSGSGTDFTL TISSLEPEDFAVYYCQQR SNWPITFGQGTRLEIKR (SEQ ID NO: 154) CDR1 (SEQ ID NO: 155) - QSVSSYLA CDR2 (SEQ ID NO: 156) - DASNRAT CDR3 (SEQ ID NO: 157) - QQRSNWPIT |
| Veltuzumab | QVQLQQSGAEVKKPGSSVKVS CKASGYTFTSYNMHWVKQAPG QGLEWIGAIYPGMGDTSYNQKF KGKATLTADESTNTAYMELSSL RSEDTAFYYCARSTYYGGDWY FDVWGQGTTVTVSSA (SEQ ID NO: 158) CDR1 (SEQ ID NO: 159) - GYTFTSY CDR2 (SEQ ID NO: 160) - YPGMGD CDR3 (SEQ ID NO: 161) - STYYGGDWYFDV | DIQLTQSPSSLSASVGDR VTMTCRASSSVSYIHWFQ QKPGKAPKPWIYATSNL ASGVPVRFSGSGSGTDYT FTISSLQPEDIATYYCQQ WTSNPPTFGGGTKLEIKR (SEQ ID NO: 162) CDR1 (SEQ ID NO: 163) - SSVSYIH CDR2 (SEQ ID NO: 164) - ATSNLAS CDR3 (SEQ ID NO: 165) - QQWTSNPPT |
| Ocrelizumab | EVQLVESGGGLVQPGGSLRLSC AASGYTFTSYNMHWVRQAPGK GLEWVGAIYPGNGDTSYNQKF KGRFTISVDKSKNTLYLQMNSL RAEDTAVYYCARVVYYSNSYW YFDVWGQGTLVTVSSA (SEQ ID NO: 166) CDR1 (SEQ ID NO: 167) - GYTFTSY CDR2 (SEQ ID NO: 168) - YPGNGD CDR3 (SEQ ID NO: 169) - VVYYSNSYWYFDV | DIQMTQSPSSLSASVGDR VTITCRASSSVSYMHWY QQKPGKAPKPLIYAPSNL ASGVPSRFSGSGSGTDFT LTISSLQPEDFATYYCQQ WSFNPPTFGQGTKVEIKR (SEQ ID NO: 170) CDR1 (SEQ ID NO: 171) - SSVSYMH CDR2 (SEQ ID NO: 172) - APSNLAS CDR3 (SEQ ID NO: 173) - QQWSFNPPT |

Alternatively, novel antigen-binding sites that can bind to CD20 can be identified by screening for binding to the amino acid sequence defined by SEQ ID NO:174.

SEQ ID NO: 174

MTTPRNSVNGTFPAEPMKGPIAMQSGPKPLFRRMSSLVGPTQSFFMRES

KTLGAVQIMNGLFHIALGGLLMIPAGIYAPICVTVWYPLWGGIMYIISG

SLLAATEKNSRKCLVKGKMIMNSLSLFAAISGMILSIMDILNIKISHFL

KMESLNFIRAHTPYINIYNCEPANPSEKNSPSTQYCYSIQSLFLGILSV

-continued

MLIFAFFQELVIAGIVENEWKRTCSRPKSNIVLLSAEEKKEQTIEIKEE

VVGLTETSSQPKNEEDIEIIPIQEEEEEETETNFPEPPQDQESSPIEND

SSP

In one aspect, the present disclosure provides multi-specific binding proteins that bind to the NKG2D receptor and CD16 receptor on natural killer cells, and the antigen CD19. Table 4 lists some exemplary peptide sequences of heavy chain variable domains and light chain variable domains that, in combination, can bind to CD19.

TABLE 4

| Clones | Heavy chain variable domain acid sequence | Light chain variable domain amino amino acid sequence |
|---|---|---|
| Blinatumomab | QVQLQQSGAELVRPGSSVKISC KASGYAFSSYWMNWVKQRPG QGLEWIGQIWPGDGDTNYNGK FKGKATLTADESSSTAYMQLSS LASEDSAVYFCARRETTTVGRY YYAMDYWGQGTTVTVSSG (SEQ ID NO: 175) CDR1 (SEQ ID NO: 176) - GYAFSSY CDR2 (SEQ ID NO: 177) - WPGDGD CDR3 (SEQ ID NO: 178) - RETTTVGRYYYAMDY | DIQLTQSPASLAVSLGQRA TISCKASQSVDYDGDSYL NWYQQIPGQPPKLLIYDAS NLVSGIPPRFSGSGSGTDF TLNIHPVEKVDAATYHCQ QSTEDPWTFGGGTKLEIK (SEQ ID NO: 179) CDR1(SEQ ID NO: 180) - QSVDYDGDSYLN CDR2 (SEQ ID NO: 181) - DASNLVS CDR3 (SEQ ID NO: 182) - QQSTEDPWT |

TABLE 4-continued

| Clones | Heavy chain variable domain acid sequence | Light chain variable domain amino amino acid sequence |
|---|---|---|
| Inebilizumab (U.S. Pat. No. 8,323,653) | EVQLVESGGGLVQPGGSLRLSC<br>AASGFTFSSSWMNWVRQAPGK<br>GLEWVGRIYPGDGDTNYNAKF<br>KGRFTISRDDSKNSLYLQMNSL<br>KTEDTAVYYCARSGFITTVRDF<br>DYWGQGTLVTVSS<br>(SEQ ID NO: 183)<br>CDR1 (SEQ ID NO: 184) -<br>GFTFSSS<br>CDR2 (SEQ ID NO: 185) -<br>YPGDGD<br>CDR3 (SEQ ID NO: 186) -<br>SGFITTVRDFDY | EIVLTQSPDFQSVTPKEKV<br>TITCRASESVDTFGISFMN<br>WFQQKPDQSPKLLIHEAS<br>NQGSGVPSRFSGSGSGTDF<br>TLTINSLEAEDAATYYCQ<br>QSKEVPFTFGGGTKVEIK<br>(SEQ ID NO: 187)<br>CDR1 (SEQ ID NO: 188) -<br>ESVDTFGISFMN<br>CDR2 (SEQ ID NO: 189) -<br>EASNQGS<br>CDR3 (SEQ ID NO: 190) -<br>QQSKEVPFT |
| CD19 antibody (U.S. Pat. No. 8,524,867) | EVQLVESGGGLVKPGGSLKLSC<br>AASGYTFTSYVMHWVRQAPGK<br>GLEWIGYINPYNDGTKYNEKFQ<br>GRVTISSDKSISTAYMELSSLRS<br>EDTAMYYCARGTYYYGTRVFD<br>YWGQGTLVTVSSA<br>(SEQ ID NO: 191)<br>CDR1 (SEQ ID NO: 192) -<br>GYTFTSY<br>CDR2 (SEQ ID NO: 193) -<br>NPYNDG<br>CDR3 (SEQ ID NO: 194) -<br>GTYYYGTRVFDY | DIVMTQSPATLSLSPGERA<br>TLSCRSSKSLQNVNGNTY<br>LYWFQQKPGQSPQLLIYR<br>MSNLNSGVPDRFSGSGSG<br>TEFTLTISSLEPEDFAVYYC<br>MQHLEYPITFGAGTKLEIKR<br>(SEQ ID NO: 195)<br>CDR1 (SEQ ID NO: 196) -<br>KSLQNVNGNTYLY<br>CDR2 (SEQ ID NO: 197) -<br>RMSNLNS<br>CDR3 (SEQ ID NO: 198)<br>MQHLEYPIT |
| CD19 antibody (U.S. Pat. No. 7,968,687) | QVQLQESGPGLVKPSQTLSLTC<br>TVSGGSISTSGMGVGWIRQHPG<br>KGLEWIGHIWWDDDKRYNPAL<br>KSRVTISVDTSKNQFSLKLSSVT<br>AADTAVYYCARMELWSYYFDY<br>WGQGTLVTVSS<br>(SEQ ID NO: 199)<br>CDR1 (SEQ ID NO: 200) -<br>GGSISTSGM<br>CDR2 (SEQ ID NO: 201) -<br>WWDDD<br>CDR3 (SEQ ID NO: 202) -<br>MELWSYYFDY | EIVLTQSPATLSLSPGERAT<br>LSCSASSSVSYMHWYQQK<br>PGQAPRLLIYDTSKLASGI<br>PARFSGSGSGTDFTLTISSL<br>EPEDVAVYYCFQGSVYPF<br>TFGQGTKLEIKR<br>(SEQ ID NO: 203)<br>CDR1 (SEQ ID NO: 204) -<br>SSVSYMH<br>CDR2 (SEQ ID NO: 205) -<br>DTSKLAS<br>CDR3 (SEQ ID NO: 206) -<br>FQGSVYPFT |

Alternatively, novel antigen-binding sites that can bind to CD19 can be identified by screening for binding to the amino acid sequence defined by SEQ ID NO:207.

SEQ ID NO: 207

MPPPRLLFFLLFLTPMEVRPEEPLVVKVEEGDNAVLQCLKGTSDGPTQQ

LTWSRESPLKPFLKLSLGLPGLGIHMRPLAIWLFIFNVSQQMGGFYLCQ

PGPPSEKAWQPGWTVNVEGSGELFRWNVSDLGGLGCGLKNRSSEGPSSP

SGKLMSPKLYVWAKDRPEIWEGEPPCLPPRDSLNQSLSQDLTMAPGSTL

WLSCGVPPDSVSRGPLSWTHVHPKGPKSLLSLELKDDRPARDMWVMETG

LLLPRATAQDAGKYYCHRGNLTMSFHLEITARPVLWHWLLRTGGWKVSA

-continued

VTLAYLIFCLCSLVGILHLQRALVLRRKRKRMTDPTRRFFKVTPPPGSG

PQNQYGNVLSLPTPTSGLGRAQRWAAGLGGTAPSYGNPSSDVQADGALG

SRSPPGVGPEEEEGEGYEEPDSEEDSEFYENDSNLGQDQLSQDGSGYEN

PEDEPLGPEDEDSFSNAESYENEDEELTQPVARTMDFLSPHGSAWDPSR

EATSLGSQSYEDMRGILYAAPQLRSIRGQPGPNHEEDADSYENMDNPDG

PDPAWGGGGRMGTWSTR

In one aspect, the present disclosure provides multi-specific binding proteins that bind to the NKG2D receptor and CD16 receptor on natural killer cells, and the antigen CD22. Table 5 lists some exemplary peptide sequences of heavy chain variable domains and light chain variable domains that, in combination, can bind to CD22.

TABLE 5

| Clones | Heavy chain variable domain amino acid sequence | Light chain variable domain amino acid sequence |
|---|---|---|
| Epratuzumab (U.S. Pat. No. 5,789,554) | QVQLVQSGAEVKKPGSSVKVSCK<br>ASGYTFTSYWLHWVRQAPGQGLE<br>WIGYINPRNDYTEYNQNFKDKATI<br>TADESTNTAYMELSSLRSEDTAFY<br>FCARRDITTFYWGQGTTVTVSS | DIQLTQSPSSLSASVGDRVT<br>MSCKSSQSVLYSANHKNY<br>LAWYQQKPGKAPKLLIYW<br>ASTRESGVPSRFSGSGSGT<br>DFTFTISSLQPEDIATYYCH |

TABLE 5-continued

| Clones | Heavy chain variable domain amino acid sequence | Light chain variable domain amino acid sequence |
|---|---|---|
| | (SEQ ID NO: 208)<br>CDR1 (SEQ ID NO: 209) - GYTFTSY<br>CDR2 (SEQ ID NO: 210) - NPRNDY<br>CDR3 (SEQ ID NO: 211) - RDITTFY | QYLSSWTFGGGTKLEIK<br>(SEQ ID NO: 212)<br>CDR1(SEQ ID NO: 213) - QSVLYSANHKNYLA<br>CDR2 (SEQ ID NO: 214) - WASTRES<br>CDR3 (SEQ ID NO: 215) - HQYLSSWT |
| Inotuzumab (U.S. Pat. No. 7,355,011) | QLVQSGAEVKKPGASVKVSCKASGYRFTNYWIHWVRQAPGQGLEWIGGINPGNNYATYRRKFQGRVTMTADTSTSTVYMELSSLRSEDTAVYYCTREGYGNYGAWFAYWGQGTLVTVSSA<br>(SEQ ID NO: 216)<br>CDR1 (SEQ ID NO: 217) - GYRFTNY<br>CDR2 (SEQ ID NO: 218) - NPGNNY<br>CDR3 (SEQ ID NO: 219) - EGYGNYGAWFAY | DVQVTQSPSSLSASVGDRVTITCRSSQSLANSYGNTFLSWYLHKPGKAPQLLIYGISNRFSGVPDRFSGSGSGTDFTLTISSLQPEDFATYYCLQGTHQPYTFGQGTKVEIKR<br>(SEQ ID NO: 220)<br>CDR1 (SEQ ID NO: 221) - QSLANSYGNTFLS<br>CDR2 (SEQ ID NO: 222) - GISNRFS<br>CDR3 (SEQ ID NO: 223) - LQGTHQPYT |
| Pinatuzumab (U.S. Pat. No. 8,394,607) | EVQLVESGGGLVQPGGSLRLSCAASGYEFSRSWMNWVRQAPGKGLEWVGRIYPGDGDTNYSGKFKGRFTISADTSKNTAYLQMNSLRAEDTAVYYCARDGSSWDWYFDVWGQGTLVTVSSA<br>(SEQ ID NO: 224)<br>CDR1 (SEQ ID NO: 225) - GYEFSRS<br>CDR2 (SEQ ID NO: 226) - YPGDGD<br>CDR3 (SEQ ID NO: 227) - DGSSWDWYFDV | DIQMTQSPSSLSASVGDRVTITCRSSQSIVHSVGNTFLEWYQQKPGKAPKLLIYKVSNRFSGVPSRFSGSGSGTDFTLTISSLQPEDFATYYCFQGSQFPYTFGQGTKVEIKR<br>(SEQ ID NO: 228)<br>CDR1 (SEQ ID NO: 229) - QSIVHSVGNTFLE<br>CDR2 (SEQ ID NO: 230) - KVSNRFS<br>CDR3 (SEQ ID NO: 231) - FQGSQFPYT |

Antigen-binding sites that bind to CD22 can be identified by screening for binding to the amino acid sequence defined by SEQ ID NO:232.

SEQ ID NO: 232

```
MHLLGPWLLLLVLEYLAFSDSSKWVFEHPETLYAWEGACVWIPCTYRAL
DGDLESFILFHNPEYNKNTSKFDGTRLYESTKDGKVPSEQKRVQFLGDK
NKNCTLSIHPVHLNDSGQLGLRMESKTEKWMERIHLNVSERPFPPHIQL
PPEIQESQEVTLTCLLNFSCYGYPIQLQWLLEGVPMRQAAVTSTSLTIK
SVFTRSELKFSPQWSHHGKIVTCQLQDADGKFLSNDTVQLNVKHTPKLE
IKVTPSDAIVREGDSVTMTCEVSSSNPEYTTVSWLKDGTSLKKQNTFTL
NLREVTKDQSGKYCCQVSNDVGPGRSEEVFLQVQYAPEPSTVQILHSPA
VEGSQVEFLCMSLANPLPTNYTWYHNGKEMQGRTEEKVHIPKILPWHAG
TYSCVAENILGTGQRGPGAELDVQYPPKKVTTVIQNPMPIREGDTVTLS
```

-continued

```
CNYNSSNPSVTRYEWKPHGAWEEPSLGVLKIQNVGWDNTTIACAACNSW
CSWASPVALNVQYAPRDVRVRKIKPLSEIHSGNSVSLQCDFSSSHPKEV
QFFWEKNGRLLGKESQLNFDSISPEDAGSYSCWVNNSIGQTASKAWTLE
VLYAPRRLRVSMSPGDQVMEGKSATLTCESDANPPVSHYTWFDWNNQSL
PYHSQKLRLEPVKVQHSGAYWCQGTNSVGKGRSPLSTLTVYYSPETIGR
RVAVGLGSCLAILILAICGLKLQRRWKRTQSQQGLQENSSGQSFFVRNK
KVRRAPLSEGPHSLGCYNPMMEDGISYTTLRFPEMNIPRTGDAESSEMQ
RPPPDCDDTVTYSALHKRQVGDYENVIPDFPEDEGIHYSELIQFGVGER
PQAQENVDYVILKH
```

In one aspect, the present disclosure provides multi-specific binding proteins that bind to the NKG2D receptor and CD16 receptor on natural killer cells, and the antigen CD30. Table 6 lists some exemplary peptide sequences of heavy chain variable domains and light chain variable domains that, in combination, can bind to CD30.

TABLE 6

| Clones | Heavy chain variable domain amino acid sequence | Light chain variable domain amino acid sequence |
|---|---|---|
| CD30 antibody (U.S. Pat. No. 7,090,843) | QIQLQQSGPEVVKPGASVKISCKASGYTFTDYYITWVKQKPGQGLEWIGWIYPGSGNTKYNEKFKGKATLTVDTSSSTAFMQLSSLTSEDTAVYFCANYGNYWFAYWGQGTQVTVSAA | DIVLTQSPASLAVSLGQRATISCKASQSVDFDGDSYMNWYQQKPGQPPKVLIYAASNLESGIPARFSGSGSGTDFTLNIHPVEEEDAATYYCQQS |

TABLE 6-continued

| Clones | Heavy chain variable domain amino acid sequence | Light chain variable domain amino acid sequence |
|---|---|---|
| | (SEQ ID NO: 233)<br>CDR1 (SEQ ID NO: 234) - GYTFTDYYIT<br>CDR2 (SEQ ID NO: 235) - YPGSGN<br>CDR3 (SEQ ID NO: 236) - YGNYWFAY | NEDPWTFGGGTKLEIKR<br>(SEQ ID NO: 237)<br>CDR1(SEQ ID NO: 238) - QSVDFDGDSYMN<br>CDR2 (SEQ ID NO: 239) - AASNLES<br>CDR3 (SEQ ID NO: 240) - QQSNEDPWT |
| CD30 antibody (WO2016177846) | QVQLQQSGAELARPGASVKMSCKASGYTFTTYTIHWVRQRPGHDLEWIGYINPSSGYSDYNQNFKGKTTLTADKSSNTAYMQLNSLTSEDSAVYYCARRADYGNYEYTWFAYWGQGTTVTVSS<br>(SEQ ID NO: 241)<br>CDR1 (SEQ ID NO: 242) - GYTFTTYTIH<br>CDR2 (SEQ ID NO: 243) - YINPSSGYSDYNQNFKG<br>CDR3 (SEQ ID NO: 244) - RADYGNYEYTWFAY | DIVMTQSPKFMSTSVGDRVTVTCKASQNVGTNVAWFQQKPGQSPKVLIYSASYRYSGVPDRFTGSGSGTDFTLTISNVQSEDLAEYFCQQYHTYPLTFGGGTKLEIN<br>(SEQ ID NO: 245)<br>CDR1 (SEQ ID NO: 246) - QNVGTNVA<br>CDR2 (SEQ ID NO: 247) - SASYRYS<br>CDR3 (SEQ ID NO: 248) - QQYHTYPLT |
| CD 30 antibody (U.S. Pat. No. 8,207,303) | QVQLQQWGAGLLKPSETLSLTCAVYGGSFSAYYWSWIRQPPGKGLEWIGDINHGGGTNYNPSLKSRVTISVDTSKNQFSLKLNSVTAADTAVYYCASLTAYWGQGSLVTVSS<br>(SEQ ID NO: 249)<br>CDR1 (SEQ ID NO: 250) - AYYWS<br>CDR2 (SEQ ID NO: 251) - DINHGGGTNYNPSLKS<br>CDR3 (SEQ ID NO: 252) - LTAY | DIQMTQSPTSLSASVGDRVTITCRASQGISSWLTWYQQKPEKAPKSLIYAASSLQSGVPSRFSGSGSGTDFTLTISSLQPEDFATYYCQQYDSYPITFGQGTRLEIK<br>(SEQ ID NO: 253)<br>CDR1 (SEQ ID NO: 254) - RASQGISSWLT<br>CDR2 (SEQ ID NO: 255) - AASSLQS<br>CDR3 (SEQ ID NO: 256) - QQYDSYPIT |
| CD 30 antibody (U.S. Pat. No. 8,207,303) | EVQLVESGGGLVQPGGSLRLSCVASGFTFSNSWMSWVRQAPGKGLEWVANINEDGSEKFYVDSVKGRFTFSRDNAENSLYLQMNSLRAEDTAVYYCARVHWYFHLWGRGTLVTVSS<br>(SEQ ID NO: 257)<br>CDR1 (SEQ ID NO: 258) - NSWMS<br>CDR2 (SEQ ID NO: 259) - NINEDGSEKFYVDSVKG<br>CDR3 (SEQ ID NO: 260) - VHWYFHL | EIVLTQSPGTLSLSPGERATLSCRASQSVSSSYLAWYQQKPGQAPRLLIYGASSRATGIPDRFSGSGSGTDFTLTISSLEPEDFAVYYCQQYGSSPWTFGQGTKVEIK<br>(SEQ ID NO: 261)<br>CDR1 (SEQ ID NO: 262) - RASQSVSSSYLA<br>CDR2 (SEQ ID NO: 263) - GASSRAT<br>CDR3 (SEQ ID NO: 264) - QQYGSSPWT |
| CD 30 antibody (U.S. Pat. No. 8,207,303) | QVQLQQWGAGLLKPSETLSLTCAVYGGSFSGYYWSWIRQPPGKGLEWIGEINHSGSTKYTPSLKSRVTISVDTSKHQFSLKLSSVTAADTAVYYCARETVYYFDLWGRGTLVTVSS<br>(SEQ ID NO: 265)<br>CDR1 (SEQ ID NO: 266) - GYYWS<br>CDR2 (SEQ ID NO: 267) - EINHSGSTKYTPSLKS<br>CDR3 (SEQ ID NO: 268) - ETVYYFDL | EIVLTQSPATLSLSPGERATLSCRASQSVSSNLAWYQQKPGQAPRLLIYDASNRATGIPARLSGSGSGTDFTLTISSLEPEDFAVYYCQQRSNWPWTFGQGTKVEIK<br>(SEQ ID NO: 269)<br>CDR1 (SEQ ID NO: 270) - RASQSVSSNLA<br>CDR2 (SEQ ID NO: 271) - DASNRAT<br>CDR3 (SEQ ID NO: 272) - QQRSNWPWT |

Alternatively, novel antigen-binding sites that can bind to CD30 can be identified by screening for binding to the amino acid sequence defined by SEQ ID NO:273.

SEQ ID NO: 273
MRVLLAALGLLFLGALRAFPQDRPFEDTCHGNPSHYYDKAVRRCCYRCP

MGLFPTQQCPQRPTDCRKQCEPDYYLDEADRCTACVTCSRDDLVEKTPC

-continued

AWNSSRVCECRPGMFCSTSAVNSCARCFFHSVCPAGMIVKFPGTAQKNT

VCEPASPGVSPACASPENCKEPSSGTIPQAKPTPVSPATSSASTMPVRG

GTRLAQEAASKLTRAPDSPSSVGRPSSDPGLSPTQPCPEGSGDCRKQCE

PDYYLDEAGRCTACVSCSRDDLVEKTPCAWNSSRTCECRPGMICATSAT

-continued

NSCARCVPYPICAAETVTKPQDMAEKDTTFEAPPLGTQPDCNPTPENGE

APASTSPTQSLLVDSQASKTLPIPTSAPVALSSTGKPVLDAGPVLFWVI

LVLVVVVGSSAFLLCHRRACRKRIRQKLHLCYPVQTSQPKLELVDSRPR

RSSTQLRSGASVTEPVAEERGLMSQPLMETCHSVGAAYLESLPLQDASP

AGGPSSPRDLPEPRVSTEHTNNKIEKIYIMKADTVIVGTVKAELPEGRG

LAGPAEPELEEELEADHTPHYPEQETEPPLGSCSDVMLSVEEEGKEDPL

PTAASGK

In one aspect, the present disclosure provides multi-specific binding proteins that bind to the NKG2D receptor and CD16 receptor on natural killer cells, and the antigen CD52. Table 7 lists some exemplary peptide sequences of heavy chain variable domains and light chain variable domains that, in combination, can bind to CD52.

TABLE 7

| Clones | Heavy chain variable domain amino acid sequence | Light chain variable domain amino acid sequence |
|---|---|---|
| CD52 antibody (U.S. Pat. No. 5,846,534) | QVQLQESGPGLVRPSQTLSLTCTV SGFTFTDFYMNWVRQPPGRGLEW IGFIRDKAKGYTTEYNPSVKGRVT MLVDTSKNQFSLRLSSVTAADTAV YYCAREGHTAAPFDYWGQGSLVT VSSA (SEQ ID NO: 274)<br>CDR1 (SEQ ID NO: 275) - GFTFTDF<br>CDR2 (SEQ ID NO: 276) - RDKAKGYT<br>CDR3 (SEQ ID NO: 277) - EGHTAAPFDY | DIQMTQSPSSLSASVGDRV TITCKASQNIDKYLNWYQQ KPGKAPKLLIYNTNNLQTG VPSRFSGSGSGTDFTFTISSL QPEDIATYYCLQHISRPRTF GQGTKVEIKR (SEQ ID NO: 278)<br>CDR1(SEQ ID NO: 279) - QNIDKYLN<br>CDR2 (SEQ ID NO: 280) - NTNNLQT<br>CDR3 (SEQ ID NO: 281) - LQHISRPRT |
| CD52 antibody (U.S. Pat. No. 9,321,841) | EVHLVESGGGLVQPGGSLRLSCAA SGFTFSRYGMSWVRQAPGKGLEL VAMMKTKGGRTYYPDSVKGRFTI SRDNAKNSLYLQMNSLRAEDTAIY YCASDGYYWGQGTTVTVSS (SEQ ID NO: 282)<br>CDR1 (SEQ ID NO: 283) - RYGMS<br>CDR2 (SEQ ID NO: 284) - MMKTKGGRTYYPDSVKG<br>CDR3 (SEQ ID NO: 285) - DGYY | DVVMTQTPLSLSVTLGQPA SISCKSSQSLLHSDGKTYLN WLQQRPGQSPRRLIYLVSK LDSGVPDRFSGSGSGTDFT LKISRVEAEDVGIYYCWQG THLWTFGGGTKVEIK (SEQ ID NO: 286)<br>CDR1 (SEQ ID NO: 287) - KSSQSLLHSDGKTYLN<br>CDR2 (SEQ ID NO: 288) - LVSKLDS<br>CDR3 (SEQ ID NO: 289) - WQGTHLWT |

Alternatively, novel antigen-binding sites that can bind to CD52 can be identified by screening for binding to the amino acid sequence defined by SEQ ID NO:290.

SEQ ID NO: 290

MRVLLAALGLLFLGALRAFPQDRPFEDTCHGNPSHYYDKAVRRCCYRCP

MGLFPTQQCPQRPTDCRKQCEPDYYLDEADRCTACVTCSRDDLVEKTPC

AWNSSRVCECRPGMFCSTSAVNSCARCFFHSVCPAGMIVKFPGTAQKNT

VCEPASPGVSPACASPENCKEPSSGTIPQAKPTPVSPATSSASTMPVRG

GTRLAQEAASKLTRAPDSPSSVGRPSSDPGLSPTQPCPEGSGDCRKQCE

PDYYLDEAGRCTACVSCSRDDLVEKTPCAWNSSRTCECRPGMICATSAT

NSCARCVPYPICAAETVTKPQDMAEKDTTFEAPPLGTQPDCNPTPENGE

APASTSPTQSLLVDSQASKTLPIPTSAPVALSSTGKPVLDAGPVLFWVI

-continued

LVLVVVVGSSAFLLCHRRACRKRIRQKLHLCYPVQTSQPKLELVDSRPR

RSSTQLRSGASVTEPVAEERGLMSQPLMETCHSVGAAYLESLPLQDASP

AGGPSSPRDLPEPRVSTEHTNNKIEKIYIMKADTVIVGTVKAELPEGRG

LAGPAEPELEEELEADHTPHYPEQETEPPLGSCSDVMLSVEEEGKEDPL

PTAASGK

In one aspect, the present disclosure provides multi-specific binding proteins that bind to the NKG2D receptor and CD16 receptor on natural killer cells, and the antigen CD133. Table 8 lists some exemplary peptide sequences of heavy chain variable domains and light chain variable domains that, in combination, can bind to CD133.

TABLE 8

| Clones | Heavy chain variable domain amino acid sequence | Light chain variable domain amino acid sequence |
|---|---|---|
| CD133 antibody (U.S. Pat. No. 8,722,858) | MDWTWSILFLVAAATGAHSQVQL VQSGAEVKKPGASVKVSCKASGY TFTDFEMHWVRQAPGQGLEWMG DIDPGTGDTAYNLKFKGRVTMTT DTSTSTAYMELRSLRSDDTAVYYC ALGAFVYWGQGTLVTVSS (SEQ ID NO: 291) CDR1 (SEQ ID NO: 292) - DFEMH CDR2 (SEQ ID NO: 293) - DIDPGTGDTAYNLKFKG CDR3 (SEQ ID NO: 294) - GAFVY | MKYLLPTAAAGLLLLAAQ PAMADVVMTQSPLSLPVTF GEPASISCRSSQSLANSYGN TYLSWYLQKPGQSPQLLIY GISNRFSGVPDRFSGSGSGT DFTLKISRVEAEDVGVYYC LQGTHQPYTFGQGTKLEIK (SEQ ID NO: 295) CDR1 (SEQ ID NO: 296) - RSSQSLANSYGNTYLS CDR2 (SEQ ID NO: 297) - GISNRFS CDR3 (SEQ ID NO: 298) - LQGTHQPYT |
| CD133 anyibody (U.S. Pat. No. 8,722,858) | MDWTWSILFLVAAATGAHSQVQL VQSGAEVKKPGASVKVSCKASGY TFTDFEMHWVRQAPGQGLEWMG DIDPGTGDTAYNLKFKGRVTMTT DTSTSTAYMELRSLRSDDTAVYYC ALGAFVYWGQGTLVTVSS (SEQ ID NO: 299) CDR1 (SEQ ID NO: 300) - DFEMH CDR2 (SEQ ID NO: 301) - DIDPGTGDTAYNLKFKG CDR3 (SEQ ID NO: 302) - GAFVY | MKYLLPTAAAGLLLLAAQ PAMADVVMTQSPLSLPVTF GEQASISCRSSQSLANSYG NTYLSWYLQKPGQSPQLLI YGISNRFSGVPDRFSGSGSG TDFTLKISRVEAEDVGVYY CLQGTHQPYTFGQGTKLEIK (SEQ ID NO: 303) CDR1 (SEQ ID NO: 304) - RSSQSLANSYGNTYLS CDR2 (SEQ ID NO: 305) - GISNRFS CDR3 (SEQ ID NO: 306) - LQGTHQPYT |
| CD133 antibody (WO2016154623) | METGLRWLLLVAVLKGVQCQSVE ESGGRLVTPGTPLTLTCTVSGIDLN NYNMQWVRQAPGKGLEWIGATF GSDSIYYATWAKGRFTISKTSTTV DLKMTSLTTEDTATYFCARGGLW GPGTLVTVSS (SEQ ID NO: 307) CDR1 (SEQ ID NO: 308) - GIDLNNYNMQ CDR2 (SEQ ID NO: 309) - ATFGSDSIYYATWA CDR3 (SEQ ID NO: 310) - GGL | MDTRAPTQLLGLLLLWLP GVTFAQVLTQTASPVSAAV GATVTINCQSSQSVYNNNY LAWFQQKPGQPPKLLIYRA STLASGVSSRFKGSGSGTQ FALTISGVQCDDAGTYYCQ GEFSCDSADCAAFGGGTEV VVKG (SEQ ID NO: 311) CDR1 (SEQ ID NO: 312) - QSSQSVYNNNYL CDR2 (SEQ ID NO: 313) - RASTLAS CDR3 (SEQ ID NO: 314) - QGEFSCDSADCAA |
| CD133 antibody (WO2016154623) | METGLRWLLLVAVLKGVQCQSVE ESGGRLVTPGTPLTLTCTVSGFSLS RYAMSWVRQAPGKGLDWIGYIDI GGGAYYASWAKGRFTISETSTTVY LKVNSPTTEDTATYFCARGVANSD IWGPGTLVTVSS (SEQ ID NO: 315) CDR1 (SEQ ID NO: 316) - GFSLSRYAMS CDR2 (SEQ ID NO: 317) - YIDIGGGAYYASWA CDR3 (SEQ ID NO: 318) - GVANSDI | MDTRAPTQLLGLLLLWLP GARCALVMTQTPSPVSAA VGGTVTINCQSSQSVFNNK WLSWYQQKPGQPPKLLIYF VSTLASGVPSRFKGSGSGT QFTLTISGVQCDDAATYYC QGSDYSSGWYSPFGGGTE VVVEG (SEQ ID NO: 319) CDR1 (SEQ ID NO: 320) - QSSQSVFNNKWLS CDR2 (SEQ ID NO: 321) - FVSTLAS CDR3 (SEQ ID NO: 322) - QGSDYSSGWYSP |

Alternatively, novel antigen-binding sites that can bind to CD133 can be identified by screening for binding to the amino acid sequence defined by SEQ ID NO:323.

SEQ ID NO: 323

MALVLGSLLLLGLCGNSFSGGQPSSTDAPKAWNYELPATNYETQDSHKA

GPIGILFELVHIFLYVVQPRDFPEDTLRKFLQKAYESKIDYDKPETVIL

GLKIVYYEAGIILCCVLGLLFIILMPLVGYFFCMCRCCNKCGGEMHQRQ

-continued

KENGPFLRKCFAISLLVICIIISIGIFYGFVANHQVRTRIKRSRKLADS

NFKDLRTLLNETPEQIKYILAQYNTTKDKAFTDLNSINSVLGGGILDRL

RPNIIPVLDEIKSMATAIKETKEALENMNSTLKSLHQQSTQLSSSLTSV

KTSLRSSLNDPLCLVHPSSETCNSIRLSLSQLNSNPELRQLPPVDAELD

NVNNVLRTDLDGLVQQGYQSLNDIPDRVQRQTTTVVAGIKRVLNSIGSD

IDNVTQRLPIQDILSAFSVYVNNTESYIHRNLPTLEEYDSYWWLGGLVI

-continued

```
CSLLTLIVIFYYLGLLCGVCGYDRHATPTTRGCVSNTGGVFLMVGVGLS

FLFCWILMIIVVLTFVFGANVEKLICEPYTSKELFRVLDTPYLLNEDWE

YYLSGKLFNKSKMKLTFEQVYSDCKKNRGTYGTLHLQNSFNISEHLNIN

EHTGSISSELESLKVNLNIFLLGAAGRKNLQDFAACGIDRMNYDSYLAQ

TGKSPAGVNLLSFAYDLEAKANSLPPGNLRNSLKRDAQTIKTIHQQRVL

PIEQSLSTLYQSVKILQRTGNGLLERVTRILASLDFAQNFITNNTSSVI

IEETKKYGRTIIGYFEHYLQWIEFSISEKVASCKPVATALDTAVDVFLC

SYIIDPLNLFWFGIGKATVFLLPALIFAVKLAKYYRRMDSEDVYDDVET

IPMKNMENGNNGYHKDHVYGIHNPVMTSPSQH
```

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al., Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

The assembly of heterodimeric antibody heavy chains can be accomplished by expressing two different antibody heavy chain sequences in the same cell, which may lead to the assembly of homodimers of each antibody heavy chain as well as assembly of heterodimers. Promoting the preferential assembly of heterodimers can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, and U.S. Ser. No. 14/830,336. For example, mutations can be made in the CH3 domain based on human IgG1 and incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain of the invention can optionally be coupled to an amino acid sequence at least 90% identical to an antibody constant region, such as an IgG constant region including hinge, CH2 and CH3 domains with or without CH1 domain. In some embodiments, the amino acid sequence of the constant region is at least 90% identical to a human antibody constant region, such as an human IgG1 constant region, an IgG2 constant region, IgG3 constant region, or IgG4 constant region. In some other embodiments, the amino acid sequence of the constant region is at least 90% identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the Cκ of a human IgG1 constant region may be at amino acid E123, F116, S176, V163, S174, and/or T164.

Alternatively, amino acid substitutions could be selected from the following sets of substitutions shown in Table 9.

TABLE 9

| | First Polypeptide | Second Polypeptide |
|---|---|---|
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 10.

TABLE 10

| | First Polypeptide | Second Polypeptide |
|---|---|---|
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 11.

TABLE 11

| | First Polypeptide | Second Polypeptide |
|---|---|---|
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 12.

TABLE 12

| First Polypeptide | Second Polypeptide |
|---|---|
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitutions could be selected from the following set of substitutions in Table 13, where the position(s) indicated in the First Polypeptide column is replaced by any known negatively-charged amino acid, and the position(s) indicated in the Second Polypeptide Column is replaced by any known positively-charged amino acid.

TABLE 13

| First Polypeptide | Second Polypeptide |
|---|---|
| K392, K370, K409, or K439 | D399, E356, or E357 |

Alternatively, at least one amino acid substitutions could be selected from the following set of in Table 14, where the position(s) indicated in the First Polypeptide column is replaced by any known positively-charged amino acid, and the position(s) indicated in the Second Polypeptide Column is replaced by any known negatively-charged amino acid.

TABLE 14

| First Polypeptide | Second Polypeptide |
|---|---|
| D399, E356, or E357 | K409, K439, K370, or K392 |

Alternatively, amino acid substitutions could be selected from the following set in Table 15.

TABLE 15

| First Polypeptide | Second Polypeptide |
|---|---|
| T350V, L351Y, F405A, and Y407V | T350V, T366L, K392L, and T394W |

Alternatively, or in addition, the structural stability of a hetero-multimeric protein may be increased by introducing S354C on either of the first or second polypeptide chain, and Y349C on the opposing polypeptide chain, which forms an artificial disulfide bridge within the interface of the two polypeptides.

In some embodiments, the amino acid sequence of one polypeptide chain of the antibody constant region differs from the amino acid sequence of an IgG1 constant region at position T366, and wherein the amino acid sequence of the other polypeptide chain of the antibody constant region differs from the amino acid sequence of an IgG1 constant region at one or more positions selected from the group consisting of T366, L368 and Y407.

In some embodiments, the amino acid sequence of one polypeptide chain of the antibody constant region differs from the amino acid sequence of an IgG1 constant region at one or more positions selected from the group consisting of T366, L368 and Y407, and wherein the amino acid sequence of the other polypeptide chain of the antibody constant region differs from the amino acid sequence of an IgG1 constant region at position T366.

In some embodiments, the amino acid sequence of one polypeptide chain of the antibody constant region differs from the amino acid sequence of an IgG1 constant region at one or more positions selected from the group consisting of E357, K360, Q362, S364, L368, K370, T394, D401, F405, and T411 and wherein the amino acid sequence of the other polypeptide chain of the antibody constant region differs from the amino acid sequence of an IgG1 constant region at one or more positions selected from the group consisting of Y349, E357, S364, L368, K370, T394, D401, F405 and T411.

In some embodiments, the amino acid sequence of one polypeptide chain of the antibody constant region differs from the amino acid sequence of an IgG1 constant region at one or more positions selected from the group consisting of Y349, E357, S364, L368, K370, T394, D401, F405 and T411 and wherein the amino acid sequence of the other polypeptide chain of the antibody constant region differs from the amino acid sequence of an IgG1 constant region at one or more positions selected from the group consisting of E357, K360, Q362, S364, L368, K370, T394, D401, F405, and T411.

In some embodiments, the amino acid sequence of one polypeptide chain of the antibody constant region differs from the amino acid sequence of an IgG1 constant region at one or more positions selected from the group consisting of L351, D399, S400 and Y407 and wherein the amino acid sequence of the other polypeptide chain of the antibody constant region differs from the amino acid sequence of an IgG1 constant region at one or more positions selected from the group consisting of T366, N390, K392, K409 and T411.

In some embodiments, the amino acid sequence of one polypeptide chain of the antibody constant region differs from the amino acid sequence of an IgG1 constant region at one or more positions selected from the group consisting of T366, N390, K392, K409 and T411 and wherein the amino acid sequence of the other polypeptide chain of the antibody constant region differs from the amino acid sequence of an IgG1 constant region at one or more positions selected from the group consisting of L351, D399, S400 and Y407.

In some embodiments, the amino acid sequence of one polypeptide chain of the antibody constant region differs from the amino acid sequence of an IgG1 constant region at one or more positions selected from the group consisting of Q347, Y349, K360, and K409, and wherein the amino acid sequence of the other polypeptide chain of the antibody constant region differs from the amino acid sequence of an IgG1 constant region at one or more positions selected from the group consisting of Q347, E357, D399 and F405.

In some embodiments, the amino acid sequence of one polypeptide chain of the antibody constant region differs from the amino acid sequence of an IgG1 constant region at one or more positions selected from the group consisting of Q347, E357, D399 and F405, and wherein the amino acid sequence of the other polypeptide chain of the antibody constant region differs from the amino acid sequence of an IgG1 constant region at one or more positions selected from the group consisting of Y349, K360, Q347 and K409.

In some embodiments, the amino acid sequence of one polypeptide chain of the antibody constant region differs from the amino acid sequence of an IgG1 constant region at one or more positions selected from the group consisting of K370, K392, K409 and K439, and wherein the amino acid sequence of the other polypeptide chain of the antibody constant region differs from the amino acid sequence of an IgG1 constant region at one or more positions selected from the group consisting of D356, E357 and D399.

In some embodiments, the amino acid sequence of one polypeptide chain of the antibody constant region differs from the amino acid sequence of an IgG1 constant region at one or more positions selected from the group consisting of D356, E357 and D399, and wherein the amino acid sequence of the other polypeptide chain of the antibody constant region differs from the amino acid sequence of an IgG1 constant region at one or more positions selected from the group consisting of K370, K392, K409 and K439.

In some embodiments, the amino acid sequence of one polypeptide chain of the antibody constant region differs from the amino acid sequence of an IgG1 constant region at one or more positions selected from the group consisting of L351, E356, T366 and D399, and wherein the amino acid sequence of the other polypeptide chain of the antibody constant region differs from the amino acid sequence of an IgG1 constant region at one or more positions selected from the group consisting of Y349, L351, L368, K392 and K409.

In some embodiments, the amino acid sequence of one polypeptide chain of the antibody constant region differs from the amino acid sequence of an IgG1 constant region at one or more positions selected from the group consisting of Y349, L351, L368, K392 and K409, and wherein the amino acid sequence of the other polypeptide chain of the antibody constant region differs from the amino acid sequence of an IgG1 constant region at one or more positions selected from the group consisting of L351, E356, T366 and D399.

In some embodiments, the amino acid sequence of one polypeptide chain of the antibody constant region differs from the amino acid sequence of an IgG1 constant region by an S354C substitution and wherein the amino acid sequence of the other polypeptide chain of the antibody constant region differs from the amino acid sequence of an IgG1 constant region by a Y349C substitution.

In some embodiments, the amino acid sequence of one polypeptide chain of the antibody constant region differs from the amino acid sequence of an IgG1 constant region by a Y349C substitution and wherein the amino acid sequence of the other polypeptide chain of the antibody constant region differs from the amino acid sequence of an IgG1 constant region by an S354C substitution.

In some embodiments, the amino acid sequence of one polypeptide chain of the antibody constant region differs from the amino acid sequence of an IgG1 constant region by K360E and K409W substitutions and wherein the amino acid sequence of the other polypeptide chain of the antibody constant region differs from the amino acid sequence of an IgG1 constant region by O347R, D399V and F405T substitutions.

In some embodiments, the amino acid sequence of one polypeptide chain of the antibody constant region differs from the amino acid sequence of an IgG1 constant region by O347R, D399V and F405T substitutions and wherein the amino acid sequence of the other polypeptide chain of the antibody constant region differs from the amino acid sequence of an IgG1 constant region by K360E and K409W substitutions.

In some embodiments, the amino acid sequence of one polypeptide chain of the antibody constant region differs from the amino acid sequence of an IgG1 constant region by a T366W substitutions and wherein the amino acid sequence of the other polypeptide chain of the antibody constant region differs from the amino acid sequence of an IgG1 constant region by T366S, T368A, and Y407V substitutions.

In some embodiments, the amino acid sequence of one polypeptide chain of the antibody constant region differs from the amino acid sequence of an IgG1 constant region by T366S, T368A, and Y407V substitutions and wherein the amino acid sequence of the other polypeptide chain of the antibody constant region differs from the amino acid sequence of an IgG1 constant region by a T366W substitution.

In some embodiments, the amino acid sequence of one polypeptide chain of the antibody constant region differs from the amino acid sequence of an IgG1 constant region by T350V, L351Y, F405A, and Y407V substitutions and wherein the amino acid sequence of the other polypeptide chain of the antibody constant region differs from the amino acid sequence of an IgG1 constant region by T350V, T366L, K392L, and T394W substitutions.

In some embodiments, the amino acid sequence of one polypeptide chain of the antibody constant region differs from the amino acid sequence of an IgG1 constant region by T350V, T366L, K392L, and T394W substitutions and wherein the amino acid sequence of the other polypeptide chain of the antibody constant region differs from the amino acid sequence of an IgG1 constant region by T350V, L351Y, F405A, and Y407V substitutions.

The multi-specific proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the immunoglobulin light chain can be cloned into a third expression vector; and the first, second, and third expression vectors can be stably transfected together into host cells to produce the multimeric proteins.

To achieve the highest yield of the multi-specific protein, different ratios of the first, second, and third expression vector can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the multi-specific protein. The multispecific proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

II. Characteristics of the Multi-Specific Proteins

The multi-specific proteins described herein include an NKG2D-binding site, a CD16-binding site, and a tumor-associated antigen selected from CD37, CD20, CD19, CD22, CD30, CD52, and CD133. In some embodiments, the multi-specific proteins bind to cells expressing NKG2D and/or CD16, such as NK cells, and tumor cells expressing any one of the above antigens simultaneously. Binding of the multi-specific proteins to NK cells can enhance the activity of the NK cells toward destruction of the cancer cells.

In some embodiments, the multi-specific proteins bind to a tumor-associated antigen selected from CD37, CD20, CD19, CD22, CD30, CD52, and CD133 with a similar affinity to that of a monoclonal antibody having the same respective antigen-binding site. In some embodiments, the multi-specific proteins are more effective in in killing the tumor cells expressing the antigen(s) than the corresponding respective monoclonal antibodies.

In certain embodiments, the multi-specific proteins described herein, which include an NKG2D-binding site and a binding site for a tumor-associated antigen selected from CD37, CD20, CD19, CD22, CD30, CD52, and CD133, activate primary human NK cells when co-culturing with cells expressing CD37, CD20, CD19, CD22, CD30, CD52, and CD133, respectively. NK cell activation is marked by the increase in CD107a degranulation and IFN-γ cytokine production. Furthermore, compared to a corresponding respective monoclonal antibody, the multi-specific proteins may show superior activation of human NK cells in the presence of cells expressing the antigen CD37, CD20, CD19, CD22, CD30, CD52, or CD133.

In certain embodiments, the multi-specific proteins described herein, which include an NKG2D-binding site and a binding site for a tumor-associated antigen selected from CD37, CD20, CD19, CD22, CD30, CD52, and CD133, enhance the activity of rested and IL-2-activated human NK cells co-culturing with cells expressing CD37, CD20, CD19, CD22, CD30, CD52, and CD133, respectively.

In certain embodiments, compared to a corresponding monoclonal antibody that binds to CD37, CD20, CD19, CD22, CD30, CD52, or CD133, the multi-specific proteins offer an advantage in targeting tumor cells that express medium and low levels of CD37, CD20, CD19, CD22, CD30, CD52, and CD133, respectively.

III. Therapeutic Applications

The invention provides methods for treating cancer using a multi-specific binding protein described herein and/or a pharmaceutical composition described herein. The methods may be used to treat a variety of cancers expressing of CD37, CD20, CD19, CD22, CD30, CD52, or CD133. Exemplary cancers to be treated by the CD37-targeting multi-specific binding proteins may be B-cell chronic lymphocytic leukemia (CLL), hairy-cell leukemia (HCL), non-Hodgkin lymphoma, or acute myeloid leukemia. Exemplary cancers to be treated by the CD20-targeting multi-specific binding proteins may be chronic lymphocytic leukemia, non-Hodgkin's lymphoma, follicular lymphoma, or B-cell malignancies. Exemplary cancers to be treated by the CD19-targeting multi-specific binding proteins may be chronic lymphocytic leukemia, non-Hodgkin's lymphoma, follicular lymphoma, acute lymphoblastic leukemia, B cell malignancies, multiple myeloma, or acute myeloid leukemia. Exemplary cancers to be treated by the CD22-targeting multi-specific binding proteins may be chronic lymphocytic leukemia, non-Hodgkin's lymphoma, follicular lymphoma, acute lymphoblastic leukemia, B cell malignancies, or hairy cell leukemia. Exemplary cancers to be treated by the CD30-targeting multi-specific binding proteins may be Hodgkin's lymphoma, anaplastic large cell lymphoma, cutaneous T-cell lymphoma, peripheral T cell lymphoma, adult T-cell leukemia-lymphoma, diffuse large B cell lymphoma, non-Hodgkin's lymphoma, or embryonal cell carcinoma. Exemplary cancers to be treated by the CD52-targeting multi-specific binding proteins may be chronic lymphocytic leukemia (CLL), cutaneous T-cell lymphoma, peripheral T-cell lymphoma and T-cell prolymphocytic leukemia, B cell malignancies, non-Hodgkin's lymphoma, Hodgkin's lymphoma, anaplastic large cell lymphoma, adult T-cell leukemia-lymphoma, mature T/natural killer (NK) cell neoplasms, or thymoma. Exemplary cancers to be treated by the CD133-targeting multi-specific binding proteins may be breast cancer, colon cancer, prostate cancer, liver cancer, pancreatic cancer, lung cancer, ovarian cancer, renal cancer, uterine cancer, testicular germ cell cancer, acute myeloid leukemia, acute lymphoblastic leukemia, glioma, glioblastoma, or head and neck squamous cell carcinoma.

In some other embodiments, the cancer to be treated includes brain cancer, rectal cancer, and uterine cancer. In yet other embodiments, the cancer is a squamous cell carcinoma, adenocarcinoma, small cell carcinoma, melanoma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well-differentiated carcinoma, or Wilms tumor.

In certain other embodiments, the cancer to be treated is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

IV. Combination Therapy

Another aspect of the invention provides for combination therapy. A multi-specific binding protein described herein can be used in combination with additional therapeutic agents to treat the cancer.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma (IFN-γ), colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Proteins of the invention can also be used as an adjunct to surgical removal of the primary lesion.

The amount of multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

V. Pharmaceutical Compositions

The present disclosure also features pharmaceutical compositions that contain a therapeutically effective amount of a protein described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, PA, 17th ed., 1985. For a brief review of methods for drug delivery, see, e.g., Langer (Science 249:1527-1533, 1990).

The intravenous drug delivery formulation of the present disclosure may be contained in a bag, a pen, or a syringe. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in about 12-60 vials. In certain embodiments, the formulation may be freeze-dried and 45 mg of the freeze-dried formulation may be contained in one vial. In certain embodiments, the about 40 mg-about 100 mg of freeze-dried formulation may be contained in one vial. In certain embodiments, freeze dried formulation from 12, 27, or 45 vials are combined to obtained a therapeutic dose of the protein in the intravenous drug formulation. In certain embodiments, the formulation may be a liquid formulation and stored as about 250 mg/vial to about 1000 mg/vial. In certain embodiments, the formulation may be a liquid formulation and stored as about 600 mg/vial. In certain embodiments, the formulation may be a liquid formulation and stored as about 250 mg/vial.

The protein could exist in a liquid aqueous pharmaceutical formulation including a therapeutically effective amount of the protein in a buffered solution forming a formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g., sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/ml of citric acid (e.g., 1.305 mg/ml), about 0.3 mg/ml of sodium citrate (e.g., 0.305 mg/ml), about 1.5 mg/ml of disodium phosphate dihydrate (e.g., 1.53 mg/ml), about 0.9 mg/ml of sodium dihydrogen phosphate dihydrate (e.g., 0.86), and about 6.2 mg/ml of sodium chloride (e.g., 6.165 mg/ml). In certain embodiments, the buffer system includes 1-1.5 mg/ml of citric acid, 0.25 to 0.5 mg/ml of sodium citrate, 1.25 to 1.75 mg/ml of disodium phosphate dihydrate, 0.7 to 1.1 mg/ml of sodium dihydrogen phosphate dihydrate, and 6.0 to 6.4 mg/ml of sodium chloride. In certain embodiments, the pH of the formulation is adjusted with sodium hydroxide.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/ml. In certain embodiments, the concentration of mannitol may be about 7.5 to 15 mg/ml. In certain embodiments, the concentration of mannitol may be about 10-14 mg/ml. In certain embodiments, the concentration of mannitol may be about 12 mg/ml. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with 61.2 mL of the protein product solution in order to allow an extractable volume of 60 mL. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 dalton mass decrease of the parent peptide. The subsequent hydrolysis results in an 18 dalton mass increase. Isolation of the succinimide intermediate is difficult due to instability under aqueous conditions. As such, deamidation is typically detectable as 1 dalton mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation of the present disclosure may be preserved under conditions of pH and humidity to prevent deamination of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

The protein of the present disclosure could exist in a lyophilized formulation including the proteins and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between 6 to 8. In certain embodiments, the pH range for the lyophilized drug product may be from 7 to 8.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g., phosphate-buffered saline), sterile saline solution, Ringer's solution or dextrose solution.

In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308: 33-41, 2001).

In general, dosages based on body weight are from about 0.01 μg to about 100 mg per kg of body weight, such as about 0.01 μg to about 100 mg/kg of body weight, about 0.01 μg to about 50 mg/kg of body weight, about 0.01 μg to about 10 mg/kg of body weight, about 0.01 μg to about 1 mg/kg of body weight, about 0.01 μg to about 100 μg/kg of body weight, about 0.01 μg to about 50 μg/kg of body weight, about 0.01 μg to about 10 μg/kg of body weight, about 0.01 μg to about 1 μg/kg of body weight, about 0.01 μg to about 0.1 μg/kg of body weight, about 0.1 μg to about 100 mg/kg of body weight, about 0.1 μg to about 50 mg/kg of body weight, about 0.1 μg to about 10 mg/kg of body weight, about 0.1 μg to about 1 mg/kg of body weight, about 0.1 μg to about 100 μg/kg of body weight, about 0.1 μg to about 10 μg/kg of body weight, about 0.1 μg to about 1 μg/kg of body weight, about 1 μg to about 100 mg/kg of body weight, about 1 μg to about 50 mg/kg of body weight, about 1 μg to about 10 mg/kg of body weight, about 1 μg to about 1 mg/kg of body weight, about 1 μg to about 100 μg/kg of body weight, about 1 μg to about 50 μg/kg of body weight, about 1 μg to about 10 μg/kg of body weight, about 10 μg to about 100 mg/kg of body weight, about 10 μg to about 50 mg/kg of body weight, about 10 μg to about 10 mg/kg of body weight, about 10 μg to about 1 mg/kg of body weight, about 10 μg to about 100 μg/kg of body weight, about 10 μg to about 50 μg/kg of body weight, about 50 μg to about 100 mg/kg of body weight, about 50 μg to about 50 mg/kg of body weight, about 50 μg to about 10 mg/kg of body weight, about 50 μg to about 1 mg/kg of body weight, about 50 μg to about 100 μg/kg of body weight, about 100 μg to about 100 mg/kg of body weight, about 100 μg to about 50 mg/kg of body weight, about 100 μg to about 10 mg/kg of body weight, about 100 μg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1—NKG2D Binding Domains Bind to NKG2D

NKG2D Binding Domains Bind to Purified Recombinant NKG2D

The nucleic acid sequences of human, mouse or cynomolgus NKG2D ectodomains were fused with nucleic acid sequences encoding human IgG1 Fc domains and introduced into mammalian cells to be expressed. After purification, NKG2D-Fc fusion proteins were adsorbed to wells of microplates. After blocking the wells with bovine serum albumin to prevent non-specific binding, NKG2D-binding domains were titrated and added to the wells pre-adsorbed with NKG2D-Fc fusion proteins. Primary antibody binding was detected using a secondary antibody which was conjugated to horseradish peroxidase and specifically recognizes a human kappa light chain to avoid Fc cross-reactivity. 3,3',5,5'-Tetramethylbenzidine (TMB), a substrate for horseradish peroxidase, was added to the wells to visualize the binding signal, whose absorbance was measured at 450 nM and corrected at 540 nM. An NKG2D-binding domain clone, an isotype control or a positive control (comprising heavy chain and light chain variable domains selected from SEQ ID NOs:101-104, or anti-mouse NKG2D clones MI-6 and CX-5 available at eBioscience) was added to each well.

Figure 3:
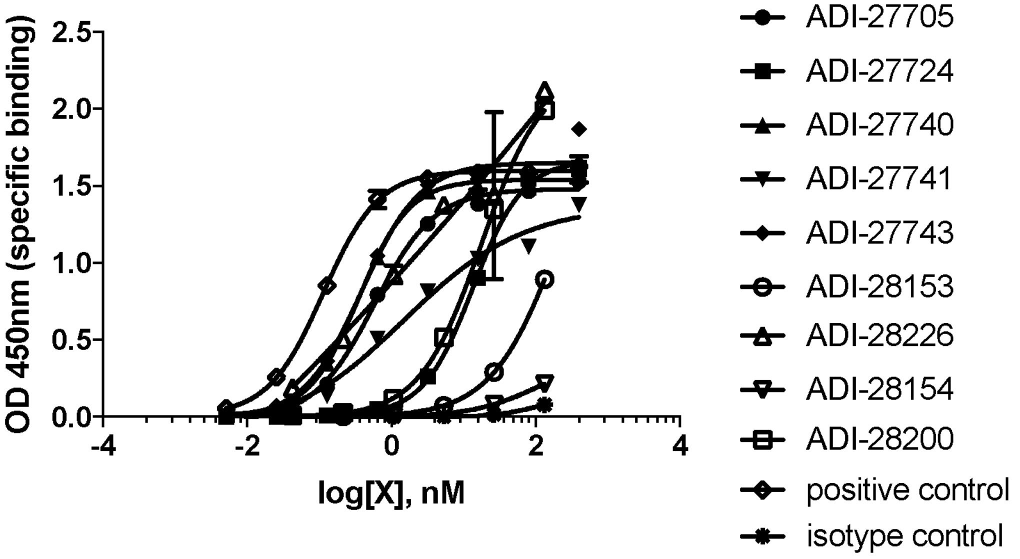
FIG. 3 are line graphs demonstrating the binding affinity of NKG2D-binding domains (listed as clones) to human recombinant NKG2D in an ELISA assay.
Figure 4:
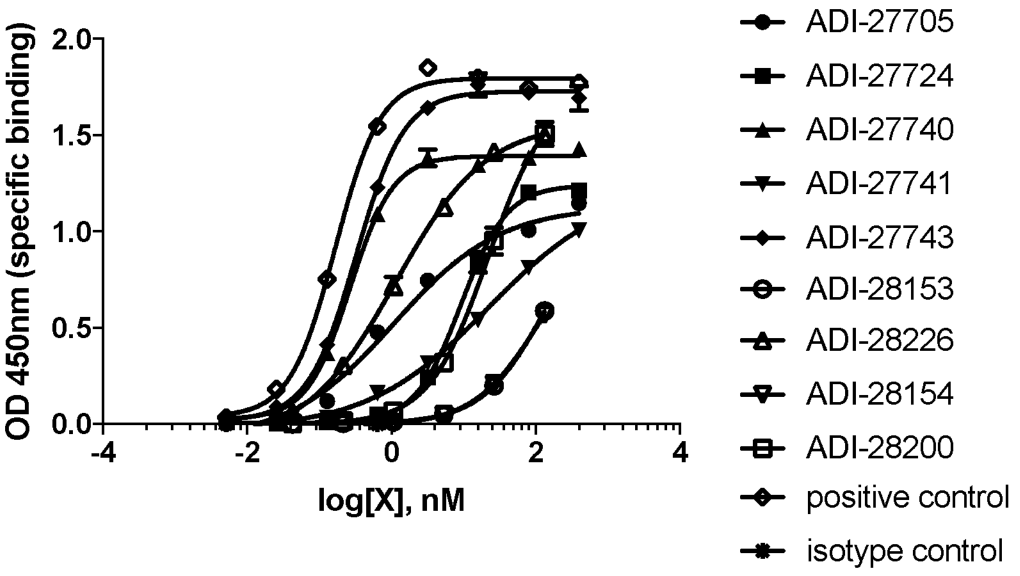
FIG. 4 are line graphs demonstrating the binding affinity of NKG2D-binding domains (listed as clones) to cynomolgus recombinant NKG2D in an ELISA assay.
Figure 5:
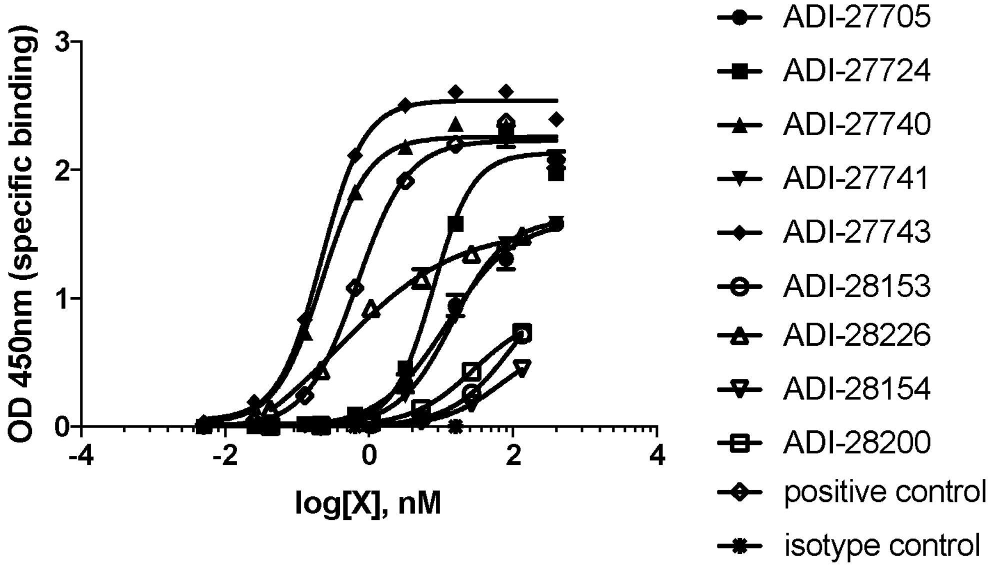
FIG. 5 are line graphs demonstrating the binding affinity of NKG2D-binding domains (listed as clones) to mouse recombinant NKG2D in an ELISA assay.

The isotype control showed minimal binding to recombinant NKG2D-Fc proteins, while the positive control bound strongest to the recombinant antigens. NKG2D-binding domains produced by all clones demonstrated binding across human, mouse, and cynomolgus recombinant NKG2D-Fc proteins, although with varying affinities from clone to clone. Generally, each anti-NKG2D clone bound to human (FIG. 3) and cynomolgus (FIG. 4) recombinant NKG2D-Fc with similar affinity, but with lower affinity to mouse (FIG. 5) recombinant NKG2D-Fc.

NKG2D-Binding Domains Bind to Cells Expressing NKG2D

EL4 mouse lymphoma cell lines were engineered to express human or mouse NKG2D-CD3 zeta signaling domain chimeric antigen receptors. An NKG2D-binding clone, an isotype control or a positive control was used at a 100 nM concentration to stain extracellular NKG2D expressed on the EL4 cells. The antibody binding was detected using fluorophore-conjugated anti-human IgG secondary antibodies. Cells were analyzed by flow cytometry, and fold-over-background (FOB) was calculated using the mean fluorescence intensity (MFI) of NKG2D expressing cells compared to parental EL4 cells.

Figure 6:
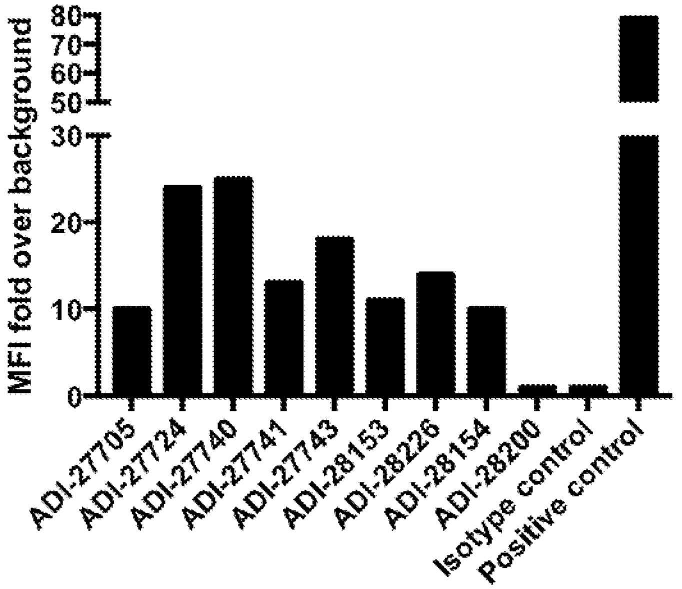
FIG. 6 are bar graphs demonstrating the binding of NKG2D-binding domains (listed as clones) to EL4 cells expressing human NKG2D by flow cytometry showing mean fluorescence intensity (MFI) fold over background (FOB).
Figure 7:
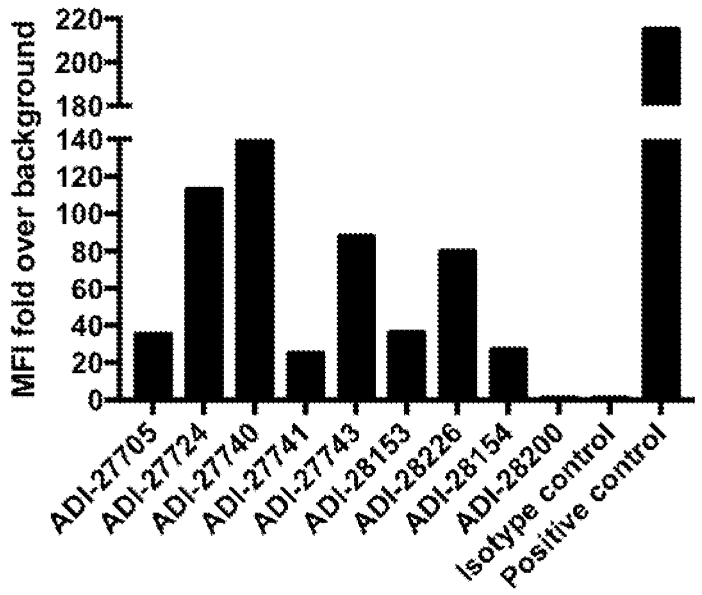
FIG. 7 are bar graphs demonstrating the binding of NKG2D-binding domains (listed as clones) to EL4 cells expressing mouse NKG2D by flow cytometry showing mean fluorescence intensity (MFI) fold over background (FOB).

NKG2D-binding domains produced by all clones bound to EL4 cells expressing human and mouse NKG2D. Positive control antibodies (comprising heavy chain and light chain variable domains selected from SEQ ID NOs:101-104, or anti-mouse NKG2D clones MI-6 and CX-5 available at eBioscience) gave the best FOB binding signal. The NKG2D-binding affinity for each clone was similar between cells expressing human NKG2D (FIG. 6) and mouse (FIG. 7) NKG2D.

Example 2—NKG2D-Binding Domains Block Natural Ligand Binding to NKG2D

Competition With ULBP-6

Figure 8:
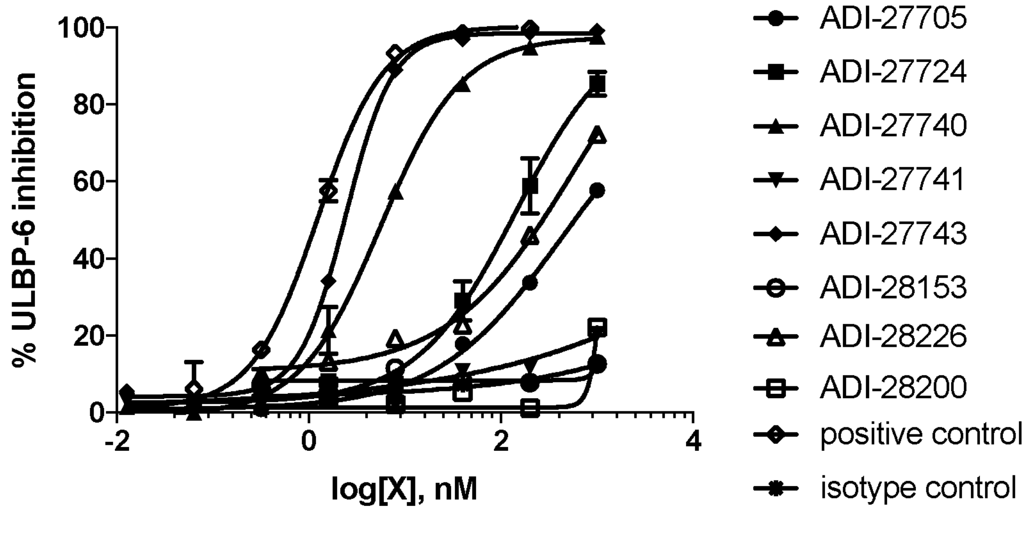
FIG. 8 are line graphs demonstrating specific binding affinity of NKG2D-binding domains (listed as clones) to recombinant human NKG2D-Fc by competing with natural ligand ULBP-6.

Recombinant human NKG2D-Fc proteins were adsorbed to wells of a microplate, and the wells were blocked with bovine serum albumin reduce non-specific binding. A saturating concentration of ULBP-6-His-biotin was added to the wells, followed by addition of the NKG2D-binding domain clones. After a 2-hour incubation, wells were washed and ULBP-6-His-biotin that remained bound to the NKG2D-Fc coated wells was detected by streptavidin-conjugated to horseradish peroxidase and TMB substrate. Absorbance was measured at 450 nM and corrected at 540 nM. After subtracting background, specific binding of NKG2D-binding domains to the NKG2D-Fc proteins was calculated from the percentage of ULBP-6-His-biotin that was blocked from binding to the NKG2D-Fc proteins in wells. The positive control antibody (comprising heavy chain and light chain variable domains selected from SEQ ID NOs:101-104) and various NKG2D-binding domains blocked ULBP-6 binding to NKG2D, while isotype control showed little competition with ULBP-6 (FIG. 8).

ULBP-6 sequence is represented by SEQ ID NO:108

```
                                    (SEQ ID NO: 108)
MAAAAIPALLLCLPLLFLLFGWSRARRDDPHSLCYDITVIPKFRPGPRW

CAVQGQVDEKTFLHYDCGNKTVTPVSPLGKKLNVTMAWKAQNPVLREVV

DILTEQLLDIQLENYTPKEPLTLQARMSCEQKAEGHSSGSWQFSIDGQT

FLLFDSEKRMWTTVHPGARKMKEKWENDKDVAMSFHYISMGDCIGWLED

FLMGMDSTLEPSAGAPLAMSSGTTQLRATATTLILCCLLIILPCFILPG

I
```

Competition with MICA

Figure 9:
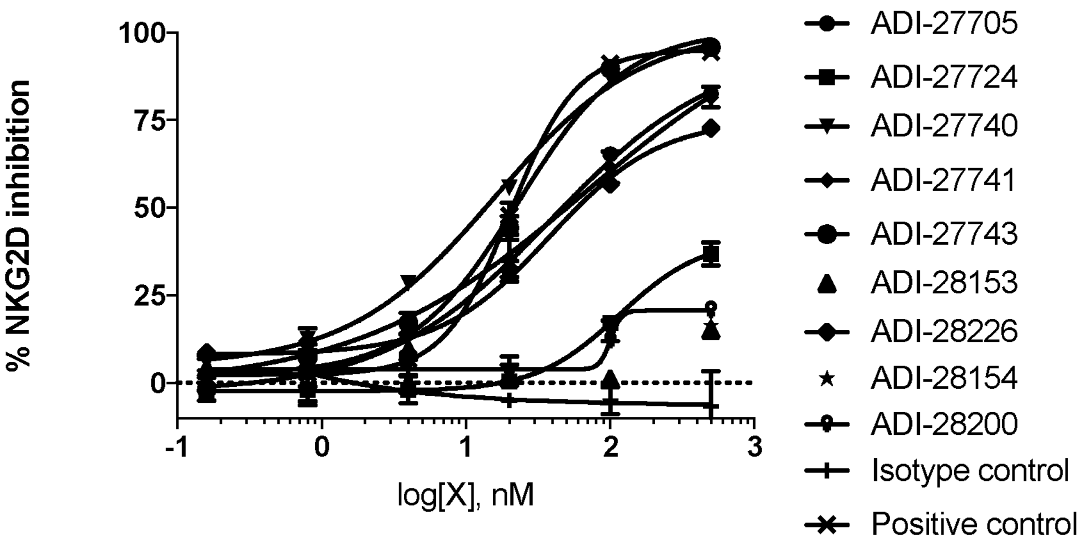
FIG. 9 are line graphs demonstrating specific binding affinity of NKG2D-binding domains (listed as clones) to recombinant human NKG2D-Fc by competing with natural ligand MICA.

Recombinant human MICA-Fc proteins were adsorbed to wells of a microplate, and the wells were blocked with bovine serum albumin to reduce non-specific binding. NKG2D-Fc-biotin was added to wells followed by NKG2D-binding domains. After incubation and washing, NKG2D-Fc-biotin that remained bound to MICA-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the MICA-Fc coated wells. The positive control antibody (comprising heavy chain and light chain variable domains selected from SEQ ID NOs:101-104) and various NKG2D-binding domains blocked MICA binding to NKG2D, while isotype control showed little competition with MICA (FIG. 9).

Competition with Rae-1 Delta

Figure 10:
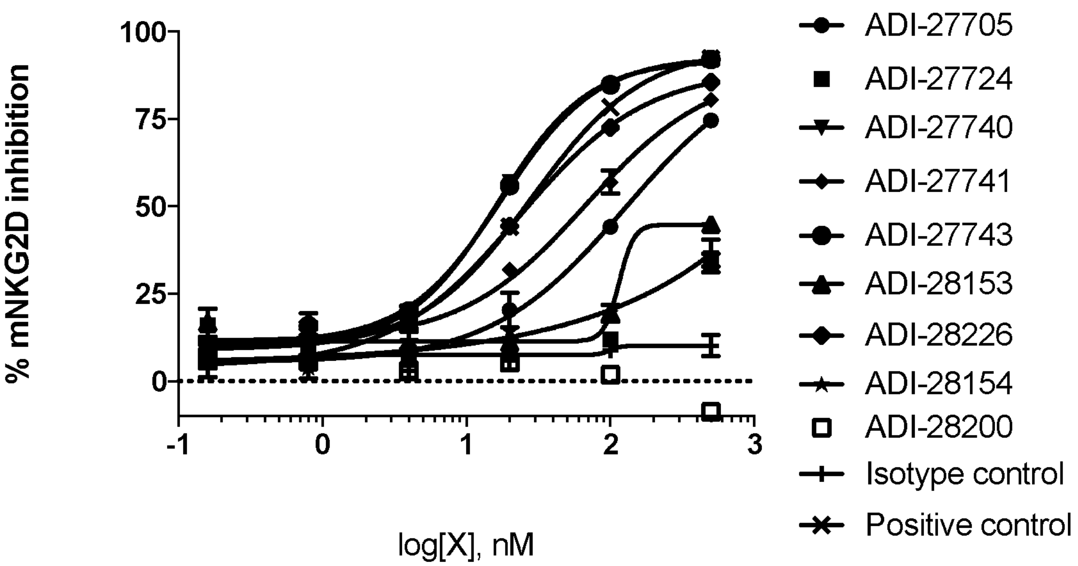
FIG. 10 are line graphs demonstrating specific binding affinity of NKG2D-binding domains (listed as clones) to recombinant mouse NKG2D-Fc by competing with natural ligand Rae-1 delta.

Recombinant mouse Rae-ldelta-Fc (purchased from R&D Systems) was adsorbed to wells of a microplate, and the wells were blocked with bovine serum albumin to reduce non-specific binding. Mouse NKG2D-Fc-biotin was added to the wells followed by NKG2D-binding domains. After incubation and washing, NKG2D-Fc-biotin that remained bound to Rae-ldelta-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the Rae-ldelta-Fc coated wells. The positive control (comprising heavy chain and light chain variable domains selected from SEQ ID NOs:101-104, or anti-mouse NKG2D clones MI-6 and CX-5 available at eBioscience) and various NKG2D-binding domain clones blocked Rae-ldelta binding to mouse NKG2D, while the isotype control antibody showed little competition with Rae-ldelta (FIG. 10).

Example 3—NKG2D-Binding Domain Clones Activate NKG2D

Nucleic acid sequences of human and mouse NKG2D were fused to nucleic acid sequences encoding a CD3 zeta signaling domain to obtain chimeric antigen receptor (CAR) constructs. The NKG2D-CAR constructs were then cloned into a retrovirus vector using Gibson assembly and transfected into expi293 cells for retrovirus production. EL4 cells were infected with viruses containing NKG2D-CAR together with 8 μg/mL polybrene. 24 hours after infection, the expression levels of NKG2D-CAR in the EL4 cells were analyzed by flow cytometry, and clones which express high levels of the NKG2D-CAR on the cell surface were selected.

Figure 11:
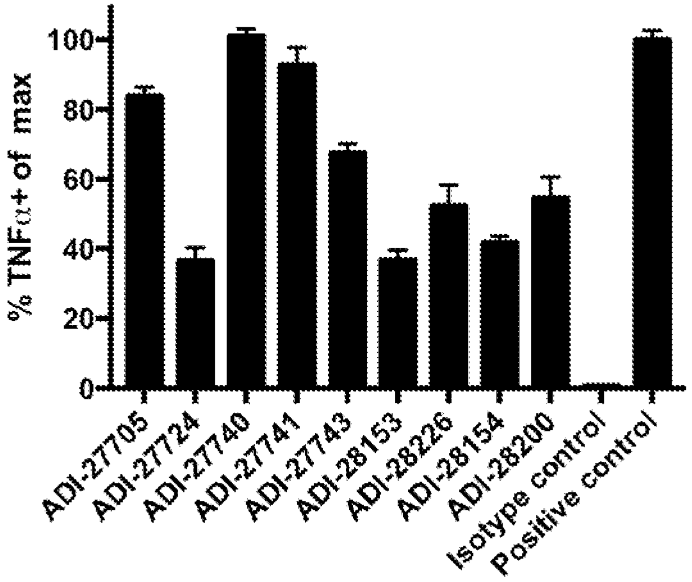
FIG. 11 are bar graphs showing activation of human NKG2D by NKG2D-binding domains (listed as clones) by quantifying the percentage of TNF-α positive cells, which express human NKG2D-CD3 zeta fusion proteins.
Figure 12:
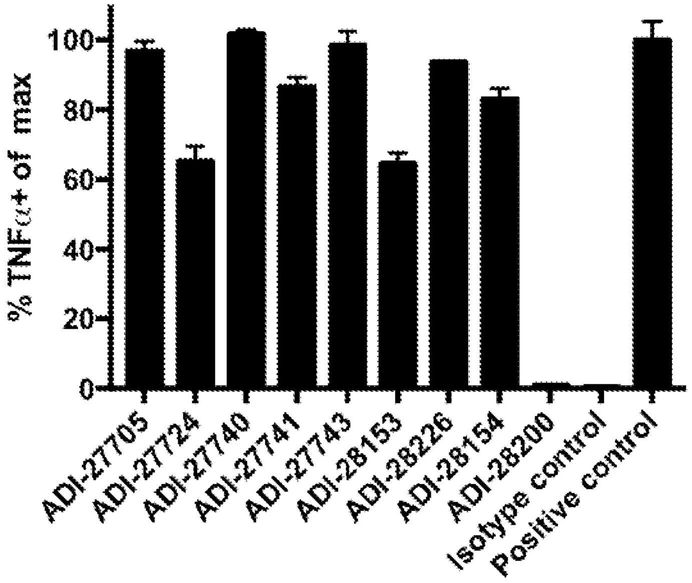
FIG. 12 are bar graphs showing activation of mouse NKG2D by NKG2D-binding domains (listed as clones) by quantifying the percentage of TNF-α positive cells, which express mouse NKG2D-CD3 zeta fusion proteins.

To determine whether NKG2D-binding domains activate NKG2D, they were adsorbed to wells of a microplate, and NKG2D-CAR EL4 cells were cultured on the antibody fragment-coated wells for 4 hours in the presence of brefeldin-A and monensin. Intracellular TNF-α production, an indicator for NKG2D activation, was assayed by flow cytometry. The percentage of TNF-α positive cells was normalized to the cells treated with the positive control. All NKG2D-binding domains activated both human NKG2D (FIG. 11) and mouse NKG2D (FIG. 12).

Example 4—NKG2D-Binding Domains Activate NK Cells

Primary Human NK Cells

Figure 13:
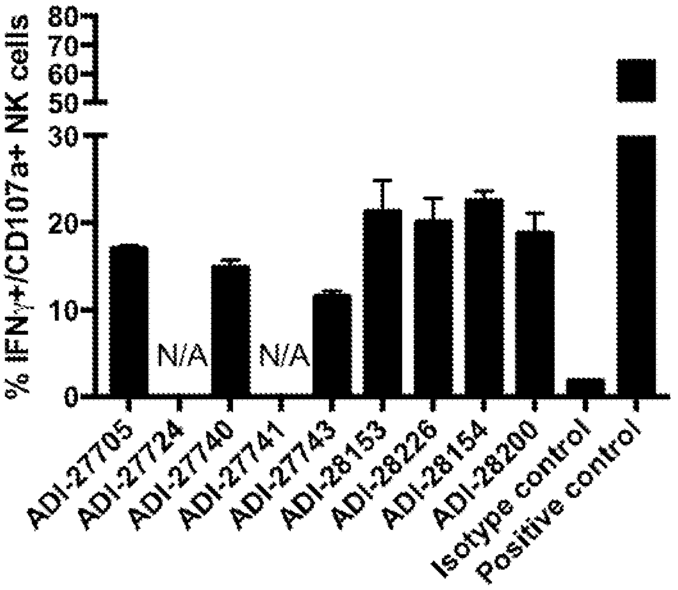
FIG. 13 are bar graphs showing activation of human NK cells by NKG2D-binding domains (listed as clones).
Figure 14:
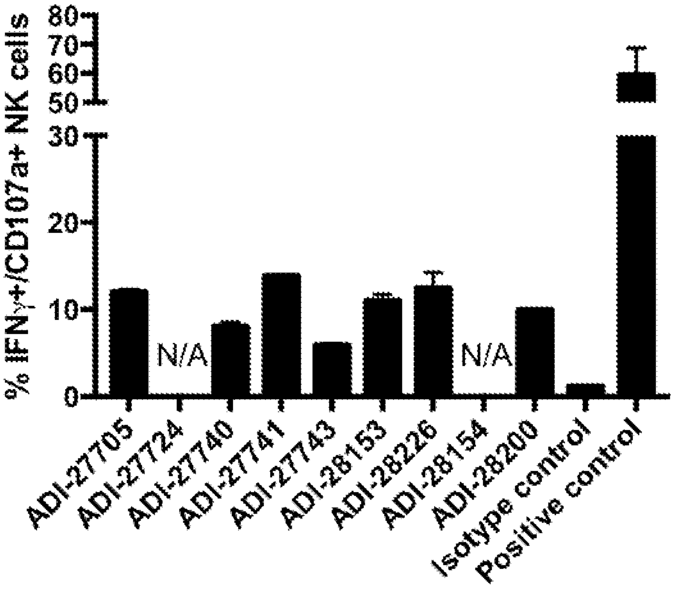
FIG. 14 are bar graphs showing activation of human NK cells by NKG2D-binding domains (listed as clones).

Peripheral blood mononuclear cells (PBMCs) were isolated from human peripheral blood buffy coats using density gradient centrifugation. NK cells ($CD3^{-}CD56^{+}$) were isolated using negative selection with magnetic beads from PBMCs, and the purity of the isolated NK cells was typically >95%. Isolated NK cells were then cultured in media containing 100 ng/mL IL-2 for 24-48 hours before they were transferred to the wells of a microplate to which the NKG2D-binding domains were adsorbed, and cultured in the media containing fluorophore-conjugated anti-CD107a antibody, brefeldin-A, and monensin. Following culture, NK cells were assayed by flow cytometry using fluorophore-conjugated antibodies against CD3, CD56 and IFN-γ. CD107a and IFN-γ staining were analyzed in $CD3^{-}CD56^{+}$ cells to assess NK cell activation. The increase in CD107a/IFN-γ double-positive cells is indicative of better NK cell activation through engagement of two activating receptors rather than one receptor. NKG2D-binding domains and the positive control (e.g., heavy chain variable domain represent by SEQ ID NO:101 or SEQ ID NO:103, and light chain variable domain represented by SEQ ID NO:102 or SEQ ID NO:104) showed a higher percentage of NK cells becoming $CD107a^{+}$ and IFN-$\gamma^{+}$ than the isotype control (FIG. 13 & FIG. 14 represent data from two independent experiments, each using a different donor's PBMC for NK cell preparation).

Primary Mouse NK Cells

Figure 15:
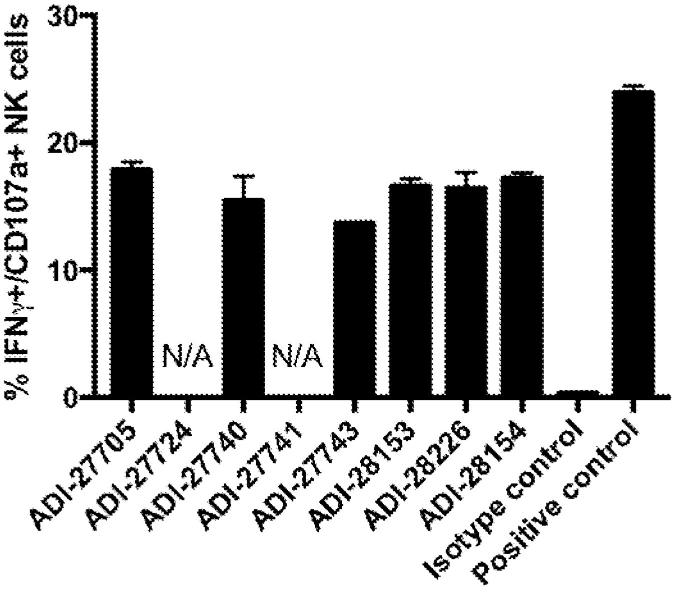
FIG. 15 are bar graphs showing activation of mouse NK cells by NKG2D-binding domains (listed as clones).
Figure 16:
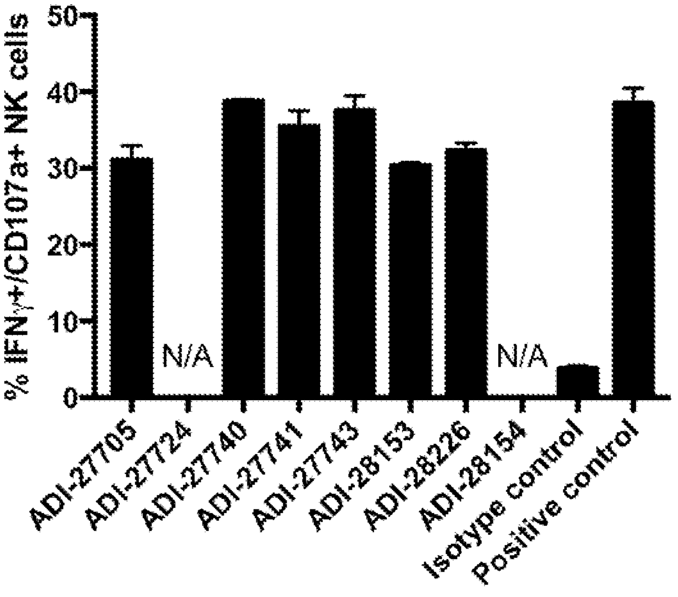
FIG. 16 are bar graphs showing activation of mouse NK cells by NKG2D-binding domains (listed as clones).

Spleens were obtained from C57Bl/6 mice and crushed through a 70 μm cell strainer to obtain single cell suspension. Cells were pelleted and resuspended in ACK lysis buffer (purchased from Thermo Fisher Scientific # A1049201; 155 mM ammonium chloride, 10 mM potassium bicarbonate, 0.01 mM EDTA) to remove red blood cells. The remaining cells were cultured with 100 ng/mL hIL-2 for 72 hours before being harvested and prepared for NK cell isolation. NK cells ($CD3^{-}NK1.1^{+}$) were then isolated from spleen cells using a negative depletion technique with magnetic beads with typically >90% purity. Purified NK cells were cultured in media containing 100 ng/mL mIL-15 for 48 hours before they were transferred to the wells of a microplate to which the NKG2D-binding domains were adsorbed, and cultured in the media containing fluorophore-conjugated anti-CD107a antibody, brefeldin-A, and monensin. Following culture in NKG2D-binding domain-coated wells, NK cells were assayed by flow cytometry using fluorophore-conjugated antibodies against CD3, NK1.1 and IFN-γ. CD107a and IFN-γ staining were analyzed in $CD3^{-}NK1.1^{+}$ cells to assess NK cell activation. The increase in CD107a/IFN-γ double-positive cells is indicative of better NK cell activation through engagement of two activating receptors rather than one receptor. NKG2D-binding domains and the positive control (selected from anti-mouse NKG2D clones MI-6 and CX-5 available at eBioscience) showed a higher percentage of NK cells becoming $CD107a^{+}$ and IFN-$\gamma^{+}$ than the isotype control (FIG. 15 & FIG. 16 represent data from two independent experiments, each using a different mouse for NK cell preparation).

Example 5—NKG2D-Binding Domains Enable Cytotoxicity of Target Tumor Cells

Human and mouse primary NK cell activation assays demonstrate increased cytotoxicity markers on NK cells after incubation with NKG2D-binding domains. To address whether this translates into increased tumor cell lysis, a cell-based assay was utilized where each NKG2D-binding domain was developed into a monospecific antibody. The Fc region was used as one targeting arm, while the Fab region (NKG2D-binding domain) acted as another targeting arm to activate NK cells. THP-1 cells, which are of human origin and express high levels of Fc receptors, were used as a tumor target and a Perkin Elmer DELFIA Cytotoxicity Kit was used. THP-1 cells were labeled with BATDA reagent, and resuspended at $10^{5}$/mL in culture media. Labeled THP-1 cells were then combined with NKG2D antibodies and isolated mouse NK cells in wells of a microtiter plate at 37° C. for 3 hours. After incubation, 20 μl of the culture supernatant was removed, mixed with 200 μl of Europium solution and incubated with shaking for 15 minutes in the dark. Fluorescence was measured over time by a PheraStar plate reader equipped with a time-resolved fluorescence module (Excitation 337 nm, Emission 620 nm) and specific lysis was calculated according to the kit instructions.

Figure 17:
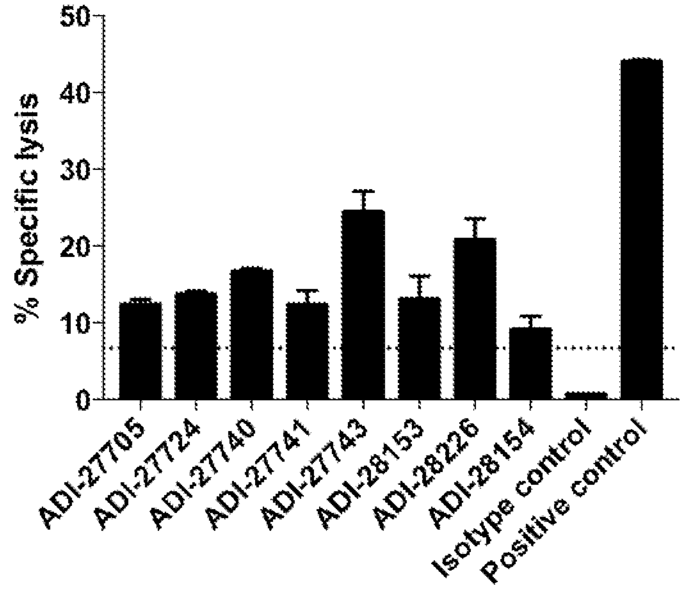
FIG. 17 are bar graphs showing the cytotoxic effect of NKG2D-binding domains (listed as clones) on tumor cells.

The positive control, ULBP-6—a natural ligand for NKG2D, showed increased specific lysis of THP-1 target cells by mouse NK cells. NKG2D antibodies also increased specific lysis of THP-1 target cells, while isotype control antibody showed reduced specific lysis. The dotted line indicates specific lysis of THP-1 cells by mouse NK cells without antibody added (FIG. 17).

Example 6—NKG2D Antibodies Show High Thermostability

Figure 18:
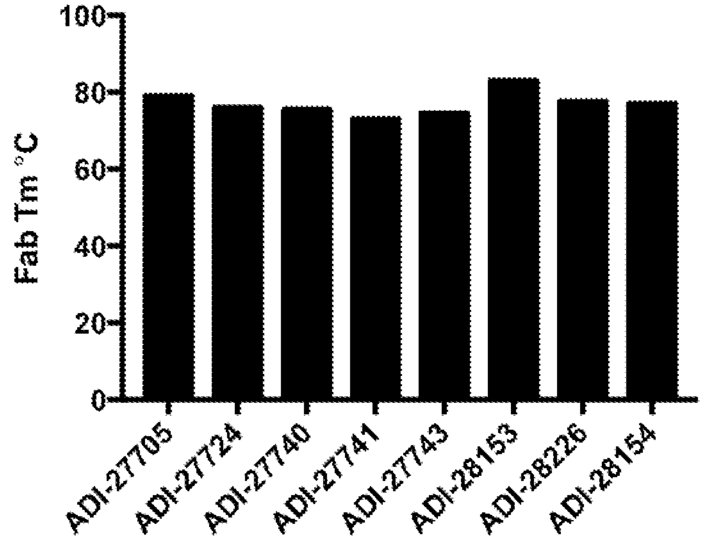
FIG. 18 are bar graphs showing the melting temperature of NKG2D-binding domains (listed as clones) measured by differential scanning fluorimetry.

Melting temperatures of NKG2D-binding domains were assayed using differential scanning fluorimetry. The extrapolated apparent melting temperatures are high relative to typical IgG1 antibodies (FIG. 18).

Example 7—Synergistic Activation of Human NK Cells by Cross-Linking NKG2D and CD16

Primary Human NK Cell Activation Assay

Peripheral blood mononuclear cells (PBMCs) were isolated from peripheral human blood buffy coats using density gradient centrifugation. NK cells were purified from PBMCs using negative magnetic beads (StemCell #17955). NK cells were >90% $CD3^{-}CD56^{+}$ as determined by flow cytometry. Cells were then expanded 48 hours in media containing 100 ng/mL hIL-2 (Peprotech #200-02) before use in activation assays. Antibodies were coated onto a 96-well flat-bottom plate at a concentration of 2 μg/ml (anti-CD16, Biolegend #302013) and 5 μg/mL (anti-NKG2D, R&D # MAB139) in 100 μl sterile PBS overnight at 4° C. followed by washing the wells thoroughly to remove excess antibody. For the assessment of degranulation IL-2-activated NK cells were resuspended at $5\times10^{5}$ cells/ml in culture media supplemented with 100 ng/mL human IL-2 (hIL2) and 1 μg/mL APC-conjugated anti-CD107a mAb (Biolegend #328619). $1\times10^{5}$ cells/well were then added onto antibody coated plates. The protein transport inhibitors Brefeldin A (BFA, Biolegend #420601) and Monensin (Biolegend #420701) were added at a final dilution of 1:1000 and 1:270, respectively. Plated cells were incubated for 4 hours at 37° C. in 5% $CO_2$. For intracellular staining of IFN-γ NK cells were labeled with anti-CD3 (Biolegend #300452) and anti-CD56 mAb (Biolegend #318328) and subsequently fixed and permeabilized and labeled with anti-IFN-γ mAb (Biolegend #506507). NK cells were analyzed for expression of CD107a and IFN-γ by flow cytometry after gating on live $CD56^{+}CD3^{-}$ cells.

Figure 19A:
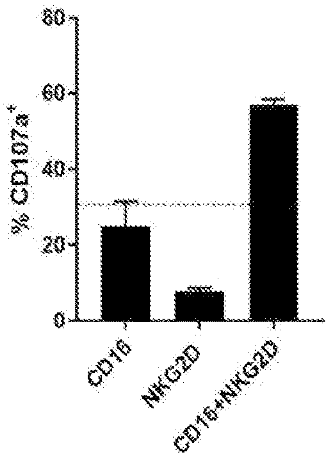
FIGS. 19A-19C are bar graphs of synergistic activation of NK cells using CD16 and NKG2D binding.
Figure 19B:
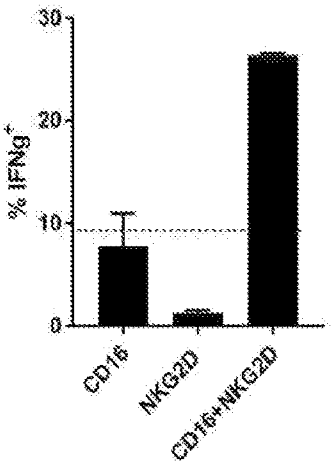
Figure 19C:
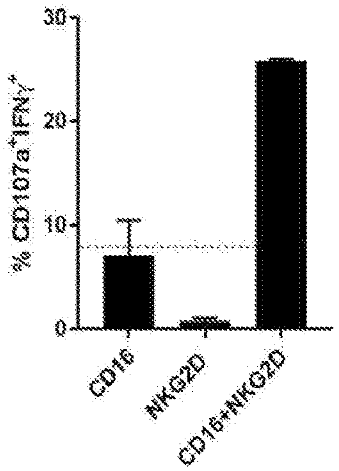
Figure 20:
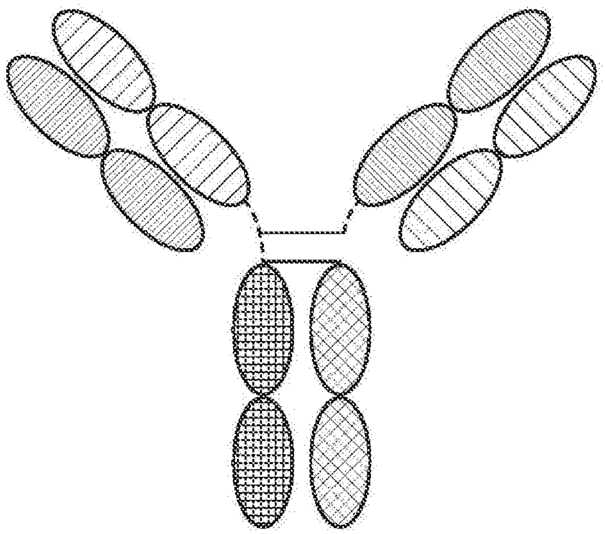
FIG. 20 is a representation of a TriNKET in the Triomab form, which is a trifunctional, bispecific antibody that maintains an IgG-like shape. This chimera consists of two half antibodies, each with one light and one heavy chain, that originate from two parental antibodies. Triomab form may be a heterodimeric construct containing ½ of rat antibody and ½ of mouse antibody.
Figure 21:
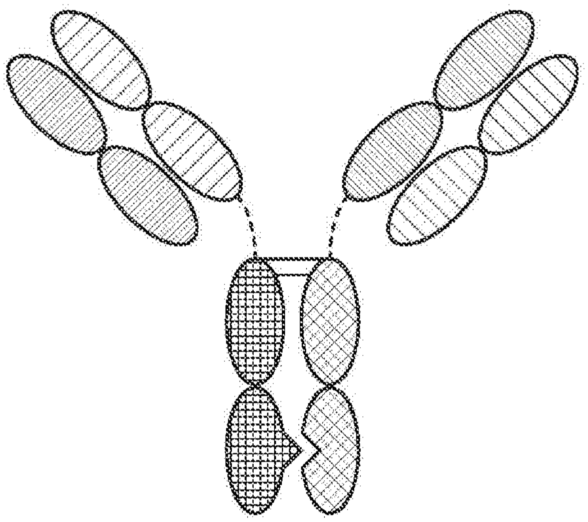
FIG. 21 is a representation of a TriNKET in the KiH Common Light Chain (LC) form, which involves the knobs-into-holes (KIHs) technology. KiH is a heterodimer containing 2 Fabs binding to target 1 and 2, and an Fc stabilized by heterodimerization mutations. TriNKET in the KiH format may be a heterodimeric construct with 2 Fabs binding to target 1 and target 2, containing two different heavy chains and a common light chain that pairs with both heavy chains.
Figure 22:
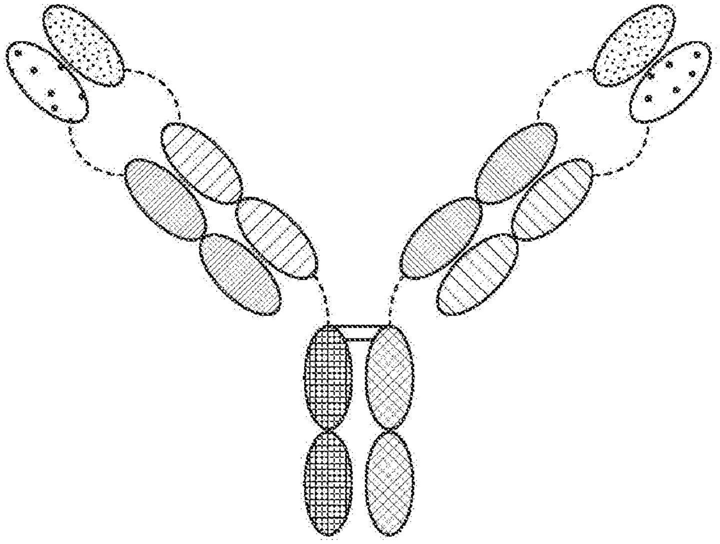
FIG. 22 is a representation of a TriNKET in the dual-variable domain immunoglobulin (DVD-Ig™) form, which combines the target-binding domains of two monoclonal antibodies via flexible naturally occurring linkers, and yields a tetravalent IgG-like molecule. DVD-Ig™ is a homodimeric construct where variable domain targeting antigen 2 is fused to the N-terminus of a variable domain of Fab targeting antigen 1 Construct contains normal Fc.
Figure 23:
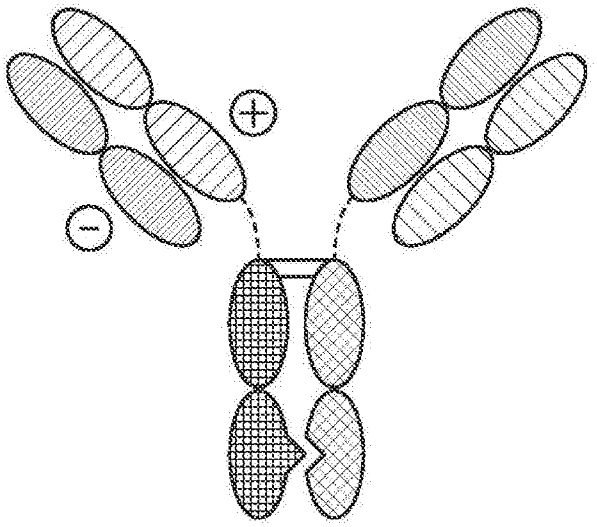
FIG. 23 is a representation of a TriNKET in the Orthogonal Fab interface (Ortho-Fab) form, which is a heterodimeric construct that contains 2 Fabs binding to target 1 and target 2 fused to Fc. LC-HC pairing is ensured by orthogonal interface. Heterodimerization is ensured by mutations in the Fc.
Figure 24:
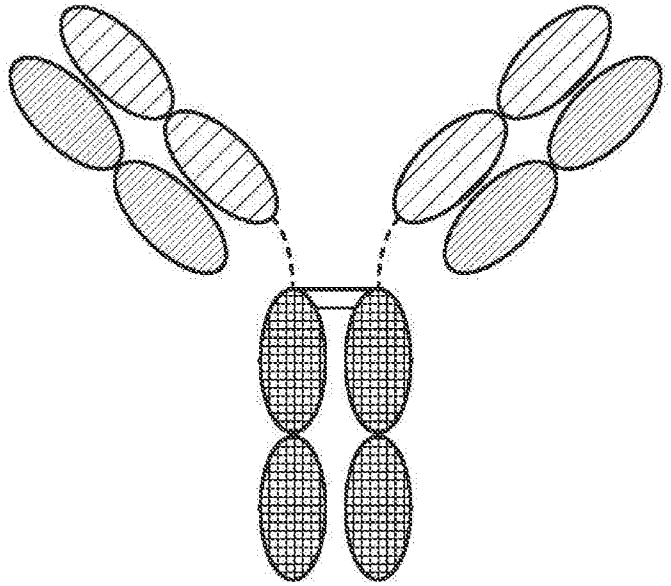
FIG. 24 is a representation of a TriNKET in the 2-in-1 Ig format.
Figure 25:
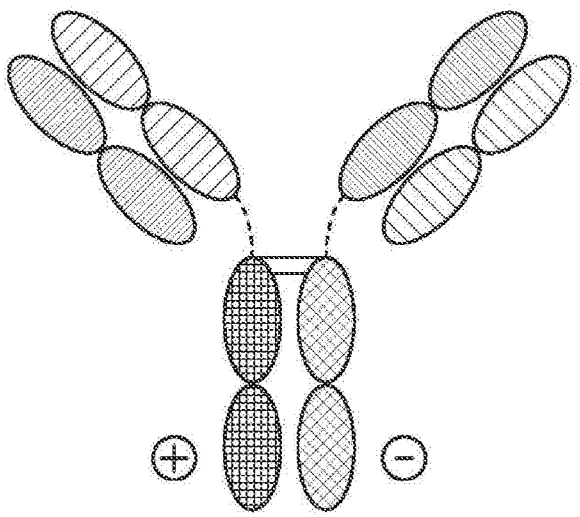
FIG. 25 is a representation of a TriNKET in the ES form, which is a heterodimeric construct containing two different Fabs binding to target 1 and target 2 fused to the Fc. Heterodimerization is ensured by electrostatic steering mutations in the Fc.
Figure 26:
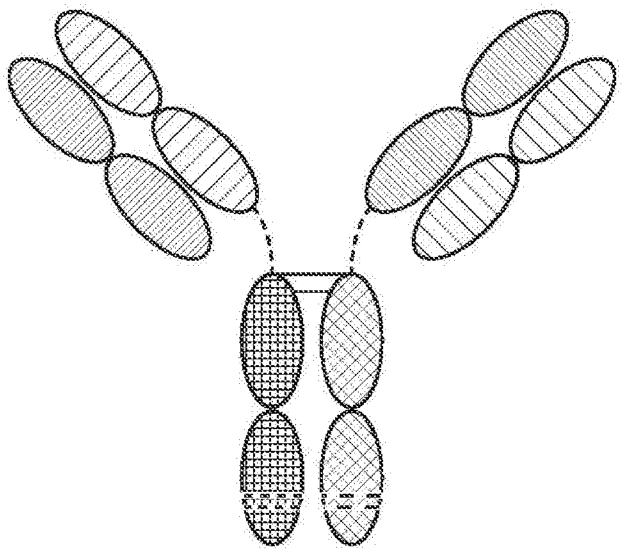
FIG. 26 is a representation of a TriNKET in the Fab Arm Exchange form: antibodies that exchange Fab arms by swapping a heavy chain and attached light chain (half-molecule) with a heavy-light chain pair from another molecule, resulting in bispecific antibodies. Fab Arm Exchange form (cFae) is a heterodimer containing 2 Fabs binding to target 1 and 2, and an Fc stabilized by heterodimerization mutations.
Figure 27:
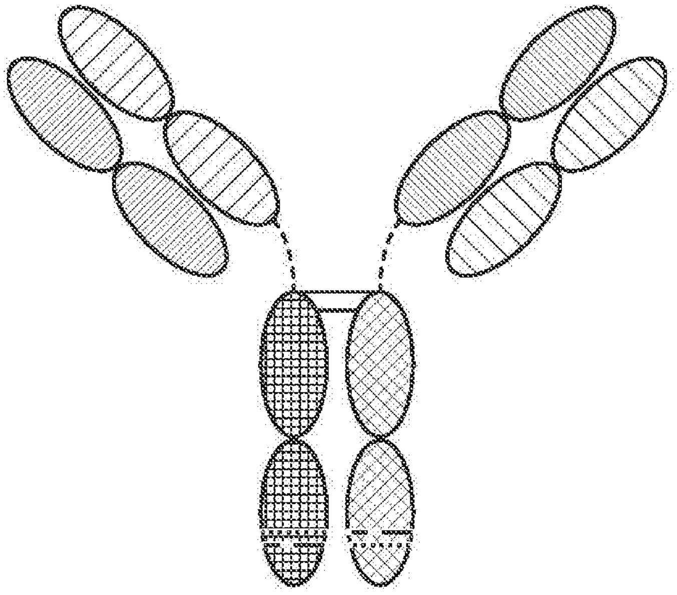
FIG. 27 is a representation of a TriNKET in the SEED Body form, which is a heterodimer containing 2 Fabs binding to target 1 and 2, and an Fc stabilized by heterodimerization mutations.
Figure 28:
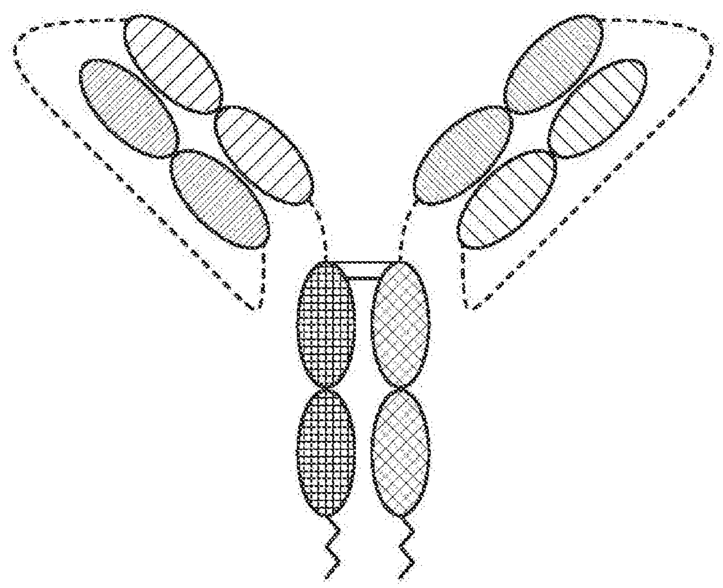
FIG. 28 is a representation of a TriNKET in the LuZ-Y form, in which a leucine zipper is used to induce heterodimerization of two different HCs. The LuZ-Y form is a heterodimer containing two different scFabs binding to target 1 and 2, fused to Fc. Heterodimerization is ensured through leucine zipper motifs fused to C-terminus of Fc.
Figure 29:
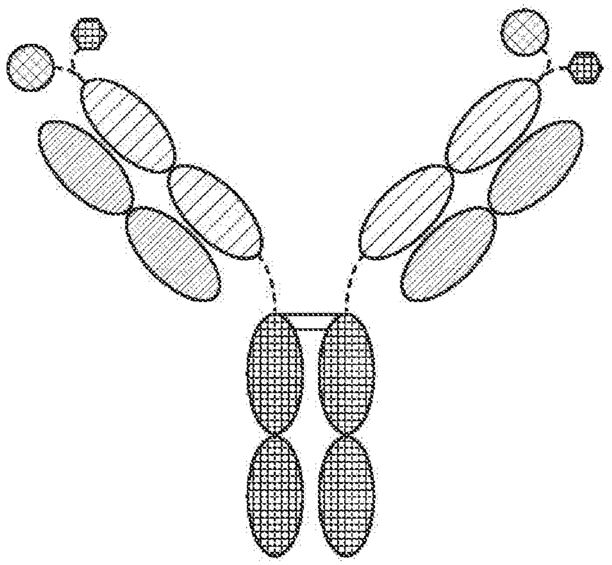
FIG. 29 is a representation of a TriNKET in the Cov-X-Body form.

To investigate the relative potency of receptor combination, crosslinking of NKG2D or CD16 and co-crosslinking of both receptors by plate-bound stimulation was performed. As shown in FIG. 19 (FIGS. 19A-19C), combined stimulation of CD16 and NKG2D resulted in highly elevated levels of CD107a (degranulation) (FIG. 19A) and/or IFN-γ production (FIG. 19B). Dotted lines represent an additive effect of individual stimulations of each receptor.

CD107a levels and intracellular IFN-γ production of IL-2-activated NK cells were analyzed after 4 hours of plate-bound stimulation with anti-CD16, anti-NKG2D or a combination of both monoclonal antibodies. Graphs indicate the mean (n=2)±SD. FIG. 19A demonstrates levels of CD107a; FIG. 19B demonstrates levels of IFN-γ; FIG. 19C demonstrates levels of CD107a and IFN-γ. Data shown in FIGS. 19A-19C are representative of five independent experiments using five different healthy donors.

Example 8—Assessment of TriNKETs Binding to Cell-Expressed Human NKG2D

Figure 35:
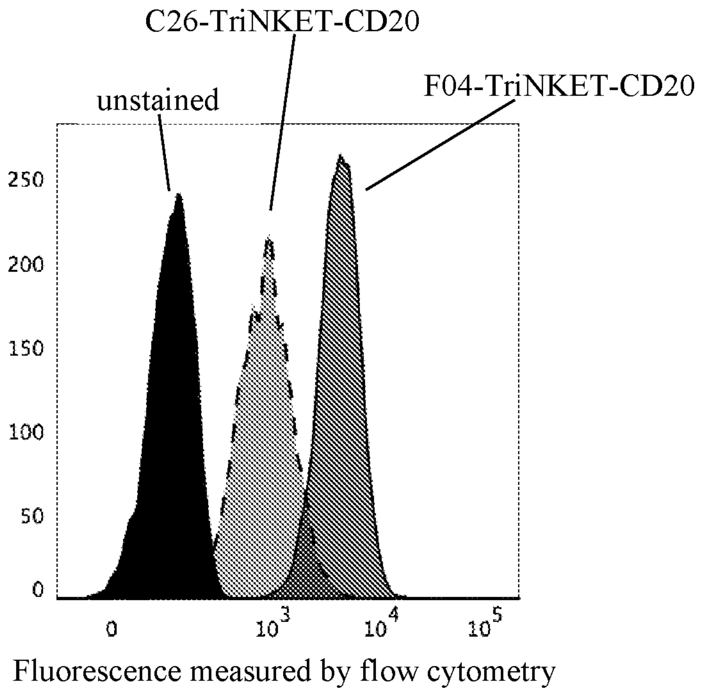
FIG. 35 is a histogram showing the binding of CD20-targeting TriNKETs to NKG2D expressed on EL4 cells. Unstained EL4 cells were used a negative control for fluorescence signal. Unstained: filled; F04-TriNKET-CD20: solid line; CD26-TriNKET-CD20: dashed line.

EL4 mouse lymphoma cell lines were engineered to express human NKG2D. Trispecific-binding proteins (TriNKETs) that each contain an NKG2D-binding domain, a tumor-associated antigen binding domain (such as a CD20-binding domain), and an Fc domain that binds to CD16 as shown in FIG. 1, were tested for their affinity to extracellular NKG2D expressed on EL4 cells. TriNKETs were diluted to 20 μg/mL, and then diluted serially. The binding of the TriNKETs to NKG2D was detected using fluorophore-conjugated anti-human IgG secondary antibodies. Cells were then analyzed by flow cytometry and histogram was plotted. TriNKETs tested include CD26-TriNKET-CD20 (an NKG2D-binding domain from clone ADI-28226 and a CD20-binding domain derived from rituximab), and F04-TriNKET-CD20 (an NKG2D-binding domain from clone ADI-29404 and a CD20-binding domain derived from rituximab). Binding profiles of CD26-TriNKET-CD20 (dashed line), and F04-TriNKET-CD20 (solid line) are shown in FIG. 35 together with an unstained sample. The result shows different levels of binding to NKG2D by clones ADI-28226 and ADI-29404.

Figure 36:
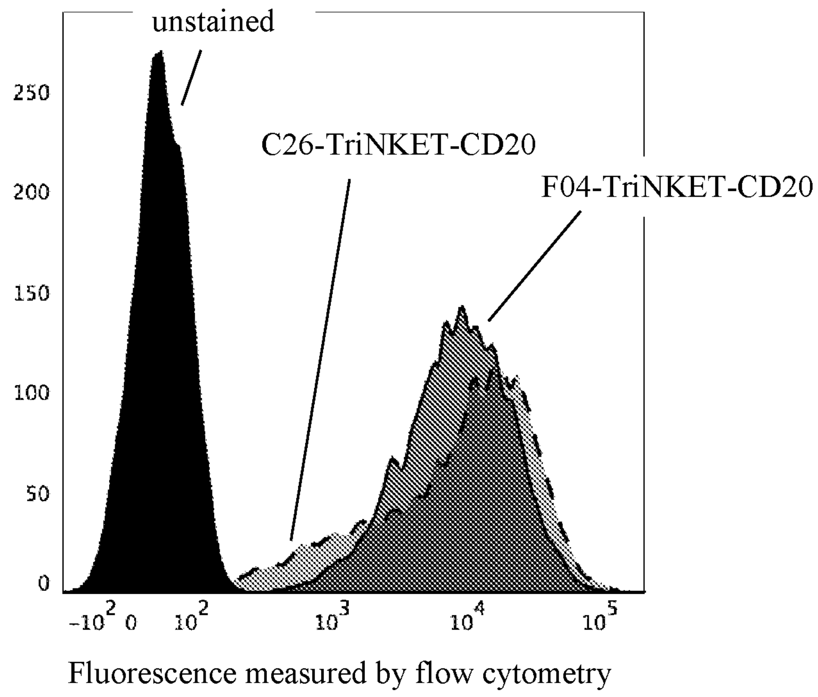
FIG. 36 is a histogram showing the binding of CD20-targeting TriNKETs to CD20 expressed on Raji human lymphoma cells. Unstained cells were used a negative control for fluorescence signal. Unstained: filled; F04-TriNKET-CD20: solid line; CD26-TriNKET-CD20: dashed line.

Example 9—Assessment of TriNKETs Binding to Cell-Expressed Human Cancer Antigens Raji human lymphoma cells expressing CD20 were used to assay the binding of TriNKETs to the tumor associated antigen CD20. TriNKETs were incubated with the cells, and the binding was detected using fluorophore-conjugated anti-human IgG secondary antibodies. Cells were analyzed by flow cytometry and histogram was plotted. As shown in FIG. 36, F04-TriNKET-CD20 and CD26-TriNKET-CD20 bind to CD20 equally well.

Example 10—TriNKETs Activate NK Cells

Peripheral blood mononuclear cells (PBMCs) were isolated from human peripheral blood buffy coats using density gradient centrifugation. NK cells ($CD3^-CD56^+$) were isolated using negative selection with magnetic beads from PBMCs, and the purity of the isolated NK cells was typically >90%. Isolated NK cells were cultured in media containing 100 ng/mL IL-2 for activation or rested overnight without cytokine. IL-2-activated NK cells were used within 24-48 hours after activation. Rested NK cells were always used on the same day after purification.

Human cancer cells expressing a tumor antigen were harvested and resuspended in culture media at $2\times10^6$/mL. Monoclonal antibodies or TriNKETs targeting the tumor antigen were diluted in culture media. Rested and/or activated NK cells were harvested, washed, and resuspended at $2\times10^6$/mL in culture media. Cancer cells were then mixed with monoclonal antibodies/TriNKETs and activated NK cells in the presence of IL-2. Brefeldin-A and monensin were also added to the mixed culture to block protein transport out of the cell for intracellular cytokine staining. Fluorophore-conjugated anti-CD107a was added to the mixed culture and the culture was incubated for 4 hours before samples were prepared for FACS analysis using fluorophore-conjugated antibodies against CD3, CD56 and IFN-γ. CD107a and IFN-γ staining was analyzed in $CD3^-$ $CD56^+$ cells to assess NK cell activation. The increase in CD107a/IFN-γ double-positive cells is indicative of better NK cell activation through engagement of two activating receptors rather than one receptor.

Figure 37:
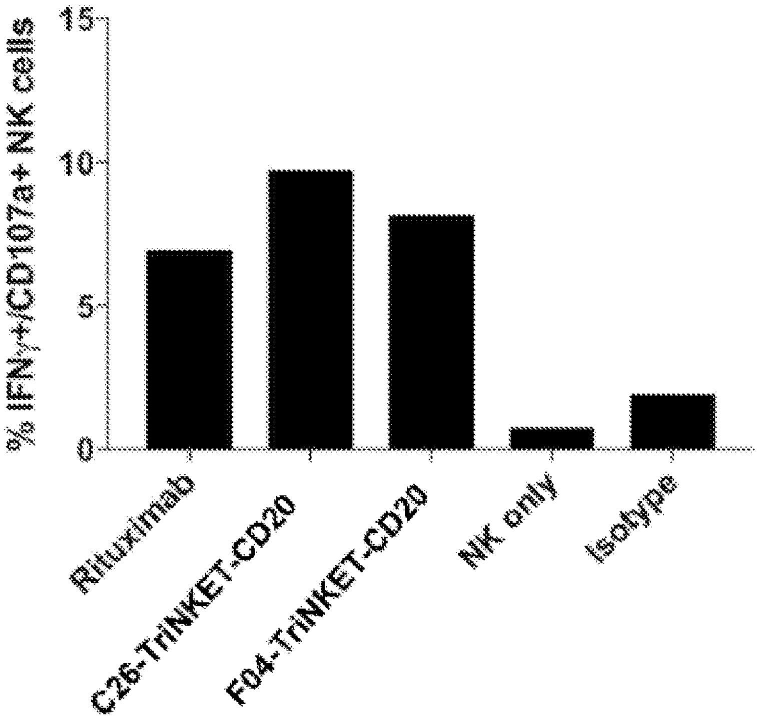
FIG. 37 is a bar graph showing that human NK cells were activated by TriNKETs when they were co-cultured with CD20+ Raji B cell lymphoma cells indicated by an increase of CD107a/IFN-γ double-positive cells.
Figure 38:
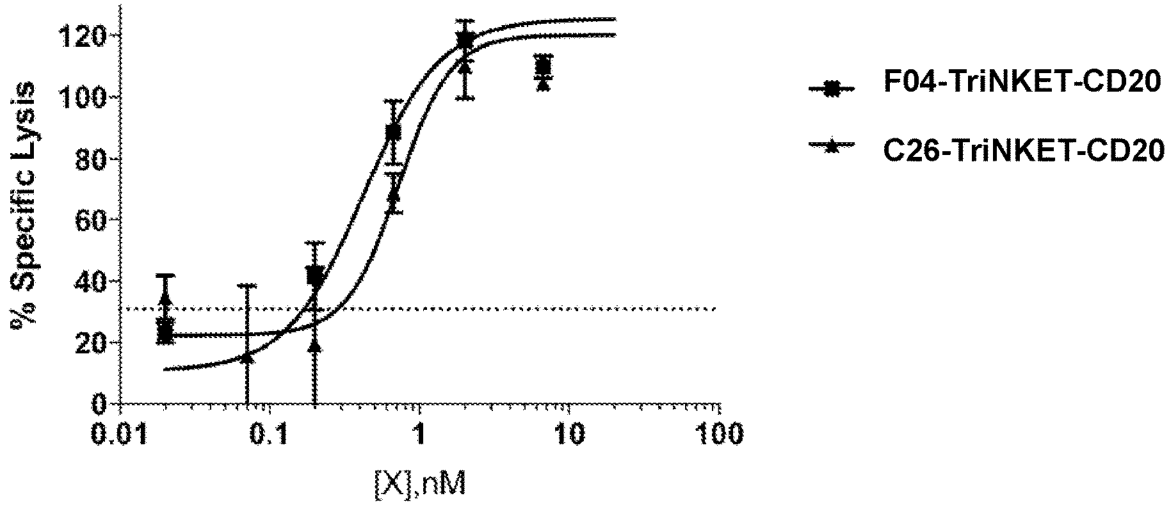
FIG. 38 is a line graph demonstrating TriNKETs-mediated cytotoxic activity of human NK cells towards CD20-expressing Raji B cell lymphoma cells.

Co-culturing primary human NK cells with CD20-positive human cancer cells resulted in TriNKET-mediated activation of primary human NK cells (FIG. 37). TriNKETs targeting CD20 (e.g., C26-TriNKET-CD20 and F04-TriNKET-CD20), mediated activation of human NK cells co-cultured with CD20-positive Raji cells, as indicated by an increase in CD107a degranulation and IFN-γ cytokine production (FIG. 37). Compared to the monoclonal antibody rituximab, both TriNKETs (e.g., C26-TriNKET-CD20 and F04-TriNKET-CD20) showed superior activation of human NK cells.

Example 11—TriNKETs Enhance Cytotoxicity of Human NK Cells Towards Cancer Cells

In order to test the ability of human NK cells to lyse cancer cells in the presence of TriNKETs, human NK cell line KHYG-1 cells transduced to express human CD16a-158v were used as effector cells. All cytotoxicity assays were prepared as follows: human cancer cell lines expressing a target of interest (e.g., CD20 positive Raji cells) were harvested from culture, cells were washed with PBS, and were resuspended in growth media at $10^6$/mL for labeling with BATDA reagent (Perkin Elmer AD0116). Manufacturer instructions were followed for labeling of the target cells. After labeling, cells were washed 3× with PBS and resuspended at $0.5\text{-}1.0\times10^5$/mL in the culture media. To prepare the background wells an aliquot of the labeled cells was put aside, and the cells were spun out of the media. 100 μl of the media were carefully added to wells in triplicate to avoid disturbing the pelleted cells. 100 μl of BATDA labeled cells were added to each well of a 96-well plate. Wells were saved for spontaneous release from target cells, and wells were prepared for maximal lysis of target cells by addition of 1% Triton-X. Monoclonal antibodies or TriNKETs against the tumor target of interest were diluted in culture media and 50 μl of diluted monoclonal antibodies or TriNKETs were added to each well. KHYG-1-CD16-158V cells were washed, and were resuspended at $10^5\text{-}2.0\times10^6$/mL in culture media depending on the desired effector cell to target cell ratio. 50 μl of NK cells were added to each well of the plate to make a total of 200 μl culture volume. The plate was incubated at 37° C. with 5% CO2 for 2-3 hours before developing the assay.

After culturing for 2-3 hours, the plate was removed from the incubator and the cells were pelleted by centrifugation at 200 g for 5 minutes. 20 μl of culture supernatant was transferred to a clean microplate provided from the manufacturer, 200 μl of room temperature europium solution was added to each well. The plate was protected from the light and incubated on a plate shaker at 250 rpm for 15 minutes. Plate was read using either Victor 3 or SpectraMax i3X instruments. % Specific lysis was calculated as follows: % Specific lysis=((Experimental release−Spontaneous release)/(Maximum release−Spontaneous release))*100%.

Figure 39:
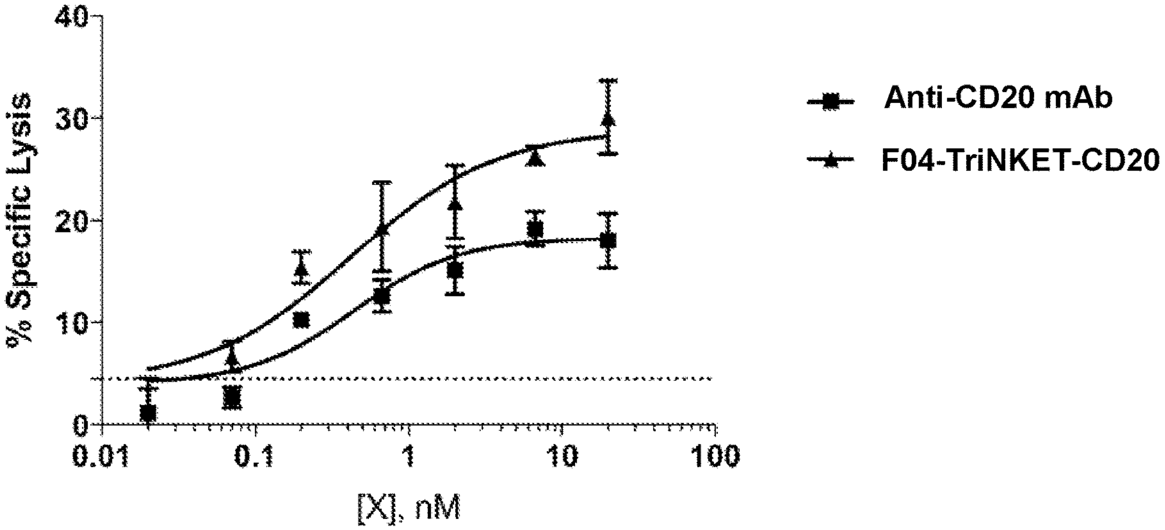
FIG. 39 is a line graph demonstrating that the TriNKET mediated higher NK cell cytotoxicity towards CD20-expressing Raji B cell lymphoma cells than the parental anti-CD20 monoclonal antibody.

CD20-targeting TriNKETs mediate cytotoxicity of human NK cells towards the CD20 positive Raji B cell lymphoma cells. As shown in FIG. 39, both TriNKETs (C26-TriNKET-CD20 and F04-TriNKET-CD20) were able to enhance the cytotoxic activity of rested human KHYG-1-CD16a-158V effector cells towards the cancer cells in a dose-responsive manner KHYG-1-CD16a-158V cells were weakly active towards Raji cells without the addition of TriNKETs. The dotted line indicates the specific lysis of Raji target cells without addition of TriNKETs.

F04-TriNKET-CD20, which mediates cytotoxicity of NK cells towards CD20-expressing cancer cells, was compared with the parental monoclonal antibody rituximab. F04-TriNKET-CD20 or the anti-CD20 monoclonal antibody rituximab was mixed with KHYG-1-CD16a-158V cells (KHYG-1 cells transduced to express human CD16a-158V) and Raji cells, and NK cell mediated cytotoxicity was measured as described above. FIG. 39 shows that F04-TriNKET-CD20 enhanced the potency and maximum killing of NK cell cytotoxicity towards Raji cells compared with the anti-CD20 monoclonal antibody. The dotted line indicates the specific lysis of Raji target cells by KHYG-1-CD16a-158V cells without addition of the TriNKET or the anti-CD20 monoclonal antibody.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A protein comprising:

(a) a first antigen-binding site, wherein the first antigen-binding site is a Fab comprising a heavy chain variable domain (VH) and a light chain variable domain (VL) of an anti-NKG2D antibody;

(b) a second antigen-binding site, wherein the second antigen-binding site is an scFv comprising a VH and a VL of an anti-CD19 antibody;

(c) a first polypeptide of an antibody Fc domain of human IgG1; and (d) a second polypeptide of the antibody Fc domain of human IgG1;

wherein the first polypeptide of the antibody Fc domain and the second polypeptide of the antibody Fc domain together bind CD16;

wherein the first and second polypeptides of the antibody Fc domain each comprise an N-terminus;

wherein the first antigen-binding site is linked to the N-terminus of the first polypeptide of the antibody Fc domain, and the second antigen-binding site is linked to the N-terminus of the second polypeptide of the antibody Fc domain; and wherein binding of the protein results in synergistic activation of NK cells, and the synergistic activation is determined by increased expression of one or both of CD107a and IFNγ.

2. The protein of claim 1, wherein the first antigen-binding site binds to NKG2D in humans and cynomolgus monkeys.

3. A protein according to claim 1, wherein the antibody Fc domain comprises hinge and CH2 domains.

4. The protein according to claim 3, wherein the antibody Fc domain comprises an amino acid sequence at least 90% identical to the Fc domain of human IgG1 and differs from the Fc domain of the human IgG1 at one or more positions selected from the group consisting of Q347, Y349, L351, S354, E356, E357, K360, Q362, S364, T366, L368, K370, N390, K392, T394, D399, S400, D401, F405, Y407, K409, T411, and K439.

5. The protein of claim 4, wherein the first polypeptide of the antibody Fc domain comprises K360E and K409W substitutions, and the second polypeptide of the antibody Fc domain comprises Q347R, D399V and F405T substitutions.

6. A formulation comprising the protein according to claim 1 and a pharmaceutically acceptable carrier.

7. A cell comprising one or more nucleic acids encoding the protein according to claim 1.

8. The protein according to claim 1, wherein the second antigen-binding site comprises:

a heavy chain complementarity-determining region 1 (VHCDR1), a heavy chain complementarity-determining region 2 (VHCDR2), a heavy chain complementarity-determining region 3 (VHCDR3), a light chain complementarity-determining region 1 (VLCDR1), a light chain complementarity-determining region 2 (VLCDR2), and a light chain complementarity determining region 3 (VLCDR3) comprising amino acid sequences of 1) SEQ ID NOs: 176, 177, 178, 180, 181, and 182, respectively, 2) SEQ ID NOs: 184, 185, 186, 188, 189, and 190, respectively, 3) SEQ ID NOs: 192, 193, 194, 196, 197, and 198, respectively, or 4) SEQ ID NOs: 200, 201, 202, 204, 205, and 206, respectively.

9. The protein according to claim 8, wherein:

(a) the VH of the anti-CD19 antibody comprises an amino acid sequence at least 90% identical to the amino acid sequence of SEQ ID NO: 175 and the VL of the anti-CD19 antibody comprises an amino acid sequence at least 90% identical to the amino acid sequence of SEQ ID NO: 179;

(b) the VH of the anti-CD19 antibody comprises an amino acid sequence at least 90% identical to the amino acid sequence of SEQ ID NO:183 and the VL of the anti-CD19 antibody comprises an amino acid sequence at least 90% identical to the amino acid sequence of SEQ ID NO: 187;

(c) the VH of the anti-CD19 antibody comprises an amino acid sequence at least 90% identical to the amino acid sequence of SEQ ID NO: 191 and the VL of the anti-CD19 antibody comprises an amino acid sequence at least 90% identical to the amino acid sequence of SEQ ID NO: 195; or (d) the VH of the anti-CD19 antibody comprises an amino acid sequence at least 90% identical to the amino acid sequence of SEQ ID NO: 199 and the VL of the anti-CD19 antibody comprises an amino acid sequence at least 90% identical to the amino acid sequence of SEQ ID NO: 203.

10. The protein according to claim 1, wherein the first antigen-binding site comprises:

(a) heavy chain complementarity-determining region 1 (VH CDR1), heavy chain complementarity-determining region 2 (VH CDR2), heavy chain complementarity-determining region 3 (VH CDR3), light chain complementarity-determining region 1 (VL CDR1), light chain complementarity-determining region 2 (VL CDR2), and light chain complementarity determining region 3 (VL CDR3) sequences identical to the amino acid sequences of SEQ ID NO: 43, SEQ ID NO:44, SEQ ID NO:45, SEQ ID NO:46, SEQ ID NO:47, and SEQ ID NO:48, respectively;

(b) VH CDR1, VH CDR2, VH CDR3, VL CDR1, VL CDR2, and VL CDR3 sequences identical to the amino acid sequences of SEQ ID NO:51, SEQ ID NO:52, SEQ ID NO:53, SEQ ID NO: 54, SEQ ID NO:55, and SEQ ID NO:56, respectively; or (c) VH CDR1, VH CDR2, VH CDR3, VL CDR1, VL CDR2, and VL CDR3 sequences identical to the amino acid sequences of SEQ ID NO:324, SEQ ID NO:325, SEQ ID NO:326, SEQ ID NO:327, SEQ ID NO:328, and SEQ ID NO:329, respectively.

11. The protein according to claim 1, wherein:

(a) the VH of the first antigen-binding site comprises an amino acid sequence identical to the sequence of SEQ ID NO:41 and the VL of the first antigen-binding site comprises an amino acid sequence identical to the sequence of SEQ ID NO:42;

(b) the VH of the first antigen-binding site comprises an amino acid sequence identical to the sequence of SEQ ID NO:49 and the VL of the first antigen-binding site comprises an amino acid sequence identical to the sequence of SEQ ID NO:50;

(c) the VH of the first antigen-binding site comprises an amino acid sequence identical to the sequence of SEQ ID NO:57 and the VL of the first antigen-binding site comprises an amino acid sequence identical to the sequence of SEQ ID NO:58;

(d) the VH of the first antigen-binding site comprises an amino acid sequence identical to the sequence of SEQ ID NO:59 and the VL of the first antigen-binding site comprises an amino acid sequence identical to the sequence of SEQ ID NO:60;

(e) the VH of the first antigen-binding site comprises an amino acid sequence identical to the sequence of SEQ ID NO: 101 and the VL of the first antigen-binding site comprises an amino acid sequence identical to the sequence of SEQ ID NO: 102; or (f) the VH of the first antigen-binding site comprises an amino acid sequence identical to the sequence of SEQ ID NO: 103 and the VL of the first antigen-binding site comprises an amino acid sequence identical to the sequence of SEQ ID NO:104.

12. A method of enhancing tumor cell death, the method comprising exposing the tumor cell and a natural killer cell to an effective amount of the protein according to claim 1.

13. A method of treating cancer, wherein the method comprises administering an effective amount of the protein according to claim 1 to a patient in need thereof, wherein the cancer is selected from the group consisting of chronic lymphocytic leukemia, non-Hodgkin's lymphoma, follicular lymphoma, acute lymphoblastic leukemia, B cell malignancies, multiple myeloma, and acute myeloid leukemia.

* * * * *

SEQUENCE LISTING

<160> NUMBER OF SEQ ID NOS: 329

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 1

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Ile
                85                  90                  95

Thr Phe Gly Gly Gly Thr Lys Val Glu Ile Lys
            100                 105
```

<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gly Gly Thr Lys Val Glu Ile Lys
            100                 105


<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60
```

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ala Arg Gly Pro Trp Ser Phe Asp Pro Trp Gly Gln Gly Thr Leu
100 105 110

Val Thr Val Ser Ser
115

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Gly Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr His Ser Phe Tyr Thr
85 90 95

Phe Gly Gly Gly Thr Lys Val Glu Ile Lys
100 105

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asp His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ala Arg Gly Pro Trp Ser Phe Asp Pro Trp Gly Gln Gly Thr Leu
100 105 110

Val Thr Val Ser Ser
115

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Ser Tyr Tyr Thr
                85                  90                  95

Phe Gly Gly Gly Thr Lys Val Glu Ile Lys
            100                 105
```

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 10

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Pro Thr
85 90 95

Phe Gly Gly Gly Thr Lys Val Glu Ile Lys
100 105

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asp His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ala Arg Gly Pro Trp Gly Phe Asp Pro Trp Gly Gln Gly Thr Leu
100 105 110

Val Thr Val Ser Ser
115

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Glu Leu Gln Met Thr Gln Ser Pro Ser Ser Leu Ser Ala Ser Val Gly
1 5 10 15

Asp Arg Val Thr Ile Thr Cys Arg Thr Ser Gln Ser Ile Ser Ser Tyr
20 25 30

Leu Asn Trp Tyr Gln Gln Lys Pro Gly Gln Pro Pro Lys Leu Leu Ile
35 40 45

Tyr Trp Ala Ser Thr Arg Glu Ser Gly Val Pro Asp Arg Phe Ser Gly
50 55 60

-continued

```
Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105


<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Ile
                85                  90                  95

Thr Phe Gly Gly Gly Thr Lys Val Glu Ile Lys
            100                 105


<210> SEQ ID NO 15
<211> LENGTH: 117
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Lys Glu Val Pro Trp
                85                  90                  95

Thr Phe Gly Gln Gly Thr Lys Val Glu Ile Lys
            100                 105


<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
```

```
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 18
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105


<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 20
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ile Tyr Pro Thr
                85                  90                  95

Phe Gly Gly Gly Thr Lys Val Glu Ile Lys
            100                 105


<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 22
<211> LENGTH: 106
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105


<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30
```

```
Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105


<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Phe Pro Thr
                85                  90                  95
```

```
Phe Gly Gly Gly Thr Lys Val Glu Ile Lys
            100                 105


<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Ser Thr
                85                  90                  95

Phe Gly Gly Gly Thr Lys Val Glu Ile Lys
            100                 105


<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 29

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 30
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Ser Thr
                85                  90                  95

Phe Gly Gly Gly Thr Lys Val Glu Ile Lys
            100                 105

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Phe Ile Thr
                85                  90                  95

Phe Gly Gly Gly Thr Lys Val Glu Ile Lys
            100                 105

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
115

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 34

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Gln Ser Tyr Pro Thr
85 90 95

Phe Gly Gly Gly Thr Lys Val Glu Ile Lys
100 105

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asp His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ala Arg Gly Pro Trp Ser Phe Asp Pro Trp Gly Gln Gly Thr Leu
100 105 110

Val Thr Val Ser Ser
115

<210> SEQ ID NO 36
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Pro Thr
                85                  90                  95

Phe Gly Gly Gly Thr Lys Val Glu Ile Lys
            100                 105

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly

```
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Leu Tyr Ser Tyr
                85                  90                  95

Thr Phe Gly Gly Gly Thr Lys Val Glu Ile Lys
            100                 105


<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Phe Ile Thr
                85                  90                  95

Phe Gly Gly Gly Thr Lys Val Glu Ile Lys
            100                 105
```

<210> SEQ ID NO 41
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Asp Ser Ser Ile Arg His Ala Tyr Tyr Tyr Tyr Gly Met
100 105 110

Asp Val Trp Gly Gln Gly Thr Thr Val Thr Val Ser Ser
115 120 125

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Ile Thr Phe Gly Gly Gly Thr Lys Val Glu Ile
100 105 110

Lys

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Gly Thr Phe Ser Ser Tyr Ala Ile Ser
1 5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Gly Ile Ile Pro Ile Phe Gly Thr Ala Asn Tyr Ala Gln Lys Phe Gln
1 5 10 15

Gly

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Ala Arg Gly Asp Ser Ser Ile Arg His Ala Tyr Tyr Tyr Tyr Gly Met
1 5 10 15

Asp Val

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Lys Ser Ser Gln Ser Val Leu Tyr Ser Ser Asn Asn Lys Asn Tyr Leu
1 5 10 15

Ala

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Trp Ala Ser Thr Arg Glu Ser
1 5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Gln Gln Tyr Tyr Ser Thr Pro Ile Thr
1 5

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Asp Arg Phe His Pro Tyr Phe Asp Tyr Trp Gly
            100                 105                 110

Gln Gly Thr Leu Val Thr Val Ser Ser
        115                 120
```

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Thr Trp Pro Pro
                85                  90                  95

Thr Phe Gly Gly Gly Thr Lys Val Glu Ile Lys
            100                 105
```

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

```
Gly Ser Ile Ser Ser Ser Ser Tyr Tyr Trp Gly
```

1 5 10

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Ser Ile Tyr Tyr Ser Gly Ser Thr Tyr Tyr Asn Pro Ser Leu Lys Ser
1 5 10 15

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Ala Arg Gly Ser Asp Arg Phe His Pro Tyr Phe Asp Tyr
1 5 10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Arg Ala Ser Gln Ser Val Ser Arg Tyr Leu Ala
1 5 10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Asp Ala Ser Asn Arg Ala Thr
1 5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Gln Gln Phe Asp Thr Trp Pro Pro Thr
1 5

<210> SEQ ID NO 57
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asp His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ala Arg Gly Pro Trp Ser Phe Asp Pro Trp Gly Gln Gly Thr Leu
100 105 110

Val Thr Val Ser Ser
115

<210> SEQ ID NO 58
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 58

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Glu Gln Tyr Asp Ser Tyr Pro Thr
85 90 95

Phe Gly Gly Gly Thr Lys Val Glu Ile Lys
100 105

<210> SEQ ID NO 59
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 59

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Arg Lys Ala Ser Gly Ser Phe Tyr Tyr Tyr Tyr Gly
            100                 105                 110

Met Asp Val Trp Gly Gln Gly Thr Thr Val Thr Val Ser Ser
        115                 120                 125

<210> SEQ ID NO 60
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 61
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Asn Tyr Gly Asp Thr Thr His Asp Tyr Tyr Tyr
100 105 110

Met Asp Val Trp Gly Lys Gly Thr Thr Val Thr Val Ser Ser
115 120 125

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asp Asp Trp Pro Phe
85 90 95

Thr Phe Gly Gly Gly Thr Lys Val Glu Ile Lys
100 105

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Tyr Thr Phe Thr Ser Tyr Tyr Met His
1 5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Ile Ile Asn Pro Ser Gly Gly Ser Thr Ser Tyr Ala Gln Lys Phe Gln
1 5 10 15

Gly

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Ala Arg Gly Ala Pro Asn Tyr Gly Asp Thr Thr His Asp Tyr Tyr Tyr
1 5 10 15

Met Asp Val

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Arg Ala Ser Gln Ser Val Ser Ser Asn Leu Ala
1 5 10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Gly Ala Ser Thr Arg Ala Thr
1 5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Gln Gln Tyr Asp Asp Trp Pro Phe Thr
1 5

<210> SEQ ID NO 69
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Thr Gly Glu Tyr Tyr Asp Thr Asp Asp His Gly Met Asp
100 105 110

Val Trp Gly Gln Gly Thr Thr Val Thr Val Ser Ser
115 120

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Asp Asp Tyr Trp Pro Pro
85 90 95

Thr Phe Gly Gly Gly Thr Lys Val Glu Ile Lys
100 105

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Tyr Thr Phe Thr Gly Tyr Tyr Met His
1 5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Trp Ile Asn Pro Asn Ser Gly Gly Thr Asn Tyr Ala Gln Lys Phe Gln
1 5 10 15

Gly

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Ala Arg Asp Thr Gly Glu Tyr Tyr Asp Thr Asp Asp His Gly Met Asp
1 5 10 15

Val

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Arg Ala Ser Gln Ser Val Ser Ser Asn Leu Ala
1 5 10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Gly Ala Ser Thr Arg Ala Thr
1 5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Gln Gln Asp Asp Tyr Trp Pro Pro Thr
1 5

<210> SEQ ID NO 77
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Gly Gly Tyr Tyr Asp Ser Gly Ala Gly Asp Tyr Trp Gly
100 105 110

Gln Gly Thr Leu Val Thr Val Ser Ser
115 120

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Asp Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Val Ser Tyr Pro Arg
85 90 95

Thr Phe Gly Gly Gly Thr Lys Val Glu Ile Lys
100 105

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Phe Thr Phe Ser Ser Tyr Ala Met Ser
1 5

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Ala Ile Ser Gly Ser Gly Gly Ser Thr Tyr Tyr Ala Asp Ser Val Lys
1 5 10 15

Gly

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Ala Lys Asp Gly Gly Tyr Tyr Asp Ser Gly Ala Gly Asp Tyr
1 5 10

<210> SEQ ID NO 82
<211> LENGTH: 11

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

```
Arg Ala Ser Gln Gly Ile Asp Ser Trp Leu Ala
1               5                   10
```

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

```
Ala Ala Ser Ser Leu Gln Ser
1               5
```

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

```
Gln Gln Gly Val Ser Tyr Pro Arg Thr
1               5
```

<210> SEQ ID NO 85
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 85

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Ala Gly Trp Phe Asp Pro Trp
            100                 105                 110

Gly Gln Gly Thr Leu Val Thr Val Ser Ser
        115                 120
```

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 86

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Val Ser Phe Pro Arg
85 90 95

Thr Phe Gly Gly Gly Thr Lys Val Glu Ile Lys
100 105

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Phe Thr Phe Ser Ser Tyr Ser Met Asn
1 5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Ser Ile Ser Ser Ser Ser Ser Tyr Ile Tyr Tyr Ala Asp Ser Val Lys
1 5 10 15

Gly

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Ala Arg Gly Ala Pro Met Gly Ala Ala Ala Gly Trp Phe Asp Pro
1 5 10 15

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Arg Ala Ser Gln Gly Ile Ser Ser Trp Leu Ala
1 5 10

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Ala Ala Ser Ser Leu Gln Ser
1 5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Gln Gln Gly Val Ser Phe Pro Arg Thr
1 5

<210> SEQ ID NO 93
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Glu Gly Ala Gly Phe Ala Tyr Gly Met Asp Tyr Tyr Tyr Met
100 105 110

Asp Val Trp Gly Lys Gly Thr Thr Val Thr Val Ser Ser
115 120 125

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Phe
                85                  90                  95

Thr Phe Gly Gly Gly Thr Lys Val Glu Ile Lys
            100                 105

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Tyr Thr Phe Thr Ser Tyr Tyr Met His
1               5

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ile Ile Asn Pro Ser Gly Gly Ser Thr Ser Tyr Ala Gln Lys Phe Gln
1               5                   10                  15

Gly

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Glu Gly Ala Gly Phe Ala Tyr Gly Met Asp Tyr Tyr Tyr Met
1               5                   10                  15

Asp Val

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ala Ser Gln Ser Val Ser Ser Tyr Leu Ala
1 5 10

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Asp Ala Ser Asn Arg Ala Thr
1 5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Gln Gln Ser Asp Asn Trp Pro Phe Thr
1 5

<210> SEQ ID NO 101
<211> LENGTH: 121
<212> TYPE: PRT
<213> ORGANISM: Homo sapiens

<400> SEQUENCE: 101

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Arg Gly Leu Gly Asp Gly Thr Tyr Phe Asp Tyr Trp Gly
100 105 110

Gln Gly Thr Thr Val Thr Val Ser Ser
115 120

<210> SEQ ID NO 102
<211> LENGTH: 110
<212> TYPE: PRT
<213> ORGANISM: Homo sapiens

<400> SEQUENCE: 102

Gln Ser Ala Leu Thr Gln Pro Ala Ser Val Ser Gly Ser Pro Gly Gln
1 5 10 15

Ser Ile Thr Ile Ser Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

```
Ile Tyr Tyr Asp Asp Leu Leu Pro Ser Gly Val Ser Asp Arg Phe Ser
    50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 103
<211> LENGTH: 115
<212> TYPE: PRT
<213> ORGANISM: Homo sapiens

<400> SEQUENCE: 103

Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
        115


<210> SEQ ID NO 104
<211> LENGTH: 108
<212> TYPE: PRT
<213> ORGANISM: Homo sapiens

<400> SEQUENCE: 104

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 105
<211> LENGTH: 9
<212> TYPE: PRT
<213> ORGANISM: Artificial Sequence
```

<220> FEATURE:
<223> OTHER INFORMATION: Description of Artificial Sequence: Synthetic peptide

<400> SEQUENCE: 105

Gly Ser Phe Ser Gly Tyr Tyr Trp Ser
1 5

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Glu Ile Asp His Ser Gly Ser Thr Asn Tyr Asn Pro Ser Leu Lys Ser
1 5 10 15

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Ala Arg Ala Arg Gly Pro Trp Ser Phe Asp Pro
1 5 10

<210> SEQ ID NO 108
<211> LENGTH: 246
<212> TYPE: PRT
<213> ORGANISM: Homo sapiens

<400> SEQUENCE: 108

Met Ala Ala Ala Ala Ile Pro Ala Leu Leu Leu Cys Leu Pro Leu Leu
1 5 10 15

Phe Leu Leu Phe Gly Trp Ser Arg Ala Arg Arg Asp Asp Pro His Ser
20 25 30

Leu Cys Tyr Asp Ile Thr Val Ile Pro Lys Phe Arg Pro Gly Pro Arg
35 40 45

Trp Cys Ala Val Gln Gly Gln Val Asp Glu Lys Thr Phe Leu His Tyr
50 55 60

Asp Cys Gly Asn Lys Thr Val Thr Pro Val Ser Pro Leu Gly Lys Lys
65 70 75 80

Leu Asn Val Thr Met Ala Trp Lys Ala Gln Asn Pro Val Leu Arg Glu
85 90 95

Val Val Asp Ile Leu Thr Glu Gln Leu Leu Asp Ile Gln Leu Glu Asn
100 105 110

Tyr Thr Pro Lys Glu Pro Leu Thr Leu Gln Ala Arg Met Ser Cys Glu
115 120 125

Gln Lys Ala Glu Gly His Ser Ser Gly Ser Trp Gln Phe Ser Ile Asp
130 135 140

Gly Gln Thr Phe Leu Leu Phe Asp Ser Glu Lys Arg Met Trp Thr Thr
145 150 155 160

Val His Pro Gly Ala Arg Lys Met Lys Glu Lys Trp Glu Asn Asp Lys
165 170 175

Asp Val Ala Met Ser Phe His Tyr Ile Ser Met Gly Asp Cys Ile Gly 180 185 190

Trp Leu Glu Asp Phe Leu Met Gly Met Asp Ser Thr Leu Glu Pro Ser
195 200 205

Ala Gly Ala Pro Leu Ala Met Ser Ser Gly Thr Thr Gln Leu Arg Ala
210 215 220

Thr Ala Thr Thr Leu Ile Leu Cys Cys Leu Leu Ile Ile Leu Pro Cys
225 230 235 240

Phe Ile Leu Pro Gly Ile
245

<210> SEQ ID NO 109
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Gly Tyr
20 25 30

Asn Met Asn Trp Val Arg Gln Met Pro Gly Lys Gly Leu Glu Trp Met
35 40 45

Gly Asn Ile Asp Pro Tyr Tyr Gly Gly Thr Thr Tyr Asn Arg Lys Phe
50 55 60

Lys Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Ser Val Gly Pro Phe Asp Ser Trp Gly Gln Gly Thr Leu Val
100 105 110

Thr Val Ser Ser Gly
115

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Gly Tyr Ser Phe Thr Gly Tyr
1 5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Asp Pro Tyr Tyr Gly Gly
1 5

<210> SEQ ID NO 112

<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Ser Val Gly Pro Phe Asp Ser
1 5

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

Glu Ile Val Leu Thr Gln Ser Pro Ala Thr Leu Ser Leu Ser Pro Gly
1 5 10 15

Glu Arg Ala Thr Leu Ser Cys Arg Ala Ser Glu Asn Val Tyr Ser Tyr
20 25 30

Leu Ala Trp Tyr Gln Gln Lys Pro Gly Gln Ala Pro Arg Leu Leu Ile
35 40 45

Tyr Phe Ala Lys Thr Leu Ala Glu Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln His His Ser Asp Asn Pro Trp
85 90 95

Thr Phe Gly Gln Gly Thr Lys Val Glu Ile Lys
100 105

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Glu Asn Val Tyr Ser Tyr Leu Ala
1 5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Phe Ala Lys Thr Leu Ala Glu
1 5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

```
Gln His His Ser Asp Asn Pro Trp Thr
1               5
```

<210> SEQ ID NO 117
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala
        115
```

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

```
Phe Ser Leu Thr Thr Ser Gly Val Ser
1               5
```

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

```
Val Ile Trp Gly Asp Gly Ser Thr Asn Tyr His Pro Ser Leu Lys Ser
1               5                   10                  15
```

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Gly Gly Tyr Ser Leu Ala His
1 5

<210> SEQ ID NO 121
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 121

Asp Ile Gln Met Thr Gln Ser Pro Ser Ser Leu Ser Val Ser Val Gly
1 5 10 15

Glu Arg Val Thr Ile Thr Cys Arg Ala Ser Glu Asn Ile Arg Ser Asn
20 25 30

Leu Ala Trp Tyr Gln Gln Lys Pro Gly Lys Ser Pro Lys Leu Leu Val
35 40 45

Asn Val Ala Thr Asn Leu Ala Asp Gly Val Pro Ser Arg Phe Ser Gly
50 55 60

Ser Gly Ser Gly Thr Asp Tyr Ser Leu Lys Ile Asn Ser Leu Gln Pro
65 70 75 80

Glu Asp Phe Gly Thr Tyr Tyr Cys Gln His Tyr Trp Gly Thr Thr Trp
85 90 95

Thr Phe Gly Gln Gly Thr Lys Leu Glu Ile Lys Arg
100 105

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Glu Asn Ile Arg Ser Asn Leu Ala
1 5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Asn Val Ala Thr Asn Leu Ala
1 5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Gln His Tyr Trp Gly Thr Thr Trp Thr
1 5

<210> SEQ ID NO 125
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 125

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Pro Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Ala Gly Asp Phe Asp Tyr Trp Gly Gln Gly Thr Leu Val Thr
            100                 105                 110

Val Ser Ser Ala
        115
```

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

```
Gly Ser Phe Ser Pro Tyr Tyr Trp Ser
1               5
```

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

```
Glu Ile Asn His Ser Gly Ser Thr Asn Tyr Asn Pro Ser Leu Lys Ser
1               5                   10                  15
```

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

```
Arg Ala Gly Asp Phe Asp Tyr
1               5
```

<210> SEQ ID NO 129

<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 129

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Ile Phe
85 90 95

Gly Gln Gly Thr Lys Leu Glu Ile Lys Arg
100 105

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Arg Ala Ser Gln Ser Ile Ser Ser Trp Leu Ala
1 5 10

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Lys Ala Ser Ser Leu Glu Ser
1 5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Gln Gln Tyr Asn Ser Tyr Ile
1 5

<210> SEQ ID NO 133
<211> LENGTH: 281
<212> TYPE: PRT
<213> ORGANISM: Homo sapiens

<400> SEQUENCE: 133

Met Ser Ala Gln Glu Ser Cys Leu Ser Leu Ile Lys Tyr Phe Leu Phe
1 5 10 15

Val Phe Asn Leu Phe Phe Phe Val Leu Gly Ser Leu Ile Phe Cys Phe
20 25 30

Gly Ile Trp Ile Leu Ile Asp Lys Thr Ser Phe Val Ser Phe Val Gly
35 40 45

Leu Ala Phe Val Pro Leu Gln Ile Trp Ser Lys Val Leu Ala Ile Ser
50 55 60

Gly Ile Phe Thr Met Gly Ile Ala Leu Leu Gly Cys Val Gly Ala Leu
65 70 75 80

Lys Glu Leu Arg Cys Leu Leu Gly Leu Tyr Phe Gly Met Leu Leu Leu
85 90 95

Leu Phe Ala Thr Gln Ile Thr Leu Gly Ile Leu Ile Ser Thr Gln Arg
100 105 110

Ala Gln Leu Glu Arg Ser Leu Arg Asp Val Val Glu Lys Thr Ile Gln
115 120 125

Lys Tyr Gly Thr Asn Pro Glu Glu Thr Ala Ala Glu Glu Ser Trp Asp
130 135 140

Tyr Val Gln Phe Gln Leu Arg Cys Cys Gly Trp His Tyr Pro Gln Asp
145 150 155 160

Trp Phe Gln Val Leu Ile Leu Arg Gly Asn Gly Ser Glu Ala His Arg
165 170 175

Val Pro Cys Ser Cys Tyr Asn Leu Ser Ala Thr Asn Asp Ser Thr Ile
180 185 190

Leu Asp Lys Val Ile Leu Pro Gln Leu Ser Arg Leu Gly His Leu Ala
195 200 205

Arg Ser Arg His Ser Ala Asp Ile Cys Ala Val Pro Ala Glu Ser His
210 215 220

Ile Tyr Arg Glu Gly Cys Ala Gln Gly Leu Gln Lys Trp Leu His Asn
225 230 235 240

Asn Leu Ile Ser Ile Val Gly Ile Cys Leu Gly Val Gly Leu Leu Glu
245 250 255

Leu Gly Phe Met Thr Leu Ser Ile Phe Leu Cys Arg Asn Leu Asp His
260 265 270

Val Tyr Asn Arg Leu Ala Arg Tyr Arg
275 280

<210> SEQ ID NO 134
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Gln Val Gln Leu Gln Gln Pro Gly Ala Glu Leu Val Lys Pro Gly Ala
1 5 10 15

Ser Val Lys Met Ser Cys Lys Ala Ser Gly Tyr Thr Phe Thr Ser Tyr
20 25 30

Asn Met His Trp Val Lys Gln Thr Pro Gly Arg Gly Leu Glu Trp Ile
35 40 45

Gly Ala Ile Tyr Pro Gly Asn Gly Asp Thr Ser Tyr Asn Gln Lys Phe
50 55 60

Lys Gly Lys Ala Thr Leu Thr Ala Asp Lys Ser Ser Ser Thr Ala Tyr

```
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala
        115                 120


<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Tyr Thr Phe Thr Ser Tyr
1               5


<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Tyr Pro Gly Asn Gly Asp
1               5


<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Thr Tyr Tyr Gly Gly Asp Trp Tyr Phe Asn Val
1               5                   10


<210> SEQ ID NO 138
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80
```

```
Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg
            100                 105
```

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

```
Ser Ser Val Ser Tyr Ile His
1               5
```

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

```
Ala Thr Ser Asn Leu Ala Ser
1               5
```

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

```
Gln Gln Trp Thr Ser Asn Pro Pro Thr
1               5
```

<210> SEQ ID NO 142
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 142

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110
```

Thr Leu Val Thr Val Ser Ser Ala
115 120

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Gly Tyr Ala Phe Ser Tyr Ser
1 5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Phe Pro Gly Asp Gly Asp
1 5

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Asn Val Phe Asp Gly Tyr Trp Leu Val Tyr
1 5 10

<210> SEQ ID NO 146
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

Asp Ile Val Met Thr Gln Thr Pro Leu Ser Leu Pro Val Thr Pro Gly
1 5 10 15

Glu Pro Ala Ser Ile Ser Cys Arg Ser Ser Lys Ser Leu Leu His Ser
20 25 30

Asn Gly Ile Thr Tyr Leu Tyr Trp Tyr Leu Gln Lys Pro Gly Gln Ser
35 40 45

Pro Gln Leu Leu Ile Tyr Gln Met Ser Asn Leu Val Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ala Gln Asn
85 90 95

Leu Glu Leu Pro Tyr Thr Phe Gly Gly Gly Thr Lys Val Glu Ile Lys
100 105 110

Arg

<210> SEQ ID NO 147
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

```
Lys Ser Leu Leu His Ser Asn Gly Ile Thr Tyr Leu Tyr
1               5                   10
```

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

```
Gln Met Ser Asn Leu Val Ser
1               5
```

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

```
Gln Met Ser Asn Leu Val Ser
1               5
```

<210> SEQ ID NO 150
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala
        115                 120
```

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Gly Phe Thr Phe Asn Asp Tyr
1 5

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Ser Trp Asn Ser Gly Ser
1 5

<210> SEQ ID NO 153
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Asp Ile Gln Tyr Gly Asn Tyr Tyr Tyr Gly Met Asp Val
1 5 10

<210> SEQ ID NO 154
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Ile
85 90 95

Thr Phe Gly Gln Gly Thr Arg Leu Glu Ile Lys Arg
100 105

<210> SEQ ID NO 155
<211> LENGTH: 8
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 155

Gln Ser Val Ser Ser Tyr Leu Ala
1 5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Asp Ala Ser Asn Arg Ala Thr
1 5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 157

Gln Gln Arg Ser Asn Trp Pro Ile Thr
1 5

<210> SEQ ID NO 158
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 158

Gln Val Gln Leu Gln Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Asn Met His Trp Val Lys Gln Ala Pro Gly Gln Gly Leu Glu Trp Ile
35 40 45

Gly Ala Ile Tyr Pro Gly Met Gly Asp Thr Ser Tyr Asn Gln Lys Phe
50 55 60

Lys Gly Lys Ala Thr Leu Thr Ala Asp Glu Ser Thr Asn Thr Ala Tyr
65 70 75 80

Met Glu Leu Ser Ser Leu Arg Ser Glu Asp Thr Ala Phe Tyr Tyr Cys
85 90 95

Ala Arg Ser Thr Tyr Tyr Gly Gly Asp Trp Tyr Phe Asp Val Trp Gly
100 105 110

Gln Gly Thr Thr Val Thr Val Ser Ser Ala
115 120

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Gly Tyr Thr Phe Thr Ser Tyr
1 5

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Tyr Pro Gly Met Gly Asp
1 5

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Ser Thr Tyr Tyr Gly Gly Asp Trp Tyr Phe Asp Val
1 5 10

<210> SEQ ID NO 162
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 162

Asp Ile Gln Leu Thr Gln Ser Pro Ser Ser Leu Ser Ala Ser Val Gly
1 5 10 15

Asp Arg Val Thr Met Thr Cys Arg Ala Ser Ser Ser Val Ser Tyr Ile
20 25 30

His Trp Phe Gln Gln Lys Pro Gly Lys Ala Pro Lys Pro Trp Ile Tyr
35 40 45

Ala Thr Ser Asn Leu Ala Ser Gly Val Pro Val Arg Phe Ser Gly Ser
50 55 60

Gly Ser Gly Thr Asp Tyr Thr Phe Thr Ile Ser Ser Leu Gln Pro Glu
65 70 75 80

Asp Ile Ala Thr Tyr Tyr Cys Gln Gln Trp Thr Ser Asn Pro Pro Thr
85 90 95

Phe Gly Gly Gly Thr Lys Leu Glu Ile Lys Arg
100 105

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Ser Ser Val Ser Tyr Ile His
1 5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 164

Ala Thr Ser Asn Leu Ala Ser
1 5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 165

Gln Gln Trp Thr Ser Asn Pro Pro Thr
1 5

<210> SEQ ID NO 166
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 166

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Thr Ser Tyr
20 25 30

Asn Met His Trp Val Arg Gln Ala Pro Gly Lys Gly Leu Glu Trp Val
35 40 45

Gly Ala Ile Tyr Pro Gly Asn Gly Asp Thr Ser Tyr Asn Gln Lys Phe
50 55 60

Lys Gly Arg Phe Thr Ile Ser Val Asp Lys Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Val Val Tyr Tyr Ser Asn Ser Tyr Trp Tyr Phe Asp Val Trp
100 105 110

Gly Gln Gly Thr Leu Val Thr Val Ser Ser Ala
115 120

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 167

Gly Tyr Thr Phe Thr Ser Tyr
1 5

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Tyr Pro Gly Asn Gly Asp
1 5

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Val Val Tyr Tyr Ser Asn Ser Tyr Trp Tyr Phe Asp Val
1 5 10

<210> SEQ ID NO 170
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Asp Ile Gln Met Thr Gln Ser Pro Ser Ser Leu Ser Ala Ser Val Gly
1 5 10 15

Asp Arg Val Thr Ile Thr Cys Arg Ala Ser Ser Ser Val Ser Tyr Met
20 25 30

His Trp Tyr Gln Gln Lys Pro Gly Lys Ala Pro Lys Pro Leu Ile Tyr
35 40 45

Ala Pro Ser Asn Leu Ala Ser Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

Asp Phe Ala Thr Tyr Tyr Cys Gln Gln Trp Ser Phe Asn Pro Pro Thr
85 90 95

Phe Gly Gln Gly Thr Lys Val Glu Ile Lys Arg
100 105

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Ser Ser Val Ser Tyr Met His
1 5

<210> SEQ ID NO 172
<211> LENGTH: 7
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 172

Ala Pro Ser Asn Leu Ala Ser
1 5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Gln Gln Trp Ser Phe Asn Pro Pro Thr
1 5

<210> SEQ ID NO 174
<211> LENGTH: 297
<212> TYPE: PRT
<213> ORGANISM: Homo sapiens

<400> SEQUENCE: 174

Met Thr Thr Pro Arg Asn Ser Val Asn Gly Thr Phe Pro Ala Glu Pro
1 5 10 15

Met Lys Gly Pro Ile Ala Met Gln Ser Gly Pro Lys Pro Leu Phe Arg
20 25 30

Arg Met Ser Ser Leu Val Gly Pro Thr Gln Ser Phe Phe Met Arg Glu
35 40 45

Ser Lys Thr Leu Gly Ala Val Gln Ile Met Asn Gly Leu Phe His Ile
50 55 60

Ala Leu Gly Gly Leu Leu Met Ile Pro Ala Gly Ile Tyr Ala Pro Ile
65 70 75 80

Cys Val Thr Val Trp Tyr Pro Leu Trp Gly Gly Ile Met Tyr Ile Ile
85 90 95

Ser Gly Ser Leu Leu Ala Ala Thr Glu Lys Asn Ser Arg Lys Cys Leu
100 105 110

Val Lys Gly Lys Met Ile Met Asn Ser Leu Ser Leu Phe Ala Ala Ile
115 120 125

Ser Gly Met Ile Leu Ser Ile Met Asp Ile Leu Asn Ile Lys Ile Ser
130 135 140

His Phe Leu Lys Met Glu Ser Leu Asn Phe Ile Arg Ala His Thr Pro
145 150 155 160

Tyr Ile Asn Ile Tyr Asn Cys Glu Pro Ala Asn Pro Ser Glu Lys Asn
165 170 175

Ser Pro Ser Thr Gln Tyr Cys Tyr Ser Ile Gln Ser Leu Phe Leu Gly
180 185 190

Ile Leu Ser Val Met Leu Ile Phe Ala Phe Phe Gln Glu Leu Val Ile
195 200 205

Ala Gly Ile Val Glu Asn Glu Trp Lys Arg Thr Cys Ser Arg Pro Lys
210 215 220

Ser Asn Ile Val Leu Leu Ser Ala Glu Glu Lys Lys Glu Gln Thr Ile
225 230 235 240

Glu Ile Lys Glu Glu Val Val Gly Leu Thr Glu Thr Ser Ser Gln Pro
245 250 255

Lys Asn Glu Glu Asp Ile Glu Ile Ile Pro Ile Gln Glu Glu Glu Glu

```
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295


<210> SEQ ID NO 175
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Gly
        115                 120                 125


<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Tyr Ala Phe Ser Ser Tyr
1               5


<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Trp Pro Gly Asp Gly Asp
1               5


<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 178

Arg Glu Thr Thr Thr Val Gly Arg Tyr Tyr Tyr Ala Met Asp Tyr
1               5                   10                  15

<210> SEQ ID NO 179
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gln Ser Val Asp Tyr Asp Gly Asp Ser Tyr Leu Asn
1               5                   10

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Asp Ala Ser Asn Leu Val Ser
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gln Gln Ser Thr Glu Asp Pro Trp Thr
1               5

<210> SEQ ID NO 183
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 183

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Ser
20 25 30

Trp Met Asn Trp Val Arg Gln Ala Pro Gly Lys Gly Leu Glu Trp Val
35 40 45

Gly Arg Ile Tyr Pro Gly Asp Gly Asp Thr Asn Tyr Asn Ala Lys Phe
50 55 60

Lys Gly Arg Phe Thr Ile Ser Arg Asp Asp Ser Lys Asn Ser Leu Tyr
65 70 75 80

Leu Gln Met Asn Ser Leu Lys Thr Glu Asp Thr Ala Val Tyr Tyr Cys
85 90 95

Ala Arg Ser Gly Phe Ile Thr Thr Val Arg Asp Phe Asp Tyr Trp Gly
100 105 110

Gln Gly Thr Leu Val Thr Val Ser Ser
115 120

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 184

Gly Phe Thr Phe Ser Ser Ser
1 5

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Tyr Pro Gly Asp Gly Asp
1 5

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 186

Ser Gly Phe Ile Thr Thr Val Arg Asp Phe Asp Tyr
1 5 10

<210> SEQ ID NO 187
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 187

Glu Ile Val Leu Thr Gln Ser Pro Asp Phe Gln Ser Val Thr Pro Lys
1 5 10 15

Glu Lys Val Thr Ile Thr Cys Arg Ala Ser Glu Ser Val Asp Thr Phe
20 25 30

Gly Ile Ser Phe Met Asn Trp Phe Gln Gln Lys Pro Asp Gln Ser Pro
35 40 45

Lys Leu Leu Ile His Glu Ala Ser Asn Gln Gly Ser Gly Val Pro Ser
50 55 60

Arg Phe Ser Gly Ser Gly Ser Gly Thr Asp Phe Thr Leu Thr Ile Asn
65 70 75 80

Ser Leu Glu Ala Glu Asp Ala Ala Thr Tyr Tyr Cys Gln Gln Ser Lys
85 90 95

Glu Val Pro Phe Thr Phe Gly Gly Gly Thr Lys Val Glu Ile Lys
100 105 110

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 188

Glu Ser Val Asp Thr Phe Gly Ile Ser Phe Met Asn
1 5 10

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 189

Glu Ala Ser Asn Gln Gly Ser
1 5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 190

Gln Gln Ser Lys Glu Val Pro Phe Thr
1 5

<210> SEQ ID NO 191
<211> LENGTH: 122
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 191

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser Ala
        115                 120

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Gly Tyr Thr Phe Thr Ser Tyr
1               5

<210> SEQ ID NO 193
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 193

Asn Pro Tyr Asn Asp Gly
1               5

<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 194

Gly Thr Tyr Tyr Tyr Gly Thr Arg Val Phe Asp Tyr
1               5                   10

<210> SEQ ID NO 195
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 195

Asp Ile Val Met Thr Gln Ser Pro Ala Thr Leu Ser Leu Ser Pro Gly
1 5 10 15

Glu Arg Ala Thr Leu Ser Cys Arg Ser Ser Lys Ser Leu Gln Asn Val
20 25 30

Asn Gly Asn Thr Tyr Leu Tyr Trp Phe Gln Gln Lys Pro Gly Gln Ser
35 40 45

Pro Gln Leu Leu Ile Tyr Arg Met Ser Asn Leu Asn Ser Gly Val Pro
50 55 60

Asp Arg Phe Ser Gly Ser Gly Ser Gly Thr Glu Phe Thr Leu Thr Ile
65 70 75 80

Ser Ser Leu Glu Pro Glu Asp Phe Ala Val Tyr Tyr Cys Met Gln His
85 90 95

Leu Glu Tyr Pro Ile Thr Phe Gly Ala Gly Thr Lys Leu Glu Ile Lys
100 105 110

Arg

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Lys Ser Leu Gln Asn Val Asn Gly Asn Thr Tyr Leu Tyr
1 5 10

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Arg Met Ser Asn Leu Asn Ser
1 5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Met Gln His Leu Glu Tyr Pro Ile Thr
1 5

<210> SEQ ID NO 199
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 199

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Thr Ser
20 25 30

Gly Met Gly Val Gly Trp Ile Arg Gln His Pro Gly Lys Gly Leu Glu
35 40 45

Trp Ile Gly His Ile Trp Trp Asp Asp Asp Lys Arg Tyr Asn Pro Ala
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Met Glu Leu Trp Ser Tyr Tyr Phe Asp Tyr Trp Gly Gln
100 105 110

Gly Thr Leu Val Thr Val Ser Ser
115 120

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 200

Gly Gly Ser Ile Ser Thr Ser Gly Met
1 5

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Trp Trp Asp Asp Asp
1 5

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Met Glu Leu Trp Ser Tyr Tyr Phe Asp Tyr
1 5 10

<210> SEQ ID NO 203
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 203

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Tyr Met
20 25 30

His Trp Tyr Gln Gln Lys Pro Gly Gln Ala Pro Arg Leu Leu Ile Tyr
35 40 45

Asp Thr Ser Lys Leu Ala Ser Gly Ile Pro Ala Arg Phe Ser Gly Ser
50 55 60

Gly Ser Gly Thr Asp Phe Thr Leu Thr Ile Ser Ser Leu Glu Pro Glu
65 70 75 80

Asp Val Ala Val Tyr Tyr Cys Phe Gln Gly Ser Val Tyr Pro Phe Thr
85 90 95

Phe Gly Gln Gly Thr Lys Leu Glu Ile Lys Arg
100 105

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Ser Ser Val Ser Tyr Met His
1 5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Asp Thr Ser Lys Leu Ala Ser
1 5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Phe Gln Gly Ser Val Tyr Pro Phe Thr
1 5

<210> SEQ ID NO 207
<211> LENGTH: 556
<212> TYPE: PRT
<213> ORGANISM: Homo sapiens

<400> SEQUENCE: 207

Met Pro Pro Pro Arg Leu Leu Phe Phe Leu Leu Phe Leu Thr Pro Met
1 5 10 15

Glu Val Arg Pro Glu Glu Pro Leu Val Val Lys Val Glu Glu Gly Asp
20 25 30

Asn Ala Val Leu Gln Cys Leu Lys Gly Thr Ser Asp Gly Pro Thr Gln
35 40 45

Gln Leu Thr Trp Ser Arg Glu Ser Pro Leu Lys Pro Phe Leu Lys Leu

-continued

```
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480
```

Pro His Gly Ser Ala Trp Asp Pro Ser Arg Glu Ala Thr Ser Leu Gly
485 490 495

Ser Gln Ser Tyr Glu Asp Met Arg Gly Ile Leu Tyr Ala Ala Pro Gln
500 505 510

Leu Arg Ser Ile Arg Gly Gln Pro Gly Pro Asn His Glu Glu Asp Ala
515 520 525

Asp Ser Tyr Glu Asn Met Asp Asn Pro Asp Gly Pro Asp Pro Ala Trp
530 535 540

Gly Gly Gly Gly Arg Met Gly Thr Trp Ser Thr Arg
545 550 555

<210> SEQ ID NO 208
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 208

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Leu His Trp Val Arg Gln Ala Pro Gly Gln Gly Leu Glu Trp Ile
35 40 45

Gly Tyr Ile Asn Pro Arg Asn Asp Tyr Thr Glu Tyr Asn Gln Asn Phe
50 55 60

Lys Asp Lys Ala Thr Ile Thr Ala Asp Glu Ser Thr Asn Thr Ala Tyr
65 70 75 80

Met Glu Leu Ser Ser Leu Arg Ser Glu Asp Thr Ala Phe Tyr Phe Cys
85 90 95

Ala Arg Arg Asp Ile Thr Thr Phe Tyr Trp Gly Gln Gly Thr Thr Val
100 105 110

Thr Val Ser Ser
115

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Gly Tyr Thr Phe Thr Ser Tyr
1 5

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Asn Pro Arg Asn Asp Tyr
1 5

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 211

Arg Asp Ile Thr Thr Phe Tyr
1 5

<210> SEQ ID NO 212
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 212

Asp Ile Gln Leu Thr Gln Ser Pro Ser Ser Leu Ser Ala Ser Val Gly
1 5 10 15

Asp Arg Val Thr Met Ser Cys Lys Ser Ser Gln Ser Val Leu Tyr Ser
20 25 30

Ala Asn His Lys Asn Tyr Leu Ala Trp Tyr Gln Gln Lys Pro Gly Lys
35 40 45

Ala Pro Lys Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Gln Pro Glu Asp Ile Ala Thr Tyr Tyr Cys His Gln
85 90 95

Tyr Leu Ser Ser Trp Thr Phe Gly Gly Gly Thr Lys Leu Glu Ile Lys
100 105 110

<210> SEQ ID NO 213
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Gln Ser Val Leu Tyr Ser Ala Asn His Lys Asn Tyr Leu Ala
1 5 10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Trp Ala Ser Thr Arg Glu Ser
1 5

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

His Gln Tyr Leu Ser Ser Trp Thr
1 5

<210> SEQ ID NO 216
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 216

Gln Leu Val Gln Ser Gly Ala Glu Val Lys Lys Pro Gly Ala Ser Val
1 5 10 15

Lys Val Ser Cys Lys Ala Ser Gly Tyr Arg Phe Thr Asn Tyr Trp Ile
20 25 30

His Trp Val Arg Gln Ala Pro Gly Gln Gly Leu Glu Trp Ile Gly Gly
35 40 45

Ile Asn Pro Gly Asn Asn Tyr Ala Thr Tyr Arg Arg Lys Phe Gln Gly
50 55 60

Arg Val Thr Met Thr Ala Asp Thr Ser Thr Ser Thr Val Tyr Met Glu
65 70 75 80

Leu Ser Ser Leu Arg Ser Glu Asp Thr Ala Val Tyr Tyr Cys Thr Arg
85 90 95

Glu Gly Tyr Gly Asn Tyr Gly Ala Trp Phe Ala Tyr Trp Gly Gln Gly
100 105 110

Thr Leu Val Thr Val Ser Ser Ala
115 120

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Gly Tyr Arg Phe Thr Asn Tyr
1 5

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Asn Pro Gly Asn Asn Tyr
1 5

<210> SEQ ID NO 219
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Glu Gly Tyr Gly Asn Tyr Gly Ala Trp Phe Ala Tyr
1 5 10

<210> SEQ ID NO 220
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 220

Asp Val Gln Val Thr Gln Ser Pro Ser Ser Leu Ser Ala Ser Val Gly
1 5 10 15

Asp Arg Val Thr Ile Thr Cys Arg Ser Ser Gln Ser Leu Ala Asn Ser
20 25 30

Tyr Gly Asn Thr Phe Leu Ser Trp Tyr Leu His Lys Pro Gly Lys Ala
35 40 45

Pro Gln Leu Leu Ile Tyr Gly Ile Ser Asn Arg Phe Ser Gly Val Pro
50 55 60

Asp Arg Phe Ser Gly Ser Gly Ser Gly Thr Asp Phe Thr Leu Thr Ile
65 70 75 80

Ser Ser Leu Gln Pro Glu Asp Phe Ala Thr Tyr Tyr Cys Leu Gln Gly
85 90 95

Thr His Gln Pro Tyr Thr Phe Gly Gln Gly Thr Lys Val Glu Ile Lys
100 105 110

Arg

<210> SEQ ID NO 221
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Gln Ser Leu Ala Asn Ser Tyr Gly Asn Thr Phe Leu Ser
1 5 10

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Gly Ile Ser Asn Arg Phe Ser
1 5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 223

Leu Gln Gly Thr His Gln Pro Tyr Thr
1               5

<210> SEQ ID NO 224
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Ser Gly Lys Phe
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Asp Trp Tyr Phe Asp Val Trp Gly Gln
            100                 105                 110

Gly Thr Leu Val Thr Val Ser Ser Ala
        115                 120

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Tyr Glu Phe Ser Arg Ser
1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Pro Gly Asp Gly Asp
1               5

<210> SEQ ID NO 227
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asp Gly Ser Ser Trp Asp Trp Tyr Phe Asp Val 1 5 10

<210> SEQ ID NO 228
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 228

Asp Ile Gln Met Thr Gln Ser Pro Ser Ser Leu Ser Ala Ser Val Gly
1 5 10 15

Asp Arg Val Thr Ile Thr Cys Arg Ser Ser Gln Ser Ile Val His Ser
20 25 30

Val Gly Asn Thr Phe Leu Glu Trp Tyr Gln Gln Lys Pro Gly Lys Ala
35 40 45

Pro Lys Leu Leu Ile Tyr Lys Val Ser Asn Arg Phe Ser Gly Val Pro
50 55 60

Ser Arg Phe Ser Gly Ser Gly Ser Gly Thr Asp Phe Thr Leu Thr Ile
65 70 75 80

Ser Ser Leu Gln Pro Glu Asp Phe Ala Thr Tyr Tyr Cys Phe Gln Gly
85 90 95

Ser Gln Phe Pro Tyr Thr Phe Gly Gln Gly Thr Lys Val Glu Ile Lys
100 105 110

Arg

<210> SEQ ID NO 229
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 229

Gln Ser Ile Val His Ser Val Gly Asn Thr Phe Leu Glu
1 5 10

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 230

Lys Val Ser Asn Arg Phe Ser
1 5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 231

Phe Gln Gly Ser Gln Phe Pro Tyr Thr
1 5

<210> SEQ ID NO 232
<211> LENGTH: 847
<212> TYPE: PRT
<213> ORGANISM: Homo sapiens

<400> SEQUENCE: 232

Met His Leu Leu Gly Pro Trp Leu Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
    370                 375                 380

```
Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
    450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
        515                 520                 525

Cys Asp Phe Ser Ser Ser His Pro Lys Glu Val Gln Phe Phe Trp Glu
    530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
        595                 600                 605

Gly Lys Ser Ala Thr Leu Thr Cys Glu Ser Asp Ala Asn Pro Pro Val
    610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
        675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
    770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
```

```
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845


<210> SEQ ID NO 233
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala Ala
        115


<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Tyr Thr Phe Thr Asp Tyr Tyr Ile Thr
1               5                   10


<210> SEQ ID NO 235
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Tyr Pro Gly Ser Gly Asn
1               5


<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 236

Tyr Gly Asn Tyr Trp Phe Ala Tyr
1               5


<210> SEQ ID NO 237
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110


<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gln Ser Val Asp Phe Asp Gly Asp Ser Tyr Met Asn
1               5                   10


<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Ala Ser Asn Leu Glu Ser
1               5


<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gln Gln Ser Asn Glu Asp Pro Trp Thr
1               5
```

<210> SEQ ID NO 241
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 241

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser
        115                 120

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Gly Tyr Thr Phe Thr Thr Tyr Thr Ile His
1               5                   10

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 243

Tyr Ile Asn Pro Ser Ser Gly Tyr Ser Asp Tyr Asn Gln Asn Phe Lys
1               5                   10                  15

Gly

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 244

Arg Ala Asp Tyr Gly Asn Tyr Glu Tyr Thr Trp Phe Ala Tyr
1               5                   10

<210> SEQ ID NO 245
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

```
Asp Ile Val Met Thr Gln Ser Pro Lys Phe Met Ser Thr Ser Val Gly
1               5                   10                  15

Asp Arg Val Thr Val Thr Cys Lys Ala Ser Gln Asn Val Gly Thr Asn
            20                  25                  30

Val Ala Trp Phe Gln Gln Lys Pro Gly Gln Ser Pro Lys Val Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr His Thr Tyr Pro Leu
                85                  90                  95

Thr Phe Gly Gly Gly Thr Lys Leu Glu Ile Asn
            100                 105
```

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

```
Gln Asn Val Gly Thr Asn Val Ala
1               5
```

<210> SEQ ID NO 247
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

```
Ser Ala Ser Tyr Arg Tyr Ser
1               5
```

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

```
Gln Gln Tyr His Thr Tyr Pro Leu Thr
1               5
```

<210> SEQ ID NO 249
<211> LENGTH: 112
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 249

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Ala Tyr
20 25 30

Tyr Trp Ser Trp Ile Arg Gln Pro Pro Gly Lys Gly Leu Glu Trp Ile
35 40 45

Gly Asp Ile Asn His Gly Gly Gly Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Asn Ser Val Thr Ala Ala Asp Thr Ala Val Tyr Tyr Cys Ala
85 90 95

Ser Leu Thr Ala Tyr Trp Gly Gln Gly Ser Leu Val Thr Val Ser Ser
100 105 110

<210> SEQ ID NO 250
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 250

Ala Tyr Tyr Trp Ser
1 5

<210> SEQ ID NO 251
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 251

Asp Ile Asn His Gly Gly Gly Thr Asn Tyr Asn Pro Ser Leu Lys Ser
1 5 10 15

<210> SEQ ID NO 252
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 252

Leu Thr Ala Tyr
1

<210> SEQ ID NO 253
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 253

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Thr Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asp Ser Tyr Pro Ile
85 90 95

Thr Phe Gly Gln Gly Thr Arg Leu Glu Ile Lys
100 105

<210> SEQ ID NO 254
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 254

Arg Ala Ser Gln Gly Ile Ser Ser Trp Leu Thr
1 5 10

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Ala Ala Ser Ser Leu Gln Ser
1 5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 256

Gln Gln Tyr Asp Ser Tyr Pro Ile Thr
1 5

<210> SEQ ID NO 257
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 257

Glu Val Gln Leu Val Glu Ser Gly Gly Gly Leu Val Gln Pro Gly Gly
1 5 10 15

```
Ser Leu Arg Leu Ser Cys Val Ala Ser Gly Phe Thr Phe Ser Asn Ser
            20                  25                  30

Trp Met Ser Trp Val Arg Gln Ala Pro Gly Lys Gly Leu Glu Trp Val
        35                  40                  45

Ala Asn Ile Asn Glu Asp Gly Ser Glu Lys Phe Tyr Val Asp Ser Val
    50                  55                  60

Lys Gly Arg Phe Thr Phe Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val His Trp Tyr Phe His Leu Trp Gly Arg Gly Thr Leu Val
            100                 105                 110

Thr Val Ser Ser
        115


<210> SEQ ID NO 258
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Asn Ser Trp Met Ser
1               5


<210> SEQ ID NO 259
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Asn Ile Asn Glu Asp Gly Ser Glu Lys Phe Tyr Val Asp Ser Val Lys
1               5                   10                  15

Gly


<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val His Trp Tyr Phe His Leu
1               5


<210> SEQ ID NO 261
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 262
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Arg Ala Ser Gln Ser Val Ser Ser Ser Tyr Leu Ala
1               5                   10


<210> SEQ ID NO 263
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gly Ala Ser Ser Arg Ala Thr
1               5


<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gln Gln Tyr Gly Ser Ser Pro Trp Thr
1               5


<210> SEQ ID NO 265
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45
```

```
Gly Glu Ile Asn His Ser Gly Ser Thr Lys Tyr Thr Pro Ser Leu Lys
    50                  55                  60

Ser Arg Val Thr Ile Ser Val Asp Thr Ser Lys His Gln Phe Ser Leu
65                  70                  75                  80

Lys Leu Ser Ser Val Thr Ala Ala Asp Thr Ala Val Tyr Tyr Cys Ala
                85                  90                  95

Arg Glu Thr Val Tyr Tyr Phe Asp Leu Trp Gly Arg Gly Thr Leu Val
            100                 105                 110

Thr Val Ser Ser
        115


<210> SEQ ID NO 266
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gly Tyr Tyr Trp Ser
1               5


<210> SEQ ID NO 267
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Glu Ile Asn His Ser Gly Ser Thr Lys Tyr Thr Pro Ser Leu Lys Ser
1               5                   10                  15


<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Glu Thr Val Tyr Tyr Phe Asp Leu
1               5


<210> SEQ ID NO 269
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Leu Ser Gly
```

50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Trp
85 90 95

Thr Phe Gly Gln Gly Thr Lys Val Glu Ile Lys
100 105

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

Arg Ala Ser Gln Ser Val Ser Ser Asn Leu Ala
1 5 10

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 271

Asp Ala Ser Asn Arg Ala Thr
1 5

<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

Gln Gln Arg Ser Asn Trp Pro Trp Thr
1 5

<210> SEQ ID NO 273
<211> LENGTH: 595
<212> TYPE: PRT
<213> ORGANISM: Homo sapiens

<400> SEQUENCE: 273

Met Arg Val Leu Leu Ala Ala Leu Gly Leu Leu Phe Leu Gly Ala Leu
1 5 10 15

Arg Ala Phe Pro Gln Asp Arg Pro Phe Glu Asp Thr Cys His Gly Asn
20 25 30

Pro Ser His Tyr Tyr Asp Lys Ala Val Arg Arg Cys Cys Tyr Arg Cys
35 40 45

Pro Met Gly Leu Phe Pro Thr Gln Gln Cys Pro Gln Arg Pro Thr Asp
50 55 60

Cys Arg Lys Gln Cys Glu Pro Asp Tyr Tyr Leu Asp Glu Ala Asp Arg
65 70 75 80

Cys Thr Ala Cys Val Thr Cys Ser Arg Asp Asp Leu Val Glu Lys Thr
85 90 95

-continued

```
Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
```

515 520 525

Thr Val Lys Ala Glu Leu Pro Glu Gly Arg Gly Leu Ala Gly Pro Ala
530 535 540

Glu Pro Glu Leu Glu Glu Glu Leu Glu Ala Asp His Thr Pro His Tyr
545 550 555 560

Pro Glu Gln Glu Thr Glu Pro Pro Leu Gly Ser Cys Ser Asp Val Met
565 570 575

Leu Ser Val Glu Glu Glu Gly Lys Glu Asp Pro Leu Pro Thr Ala Ala
580 585 590

Ser Gly Lys
595

<210> SEQ ID NO 274
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 274

Gln Val Gln Leu Gln Glu Ser Gly Pro Gly Leu Val Arg Pro Ser Gln
1 5 10 15

Thr Leu Ser Leu Thr Cys Thr Val Ser Gly Phe Thr Phe Thr Asp Phe
20 25 30

Tyr Met Asn Trp Val Arg Gln Pro Pro Gly Arg Gly Leu Glu Trp Ile
35 40 45

Gly Phe Ile Arg Asp Lys Ala Lys Gly Tyr Thr Thr Glu Tyr Asn Pro
50 55 60

Ser Val Lys Gly Arg Val Thr Met Leu Val Asp Thr Ser Lys Asn Gln
65 70 75 80

Phe Ser Leu Arg Leu Ser Ser Val Thr Ala Ala Asp Thr Ala Val Tyr
85 90 95

Tyr Cys Ala Arg Glu Gly His Thr Ala Ala Pro Phe Asp Tyr Trp Gly
100 105 110

Gln Gly Ser Leu Val Thr Val Ser Ser Ala
115 120

<210> SEQ ID NO 275
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Gly Phe Thr Phe Thr Asp Phe
1 5

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Arg Asp Lys Ala Lys Gly Tyr Thr
1 5

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 277

```
Glu Gly His Thr Ala Ala Pro Phe Asp Tyr
1               5                   10
```

<210> SEQ ID NO 278
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 278

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg
            100                 105
```

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 279

```
Gln Asn Ile Asp Lys Tyr Leu Asn
1               5
```

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 280

```
Asn Thr Asn Asn Leu Gln Thr
1               5
```

<210> SEQ ID NO 281
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 281

Leu Gln His Ile Ser Arg Pro Arg Thr
1 5

<210> SEQ ID NO 282
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 282

Glu Val His Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Gly Met Ser Trp Val Arg Gln Ala Pro Gly Lys Gly Leu Glu Leu Val
35 40 45

Ala Met Met Lys Thr Lys Gly Gly Arg Thr Tyr Tyr Pro Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Ile Tyr Tyr Cys
85 90 95

Ala Ser Asp Gly Tyr Tyr Trp Gly Gln Gly Thr Thr Val Thr Val Ser
100 105 110

Ser

<210> SEQ ID NO 283
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 283

Arg Tyr Gly Met Ser
1 5

<210> SEQ ID NO 284
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 284

Met Met Lys Thr Lys Gly Gly Arg Thr Tyr Tyr Pro Asp Ser Val Lys
1 5 10 15

Gly

<210> SEQ ID NO 285
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Asp Gly Tyr Tyr
1

<210> SEQ ID NO 286
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Asp Val Val Met Thr Gln Thr Pro Leu Ser Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Trp Gln Gly
                85                  90                  95

Thr His Leu Trp Thr Phe Gly Gly Gly Thr Lys Val Glu Ile Lys
            100                 105                 110

<210> SEQ ID NO 287
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Lys Ser Ser Gln Ser Leu Leu His Ser Asp Gly Lys Thr Tyr Leu Asn
1               5                   10                  15

<210> SEQ ID NO 288
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Leu Val Ser Lys Leu Asp Ser
1               5

<210> SEQ ID NO 289
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

```
Trp Gln Gly Thr His Leu Trp Thr
1               5


<210> SEQ ID NO 290
<211> LENGTH: 595
<212> TYPE: PRT
<213> ORGANISM: Homo sapiens

<400> SEQUENCE: 290

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
```

```
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590

Ser Gly Lys
        595


<210> SEQ ID NO 291
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Phe Glu Met His Trp Val Arg Gln Ala Pro Gly Gln Gly Leu
    50                  55                  60

Glu Trp Met Gly Asp Ile Asp Pro Gly Thr Gly Asp Thr Ala Tyr Asn
65                  70                  75                  80

Leu Lys Phe Lys Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110
```

Tyr Tyr Cys Ala Leu Gly Ala Phe Val Tyr Trp Gly Gln Gly Thr Leu
        115                 120                 125

Val Thr Val Ser Ser
    130

<210> SEQ ID NO 292
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Asp Phe Glu Met His
1               5

<210> SEQ ID NO 293
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Asp Ile Asp Pro Gly Thr Gly Asp Thr Ala Tyr Asn Leu Lys Phe Lys
1               5                   10                  15

Gly

<210> SEQ ID NO 294
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Ala Phe Val Tyr
1               5

<210> SEQ ID NO 295
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Met Lys Tyr Leu Leu Pro Thr Ala Ala Ala Gly Leu Leu Leu Leu Ala
1               5                   10                  15

Ala Gln Pro Ala Met Ala Asp Val Val Met Thr Gln Ser Pro Leu Ser
            20                  25                  30

Leu Pro Val Thr Phe Gly Glu Pro Ala Ser Ile Ser Cys Arg Ser Ser
        35                  40                  45

Gln Ser Leu Ala Asn Ser Tyr Gly Asn Thr Tyr Leu Ser Trp Tyr Leu
    50                  55                  60

Gln Lys Pro Gly Gln Ser Pro Gln Leu Leu Ile Tyr Gly Ile Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
100 105 110

Tyr Tyr Cys Leu Gln Gly Thr His Gln Pro Tyr Thr Phe Gly Gln Gly
115 120 125

Thr Lys Leu Glu Ile Lys
130

<210> SEQ ID NO 296
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Arg Ser Ser Gln Ser Leu Ala Asn Ser Tyr Gly Asn Thr Tyr Leu Ser
1 5 10 15

<210> SEQ ID NO 297
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Gly Ile Ser Asn Arg Phe Ser
1 5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Leu Gln Gly Thr His Gln Pro Tyr Thr
1 5

<210> SEQ ID NO 299
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 299

Met Asp Trp Thr Trp Ser Ile Leu Phe Leu Val Ala Ala Ala Thr Gly
1 5 10 15

Ala His Ser Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Asp Phe Glu Met His Trp Val Arg Gln Ala Pro Gly Gln Gly Leu
50 55 60

Glu Trp Met Gly Asp Ile Asp Pro Gly Thr Gly Asp Thr Ala Tyr Asn
65 70 75 80

Leu Lys Phe Lys Gly Arg Val Thr Met Thr Thr Asp Thr Ser Thr Ser
85 90 95

Thr Ala Tyr Met Glu Leu Arg Ser Leu Arg Ser Asp Asp Thr Ala Val
            100                 105                 110

Tyr Tyr Cys Ala Leu Gly Ala Phe Val Tyr Trp Gly Gln Gly Thr Leu
        115                 120                 125

Val Thr Val Ser Ser
    130

<210> SEQ ID NO 300
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Asp Phe Glu Met His
1               5

<210> SEQ ID NO 301
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asp Ile Asp Pro Gly Thr Gly Asp Thr Ala Tyr Asn Leu Lys Phe Lys
1               5                   10                  15

Gly

<210> SEQ ID NO 302
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gly Ala Phe Val Tyr
1               5

<210> SEQ ID NO 303
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Met Lys Tyr Leu Leu Pro Thr Ala Ala Ala Gly Leu Leu Leu Leu Ala
1               5                   10                  15

Ala Gln Pro Ala Met Ala Asp Val Val Met Thr Gln Ser Pro Leu Ser
            20                  25                  30

Leu Pro Val Thr Phe Gly Glu Gln Ala Ser Ile Ser Cys Arg Ser Ser
        35                  40                  45

Gln Ser Leu Ala Asn Ser Tyr Gly Asn Thr Tyr Leu Ser Trp Tyr Leu
    50                  55                  60

Gln Lys Pro Gly Gln Ser Pro Gln Leu Leu Ile Tyr Gly Ile Ser Asn
65                  70                  75                  80

Arg Phe Ser Gly Val Pro Asp Arg Phe Ser Gly Ser Gly Ser Gly Thr
85 90 95

Asp Phe Thr Leu Lys Ile Ser Arg Val Glu Ala Glu Asp Val Gly Val
100 105 110

Tyr Tyr Cys Leu Gln Gly Thr His Gln Pro Tyr Thr Phe Gly Gln Gly
115 120 125

Thr Lys Leu Glu Ile Lys
130

<210> SEQ ID NO 304
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

Arg Ser Ser Gln Ser Leu Ala Asn Ser Tyr Gly Asn Thr Tyr Leu Ser
1 5 10 15

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 305

Gly Ile Ser Asn Arg Phe Ser
1 5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

Leu Gln Gly Thr His Gln Pro Tyr Thr
1 5

<210> SEQ ID NO 307
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 307

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Ile Asp Leu Asn
35 40 45

Asn Tyr Asn Met Gln Trp Val Arg Gln Ala Pro Gly Lys Gly Leu Glu
50 55 60

Trp Ile Gly Ala Thr Phe Gly Ser Asp Ser Ile Tyr Tyr Ala Thr Trp 65 70 75 80

Ala Lys Gly Arg Phe Thr Ile Ser Lys Thr Ser Thr Thr Val Asp Leu
85 90 95

Lys Met Thr Ser Leu Thr Thr Glu Asp Thr Ala Thr Tyr Phe Cys Ala
100 105 110

Arg Gly Gly Leu Trp Gly Pro Gly Thr Leu Val Thr Val Ser Ser
115 120 125

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Gly Ile Asp Leu Asn Asn Tyr Asn Met Gln
1 5 10

<210> SEQ ID NO 309
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 309

Ala Thr Phe Gly Ser Asp Ser Ile Tyr Tyr Ala Thr Trp Ala
1 5 10

<210> SEQ ID NO 310
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 310

Gly Gly Leu
1

<210> SEQ ID NO 311
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 311

Met Asp Thr Arg Ala Pro Thr Gln Leu Leu Gly Leu Leu Leu Leu Trp
1 5 10 15

Leu Pro Gly Val Thr Phe Ala Gln Val Leu Thr Gln Thr Ala Ser Pro
20 25 30

Val Ser Ala Ala Val Gly Ala Thr Val Thr Ile Asn Cys Gln Ser Ser
35 40 45

Gln Ser Val Tyr Asn Asn Asn Tyr Leu Ala Trp Phe Gln Gln Lys Pro
50 55 60

Gly Gln Pro Pro Lys Leu Leu Ile Tyr Arg Ala Ser Thr Leu Ala Ser
65 70 75 80

```
Gly Val Ser Ser Arg Phe Lys Gly Ser Gly Ser Gly Thr Gln Phe Ala
                85                  90                  95

Leu Thr Ile Ser Gly Val Gln Cys Asp Asp Ala Gly Thr Tyr Tyr Cys
            100                 105                 110

Gln Gly Glu Phe Ser Cys Asp Ser Ala Asp Cys Ala Ala Phe Gly Gly
        115                 120                 125

Gly Thr Glu Val Val Val Lys Gly
    130                 135


<210> SEQ ID NO 312
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gln Ser Ser Gln Ser Val Tyr Asn Asn Asn Tyr Leu
1               5                   10


<210> SEQ ID NO 313
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Arg Ala Ser Thr Leu Ala Ser
1               5


<210> SEQ ID NO 314
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gln Gly Glu Phe Ser Cys Asp Ser Ala Asp Cys Ala Ala
1               5                   10


<210> SEQ ID NO 315
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Arg Tyr Ala Met Ser Trp Val Arg Gln Ala Pro Gly Lys Gly Leu Asp
    50                  55                  60

Trp Ile Gly Tyr Ile Asp Ile Gly Gly Gly Ala Tyr Tyr Ala Ser Trp
65                  70                  75                  80
```

Ala Lys Gly Arg Phe Thr Ile Ser Glu Thr Ser Thr Thr Val Tyr Leu
85 90 95

Lys Val Asn Ser Pro Thr Thr Glu Asp Thr Ala Thr Tyr Phe Cys Ala
100 105 110

Arg Gly Val Ala Asn Ser Asp Ile Trp Gly Pro Gly Thr Leu Val Thr
115 120 125

Val Ser Ser
130

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 316

Gly Phe Ser Leu Ser Arg Tyr Ala Met Ser
1 5 10

<210> SEQ ID NO 317
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 317

Tyr Ile Asp Ile Gly Gly Gly Ala Tyr Tyr Ala Ser Trp Ala
1 5 10

<210> SEQ ID NO 318
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 318

Gly Val Ala Asn Ser Asp Ile
1 5

<210> SEQ ID NO 319
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 319

Met Asp Thr Arg Ala Pro Thr Gln Leu Leu Gly Leu Leu Leu Leu Trp
1 5 10 15

Leu Pro Gly Ala Arg Cys Ala Leu Val Met Thr Gln Thr Pro Ser Pro
20 25 30

Val Ser Ala Ala Val Gly Gly Thr Val Thr Ile Asn Cys Gln Ser Ser
35 40 45

Gln Ser Val Phe Asn Asn Lys Trp Leu Ser Trp Tyr Gln Gln Lys Pro
50 55 60

Gly Gln Pro Pro Lys Leu Leu Ile Tyr Phe Val Ser Thr Leu Ala Ser 65 70 75 80

Gly Val Pro Ser Arg Phe Lys Gly Ser Gly Ser Gly Thr Gln Phe Thr
85 90 95

Leu Thr Ile Ser Gly Val Gln Cys Asp Asp Ala Ala Thr Tyr Tyr Cys
100 105 110

Gln Gly Ser Asp Tyr Ser Ser Gly Trp Tyr Ser Pro Phe Gly Gly Gly
115 120 125

Thr Glu Val Val Val Glu Gly
130 135

<210> SEQ ID NO 320
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 320

Gln Ser Ser Gln Ser Val Phe Asn Asn Lys Trp Leu Ser
1 5 10

<210> SEQ ID NO 321
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 321

Phe Val Ser Thr Leu Ala Ser
1 5

<210> SEQ ID NO 322
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

Gln Gly Ser Asp Tyr Ser Ser Gly Trp Tyr Ser Pro
1 5 10

<210> SEQ ID NO 323
<211> LENGTH: 865
<212> TYPE: PRT
<213> ORGANISM: Homo sapiens

<400> SEQUENCE: 323

Met Ala Leu Val Leu Gly Ser Leu Leu Leu Leu Gly Leu Cys Gly Asn
1 5 10 15

Ser Phe Ser Gly Gly Gln Pro Ser Ser Thr Asp Ala Pro Lys Ala Trp
20 25 30

Asn Tyr Glu Leu Pro Ala Thr Asn Tyr Glu Thr Gln Asp Ser His Lys
35 40 45

Ala Gly Pro Ile Gly Ile Leu Phe Glu Leu Val His Ile Phe Leu Tyr
50 55 60

Val Val Gln Pro Arg Asp Phe Pro Glu Asp Thr Leu Arg Lys Phe Leu
65 70 75 80

```
Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365

Asp Arg Val Gln Arg Gln Thr Thr Thr Val Val Ala Gly Ile Lys Arg
    370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
            420                 425                 430

Tyr Trp Trp Leu Gly Gly Leu Val Ile Cys Ser Leu Leu Thr Leu Ile
        435                 440                 445

Val Ile Phe Tyr Tyr Leu Gly Leu Leu Cys Gly Val Cys Gly Tyr Asp
    450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
```

```
            500                 505                 510

Lys Leu Ile Cys Glu Pro Tyr Thr Ser Lys Glu Leu Phe Arg Val Leu
        515                 520                 525

Asp Thr Pro Tyr Leu Leu Asn Glu Asp Trp Glu Tyr Tyr Leu Ser Gly
    530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Gln Arg Val Leu Pro Ile
        675                 680                 685

Glu Gln Ser Leu Ser Thr Leu Tyr Gln Ser Val Lys Ile Leu Gln Arg
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
        755                 760                 765

Lys Pro Val Ala Thr Ala Leu Asp Thr Ala Val Asp Val Phe Leu Cys
    770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
        835                 840                 845

Asp His Val Tyr Gly Ile His Asn Pro Val Met Thr Ser Pro Ser Gln
    850                 855                 860

His
865
```

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 324

Gly Thr Phe Ser Ser Tyr Ala Ile Ser
1 5

<210> SEQ ID NO 325
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 325

Gly Ile Ile Pro Ile Phe Gly Thr Ala Asn Tyr Ala Gln Lys Phe Gln
1 5 10 15

Gly

<210> SEQ ID NO 326
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 326

Ala Arg Arg Gly Arg Lys Ala Ser Gly Ser Phe Tyr Tyr Tyr Tyr Gly
1 5 10 15

Met Asp Val

<210> SEQ ID NO 327
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 327

Glu Ser Ser Gln Ser Leu Leu Asn Ser Gly Asn Gln Lys Asn Tyr Leu
1 5 10 15

Thr

<210> SEQ ID NO 328
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 328

Trp Ala Ser Thr Arg Glu Ser
1 5

<210> SEQ ID NO 329
<211> LENGTH: 9
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 329

Gln Asn Asp Tyr Ser Tyr Pro Tyr Thr
1               5
```